United States Patent [19]

Reyes et al.

[11] Patent Number: 5,789,559

[45] Date of Patent: Aug. 4, 1998

[54] DNA SEQUENCES OF ENTERICALLY TRANSMITTED NON-A/NON-B HEPATITIS VIRAL AGENT

[75] Inventors: Gregory R. Reyes, Palo Alto; Patrice O. Yarbough, Redwood City, both of Calif.; Daniel W. Bradley, Lawrenceville; Krzysztof Z. Krawczynski, Tucker, both of Ga.; Albert Tam, San Francisco; Kirk E. Fry, Palo Alto, both of Calif.

[73] Assignee: Genelabs Technologies, Inc., Redwood City, Calif.

[21] Appl. No.: 279,823

[22] Filed: Jul. 25, 1994

Related U.S. Application Data

[63] Continuation of Ser. No. 681,078, Apr. 5, 1991, abandoned, which is a continuation-in-part of Ser. No. 505,888, Apr. 5, 1990, abandoned, which is a continuation-in-part of Ser. No. 420,921, Oct. 13, 1989, abandoned, which is a continuation-in-part of Ser. No. 367,486, Jun. 19, 1989, abandoned, which is a continuation-in-part of Ser. No. 336,672, Apr. 11, 1989, abandoned, which is a continuation-in-part of Ser. No. 208,997, Jun. 17, 1988, abandoned.

[51] Int. Cl.$^6$ .............................. C07H 21/04; C12Q 1/70; G01N 33/20; C12N 15/00

[52] U.S. Cl. ........................ 536/23.72; 536/24.32; 435/5; 435/6; 435/252.33; 435/320.1; 436/94; 935/1; 935/8; 935/66; 935/73

[58] Field of Search ...................... 435/5, 6, 91.1, 435/91.2, 320.1, 252.3, 252.33; 536/23.72, 24.32; 935/76–78, 1, 10, 22, 8, 66, 73; 436/94

[56] References Cited

U.S. PATENT DOCUMENTS

| | | | |
|---|---|---|---|
| 4,659,678 | 4/1987 | Forrest et al. | 436/512 |
| 4,683,195 | 7/1987 | Mullis et al. | 435/6 |
| 4,871,659 | 10/1989 | Pillot | 435/5 |
| 5,077,193 | 12/1991 | Mishiro et al. | 435/5 |

FOREIGN PATENT DOCUMENTS

| | | | |
|---|---|---|---|
| 2 606 515 | 5/1988 | France. | |
| 2 609 807 | 6/1988 | France. | |
| 85/01517 | 4/1985 | WIPO. | |
| 88/03410 | 5/1988 | WIPO. | |
| 89/12641 | 12/1989 | WIPO. | |
| 8912641 | 12/1989 | WIPO | C07H 17/00 |

OTHER PUBLICATIONS

New Enbland Bio Labs 1988–1989 Catalog, p. 62.
Lewin, R., "When Does Homology Mean Something Else?", *Science*, vol. 237, Sep. 1987, p. 1570.
Sarthou, et al., "Characterization of an antigen–antibody system associated associated with epidimic non–A, non–B hepatitis in West Africa . . . " Ann. Inst. Pasteur/Virl., 137: 225–232 (1986).
Sigma Chemical Company, "Sigma Price List 1987", p. 1024, (1987).
Computer generated sequence comparison—source: Gen-Bank.

*Primary Examiner*—Bradley L. Sisson
*Attorney, Agent, or Firm*—Charles K. Sholtz; Gary R. Fabian; Peter J. Dehlinger

[57] ABSTRACT

Nucleic acid sequences derived from enterically transmitted nonA/nonB viral hepatitis agent (HEV) are disclosed. DNA sequences encoding specific epitopes within viral protein sequences that are reactive with sera of individuals infected with different strains of HEV are also disclosed. These DNA sequences and fragments thereof are useful for identifying and sequencing the entire viral agent and for assaying the presence of the viral agent in an infected sample, for example by using specific amplification of virus-derived DNA sequences, as well as for producing viral proteins or polypeptides.

8 Claims, 2 Drawing Sheets

DNA SEQUENCES OF ENTERICALLY TRANSMITTED NON-A/NON-B HEPATITIS VIRAL AGENT

CROSS-REFERENCE TO RELATED APPLICATIONS

This application is a continuation of U.S. application Ser. No. 07/681,078, filed 5 Apr., 1991, now abandoned, which is a continuation-in-part of U.S. application Ser. No. 07/505,888, filed Apr. 5, 1990, now abandoned, which is a continuation-in-part of U.S. application Ser. No. 07/420,921, filed Oct. 13, 1989, now abandoned, which is a continuation-in-part of U.S. application Ser. No. 07/367,486, filed Jun. 16, 1989, now abandoned, which is a continuation-in-part of U.S. application Ser. No. 07/336,672, filed Apr. 11, 1989, now abandoned, which is a continuation-in-part of U.S. application Ser. No 07/208,997, filed Jun. 17, 1988, now abandoned, all of which are herein incorporated by reference.

FIELD OF INVENTION

This invention relates to recombinant proteins, genes, and gene probes and more specifically to such proteins and probes derived from an enterically transmitted nonA/nonB hepatitis viral agent, to diagnostic methods and vaccine applications which employ the proteins and probes, and to gene segments that encode specific epitopes (and proteins artificially produced to contain those epitopes) that are particularly useful in diagnosis and prophylaxis.

BACKGROUND

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although the virus may also spread by close physical contact. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%.

This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

There have been major efforts worldwide to identify and clone viral genomic sequences associated with ET-NANB hepatitis. One goal of this effort, requiring virus-specific genomic sequences, is to identify and characterize the nature of the virus and its protein products. Another goal is to produce recombinant viral proteins which can be used in antibody-based diagnostic procedures and for a vaccine. Despite these efforts, viral sequences associated with ET-NANB hepatitis have not been successfully identified or cloned heretofore, nor have any virus-specific proteins been identified or produced.

RELEVANT LITERATURE

Arankalle, V. A., et al., The Lancet, 550 (Mar. 12, 1988).
Bradley, D. W., et al., J Gen. Virol., 69:1 (1988).
Bradley, D. W. et al., Proc. Nat. Acad. Sci., USA, 84:6277 (1987).
Gravelle, C. R. et al., J. Infect. Diseases, 131:167 (1975).
Kane, M. A., et al., JAMA, 252:3140 (1984).
Khuroo, M. S., Am. J. Med., 48:818 (1980).
Khuroo, M. S., et al., Am. J. Med., 68:818 (1983).
Maniatis, T., et al. Molecular Cloning: A Laboratory Manual, Cold Spring Harbor Laboratory (1982).
Seto, B., et al., Lancet, 11:941 (1984).
Sreenivasan, M. A., et al., J. Gen. Virol., 65:1005 (1984).
Tabor, E., et al., J. Infect. Dis., 140:789 (1979).

SUMMARY OF THE INVENTION

Novel compositions, as well as methods of preparation and use of the compositions are provided, where the compositions comprise viral proteins and fragments thereof derived from the viral agent for ET-NANB. A number of specific fragments of viral proteins (and the corresponding genetic sequences) that are particularly useful in diagnosis and vaccine production are also disclosed. Methods for preparation of ET-NANB viral proteins include isolating ET-NANB genomic sequences which are then cloned and expressed in a host cell. The resultant recombinant viral proteins find use as diagnostic agents and as vaccines. The genomic sequences and fragments thereof find use in preparing ET-NANB viral proteins and as probes for virus detection.

DESCRIPTION OF SPECIFIC EMBODIMENTS

Figure 1:
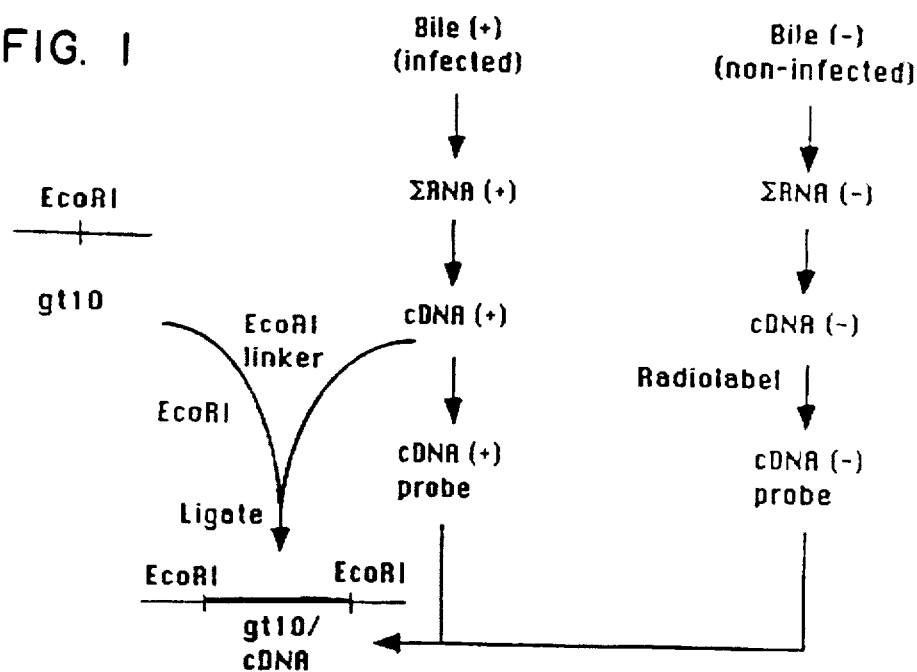
FIG. 1 shows vector constructions and manipulations used in obtaining and sequencing cloned ET-NANB fragment.
Figure 1:
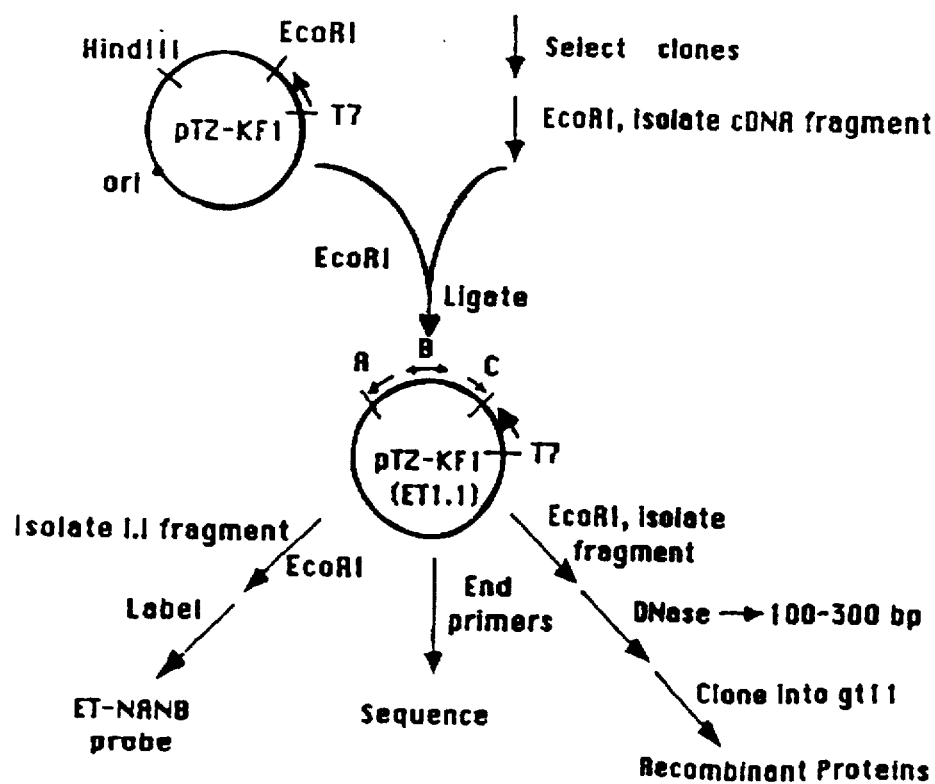

Novel compositions comprising generic sequences and fragments thereof derived from the viral agent for ET-NANB are provided, together with recombinant viral proteins produced using the genomic sequences and methods of using these compositions. Epitopes on the viral protein have been identified that are particularly useful in diagnosis and vaccine production. Small peptides containing the epitopes are recognized by multiple sera of patients infected with ET-NANB.

The molecular cloning of HEV was accomplished by two very different approaches. The first successful identification of a molecular clone was based on the differential hybridization of putative HEV cDNA clones to heterogeneous cDNA from infected and uninfected cyno bile. cDNAs from both sources were labeled to high specific activity with $^{32}P$ to identify a clone that hybridized specifically to the infected source probe. A cyno monkey infected with the Burma isolate of HEV was used in these first experiments. The sensitivity of this procedure is directly related to the relative abundance of the specific sequence against the overall background. In control experiments, it was found that specific identification of a target sequence may be obtained with as little as 1 specific part per 1000 background sequences. A number of clones were identified by this procedure using libraries and probes made from infected (Burma isolate) and control uninfected cyno bile. The first extensively characterized clone of the 16 plaques purified by this protocol was given the designation ET1.1.

ET1.1 was first characterized as both derived from and unique to the infected source cDNA. Heterogeneous cDNA was amplified from both infected and uninfected sources using a sequence independent single premier amplification technique (SISPA). This technique is described in copending application Ser. No. 208,512, filed Jun. 17, 1988. The limited pool of cDNA made from Burma infected cyno bile could then be amplified enzymatically prior to cloning or hybridization using putative HEV clones as probes. ET1.1 hybridized specifically to the original bile cDNA from the infected source. Further validation of this clone as derived from the genome of HEV was demonstrated by the similarity of the ET1.1 sequence and those present in SISPA cDNA prepared from five different human stool samples collected from different ET-NANBH epidemics including Somalia, Tashkent, Borneo, Mexico and Pakistan. These molecular epidemiologic studies established the isolated sequence as derived from the virus that represented the major cause of ET-NANBH worldwide.

The viral specificity of ET1.1 was further established by the finding that the clone hybridized specifically to RNA extracted from infected cyno liver. Hybridization analysis of polyadenylated RNA demonstrated a unique 7.5 Kb polyadenylated transcript not present in uninfected liver. The size of this transcript suggested that it represented the full length viral genome. Strand specific oligonucleotides were also used to probe viral genomic RNA extracted directly from semi-purified virions prepared from human stool. The strand specificity was based on the RNA-directed RNA polymerase (RDRP) open reading frame (ORF) identified in ET1.1 (see below). Only the probe detecting the sense strand hybridized to the nucleic acid. These studies characterized HEV as a plus sense, single stranded genome. Strand specific hybridization to RNA extracted from the liver also established that the vast majority of intracellular transcript was positive sense. Barring any novel mechanism for virus expression, the negative strand, although not detectable, would be present at a ratio of less than 1:100 when compared with the sense strand.

ET1.1 was documented as exogenous when tested by both Southern blot hybridization and PCR using genomic DNAs derived from uninfected humans, infected and uninfected cynos and also the genomic DNAs from *E. coli* and various bacteriophage sources. The latter were tested in order to rule out trivial contamination with an exogenous sequence introduced during the numerous enzymatic manipulations performed during cDNA construction and amplification. It was also found that the nucleotide sequence of the ET1.1 clone was not homologous to any entries in the Genebank database. The translated open reading frame of the ET1.1 clone did, however, demonstrate limited homology with consensus amino acid residues consistent with an RNA-directed RNA polymerase. This consensus amino acid motif is shared among all positive strand RNA viruses and, as noted above, is present at the 3' end of the HCV genome. The 1.3 Kb clone was therefore presumed to be derived, at least in part, from the nonstructural portion of the viral genome.

Because of the relationship of different strains of ET-NANB to each other that has been demonstrated by the present invention, the genome of the ET-NANB viral agent is defined in this specification as containing a region which is homologous to the 1.33 kb DNA EcoRI insert present in plasmid pTZKF1 (ET1.1) carried in *E. coli* strain BB4 and deposited at the American Type Culture Collection (ATCC; Rockville, Md.) on May 27, 1988 under Accession Number 67717. The viability of the deposit was established on Jun. 1, 1988. The entire sequence, in both directions, has now been identified as set forth below. The sequences of both strands are provided, since both strands can encode proteins. However, the sequence in one direction has been designated as the "forward" sequence because of statistical similarities to known proteins and because the forward sequence is known to be predominately protein-encoding. This sequence is set forth below along with the three possible translation sequences. There is one long open reading frame that starts at nucleotide 145 with an isoleucine and extends to the end of the sequence. The two other reading frames have many termination codons. Standard abbreviations for nucleotides and amino acids are used here and elsewhere in this specification.

The gene sequence is substantially identical to one given in the parent application. The present sequence differs in the omission of the first 37 nucleotides at the 5' end and last 13 nucleotides at the 3' end, which are derived from the linker used for cloning rather than from the virus. In addition, a G was omitted at position 227 of the sequence given in the parent application.

The gene sequence has SEQ ID NO.1; the first amino acid sequence in reading frame beginning with nucleotide 1 has SEQ ID NO.2.

The complementary strand, referred to here as the "reverse sequence," is set forth below in the same manner as the forward sequence set forth above. Several open reading frames, shorter than the long open reading frame found in the forward sequence, can be seen in this reverse sequence. Because of the relative brevity of the open reading frames in the reverse direction, they are probably not expressed.

The gene sequence has SEQ ID NO.5.

Identity of this sequence with sequences in etiologic agents has been confirmed by locating a corresponding sequence in a viral strain isolated in Burma. The Burmese isolate contains the following sequence of nucleotides (one strand and open reading frames shown). The gene sequence has SEQ ID NO.6; the protein sequence corresponding to ORF1 has SEQ ID NO.7; ORF2 has SEQ ID NO.8; and ORF3 has SEQ ID NO.9.

Total number of bases in the nucleotide sequence as presented is 7195. The poly-A tail present in the cloned sequence has been omitted.

The ability of the methods described herein to isolate and identify genetic material from other NANB hepatitis strains has been confirmed by identifying genetic material from an isolate obtained in Mexico. The sequence of this isolate was about 75% identical to the ET1.1 sequence set forth in SEQ ID NO.1 above. The sequence was identified by hybridization using the conditions set forth in Section II.B below.

In this different approach to isolation of the virus, cDNA libraries were made directly from a semi-purified human stool specimen collected from an outbreak of ET-NANB in Telixtac. The recovery of cDNA and the construction of representative libraries was assured by the application of sequence independent single premier amplification (SISPA). A cDNA library constructed in lambda gt11 from such an amplified cDNA population was screened with a serum considered to have "high" titer anti-HEV antibodies as assayed by direct immunofluorescence on liver sections from infected cynos. Two cDNA clones, denoted 406.3-2 and 406.4-2, were identified by this approach from a total of 60,000 screened. The sequence of these clones was subsequently localized to the 3' half of the viral genome by homology comparison to the HEV (Burma) sequence obtained from clones isolated by hybridization screening of libraries with the original ET1.1 clone.

These isolated cDNA epitopes when used as hybridization probes on Northern blots of RNA extracted from infected cyno liver gave a somewhat different result when compared to the Northern blots obtained with the ET1.1 probe. In addition to the single 7.5 Kb transcript seen using ET1.1, two additional transcripts of 3.7 and 2.0 Kb were identified using either of these epitopes as hybridization probes. These polyadenylated transcripts were identified using the extreme 3' end epitope clone (406.3-2) as probe and therefore established these transcripts as co-terminal with the 3' end of the genome (see below). One of the epitope clones (406.4-2) was subsequently shown to react in a specific fashion with antisera collected from 5 different geographic epidemics (Somalia, Burma, Mexico, Tashkent and Pakistan). The 406.3-2 clone reacted with sera from 4 out of these same 5 epidemics (Yarbough et al., 1990). Both clones reacted with only post inoculation antisera from infected cynos. The latter experiment confirmed that seroconversion in experimentally infected cynos was related to the isolated exogenous cloned sequence.

A composite cDNA sequence (obtained from several clones of the Mexican strain) is the Composite Mexico strain sequence (SEQ ID NO.10).

The sequence was obtained from polyadenylated clones. For clarity the 3' polyA "tail" has been omitted.

The sequence includes a partial cDNA sequence consisting of 1661 nucleotides that was identified in a previous application in this series. The previously identified partial sequence is set forth below, with certain corrections (SEQ ID NO.11). The corrections include deletion of the first 80 bases of the prior reported sequence, which are cloning artifacts; insertion of G after former position 174, of C after 270, and of GGCG after 279; change of C to T at former position 709, of GC to CG at 722–723, of CC to TT at 1238–39, and of C to G at 1606; deletion of T at former position 765; and deletion of the last 11 bases of the former sequence, which are part of a linker sequence and are not of viral origin.

When comparing the Burmese and Mexican strains, 75.7% identity is seen in a 7189 nucleotide overlap beginning at nucleotide 1 of the Mexican strain and nucleotide 25 of the Burmese strain.

In the same manner, a different strain of HEV was identified in an isolate obtained in Tashkent, U.S.S.R. The Tashkent sequence is given as (SEQ ID NO.12).

As shown in the following comparison of sequences, the Tashkent (Tash.) sequence more closely resembles the Burma sequence than the Mexico sequence, as would be expected of two strains from more closely related geographical areas. The numbering system used in the comparison is based on the Burma sequence. As indicated previously, Burma has SEQ ID NO:6; Mexico, SEQ ID NO:10; and Tashkent, SEQ ID NO:12. The letters present in the lines between the sequences indicate conserved nucleotides.

```
                      10v         20v         30v         40v         50v         60v
BURMA     AGGCAGACCACATATGTGGTCGATGCCATGGAGGCCCATCAGTTTATTAAGGCTCCTGGCA
                                  GCCATGGAGGCCCA CAGTT ATTAAGGCTCCTGGCA
MEXICO                            GCCATGGAGGCCCACCAGTTCATTAAGGCTCCTGGCA 70v         80v         90v         100v        110v        120v
BURMA     TCACTACTGCTATTGAGCAGGCTGCTCTAGCAGCGGCCAACTCTGCCCTGGCGAATGCTG
          TCACTACTGCTATTGAGCA GC GCTCTAGCAGCGGCCAACTC GCCCT GCGAATGCTG
MEXICO    TCACTACTGCTATTGAGCAAGCAGCTCTAGCAGCGGCCAACTCCGCCCTTGCGAATGCTG 130v        140v        150v        160v        170v        180v
BURMA     TGGTAGTTAGGCCTTTTCTCTCTCACCAGCAGATTGAGATCCTCATTAACCTAATGCAAC
          TGGT GT  GGCCTTT CT TC CA CAGCAG TTGAGATCCT AT AA CT ATGCAAC
MEXICO    TGGTGGTCCGGCCTTTCCTTTCCCATCAGCAGGTTGAGATCCTTATAAATCTCATGCAAC 190v        200v        210v        220v        230v        240v
BURMA     CTCGCCAGCTTGTTTTCCGCCCCGAGGTTTTCTGGAATCATCCCATCCAGCGTGTCATCC
          CTCG CAGCT GT TT CG CC GAGGTTTT TGGAATCA CC AT CA CGTGT AT C
MEXICO    CTCGGCAGCTGGTGTTTCGTCCTGAGGTTTTTTGGAATCACCCGATTCAACGTGTTATAC 250v        260v        270v        280v        290v        300v
BURMA     ATAACGAGCTGGAGCTTTACTGCCGCGCCCGCTCCGGCCGCTGTCTTGAAATTGGCGCCC
          ATAA GAGCT GAGC  TA TGCCG GC CGCTC GG CGCTG CTTGA ATTGG GCCC
MEXICO    ATAATGAGCTTGAGCAGTATTGCCGTGCTCGCTCGGGTCGCTGCCTTGAGATTGGAGCCC
```

-continued

```
              310v       320v       330v       340v       350v       360v
BURMA  ATCCCCGCTCAATAAATGATAATCCTAATGTGGTCCACCGCTGCTTCCTCCGCCCTGTTG
       A  CC CGCTC AT AATGATAATCCTAATGT  TCCA CGCTGCTT CTCC CCC GT G
MEXICO ACCCACGCTCCATTAATGATAATCCTAATGTCCTCCATCGCTGCTTTCTCCACCCCGTCG 370v       380v       390v       400v       410v       420v
BURMA  GGCGTGATGTTCAGCGCTGGTATACTGCTCCCACTCGCGGGCCGGCTGCTAATTGCCGGC
       G CG GATGTTCAGCGCTGGTA AC GC CC ACT G GG CC GC GC AA TG CG C
MEXICO GCCGGGATGTTCAGCGCTGGTACACAGCCCCGACTAGGGGACCTGCGGCGAACTGTCGCC 430v       440v       450v       460v       470v       480v
BURMA  GTTCCGCGCTGCGCGGGCTTCCCGCTGCTGACCGCACTTACTGCCTCGACGGGTTTTCTG
       G TC GC CT CG GG CT CC  C GC GACCGCACTTACTG  T GA GG TTT  C G
MEXICO GCTCGGCACTTCGTGGTCTGCCACCAGCCGACCGCACTTACTGTTTTGATGGCTTTGCCG 490v       500v       510v       520v       530v       540v
BURMA  GCTGTAACTTTCCCGCCGAGACTGGCATCGCCCTCTACTCCCTTCATGATATGTCACCAT
       GCTG    TTT CCGCCGAGACTGG  T GC CTCTA TC CT CATGA   TG    CC
MEXICO GCTGCCGTTTTGCCGCCGAGACTGGTGTGGCTCTCTATTCTCTCCATGACTTGCAGCCGG 550v       560v       570v       580v       590v       600v
BURMA  CTGATGTCGCCGAGGCCATGTTCCGCCATGGTATGACGCGGCTCTATGCCGCCCTCCATC
       CTGATGT GCCGAGGC ATG   CGCCA GG ATGAC CG CT TATGC GC  TCCA
MEXICO CTGATGTTGCCGAGGCGATGGCTCGCCACGGCATGACCCGCCTTTATGCAGCTTTCCACT 610v       620v       630v       640v       650v       660v
BURMA  TTCCGCCTGAGGTCCTGCTGCCCCCTGGCACATATCGCACCGCATCGTATTTGCTAATTC
       T CC CC GAGGT CT CTGCC CCTGGCAC TA CG AC  CATC TA TTGCT AT C
MEXICO TGCCTCCAGAGGTGCTCCTGCCTCCTGGCACCTACCGGACATCATCCTACTTGCTGATCC 670v       680v       690v       700v       710v       720v
BURMA  ATGACGGTAGGCGCGTTGTGGTGACGTATGAGGGTGATACTAGTGCTGGTTACAACCACG
       A GA GGTA GCGCG  GT GT AC TATGAGGGTGA ACTAG GC GGTTACAA CA G
MEXICO ACGATGGTAAGCGCGCGGTTGTCACTTATGAGGGTGACACTAGCGCCGGTTACAATCATG 730v       740v       750v       760v       770v       780v
BURMA  ATGTCTCCAACTTGCGCTCCTGGATTAGAACCACCAAGGTTACCGGAGACCATCCCCTCG
       ATGT    CCA C T CGC C TGGAT AG AC AC AAGGTT    GG GA CA CC  T G
MEXICO ATGTTGCCACCCTCCGCACATGGATCAGGACAACTAAGGTTGTGGGTGAACACCCTTTGG 790v       800v       810v       820v       830v       840v
BURMA  TTATCGAGCGGGTTAGGGCCATTGGCTGCCACTTTGTTCTCTTGCTCACGGCAGCCCCGG
       T ATCGAGCGGGT  GGG  ATTGGCTG CACTTTGT T TTG TCAC GC GCCCC G
MEXICO TGATCGAGCGGGTGCGGGGTATTGGCTGTCACTTTGTGTTGTTGATCACTGCGGCCCCTG 850v       860v       870v       880v       890v       900v
BURMA  AGCCATCACCTATGCCTTATGTTCCTTACCCCCGGTCTACCGAGGTCTATGTCCGATCGA
       AGCC TC CC ATGCC TA GTTCCTTACCC CG TC AC GAGGTCTATGTCCG TC A
MEXICO AGCCCTCCCCGATGCCCTACGTTCCTTACCCGCGTTCGACGGAGGTCTATGTCCGGTCTA 910v       920v       930v       940v       950v       960v
BURMA  TCTTCGGCCCGGGTGGCACCCCTTCCTTATTCCCAACCTCATGCTCCACTAAGTCGACCT
       TCTT GG CC GG GG  CCCC TC T TTCCC ACC C TG  C   AAGTC AC T
MEXICO TCTTTGGGCCCGGCGGGTCCCCGTCGCTGTTCCCGACCGCTTGTGCTGTCAAGTCCACTT 970v       980v       990v       1000v      1010v      1020v
BURMA  TCCATGCTGTCCCTGCCCATATTTGGGACCGTCTTATGCTGTTCGGGGCCACCTTGGATG
       T CA GC GTCCC  C CA AT TGGGACCGTCT ATGCT TT GGGGCCACC T GA G
MEXICO TTCACGCCGTCCCCACGCACATCTGGGACCGTCTCATGCTCTTTGGGGCCACCCTCGACG 1030v      1040v      1050v      1060v      1070v      1080v
BURMA  ACCAAGCCTTTTGCTGCTCCCGTTTAATGACCTACCTTCGCGGCATTAGCTACAAGGTCA
       ACCA  GCCTTTTGCTGCTCC  G  T ATGAC TACCTTCG GGCATTAGCTA AAGGT A
MEXICO ACCAGGCCTTTTGCTGCTCCAGGCTTATGACGTACCTTCGTGGCATTAGCTATAAGGTAA 1090v      1100v      1110v      1120v      1130v      1140v
BURMA  CTGTTGGTACCCTTGTGGCTAATGAAGGCTGGAATGCCTCTGAGGACGCCCTCACAGCTG
       CTGT  GGT  CCCT GT GCTAATGAAGGCTGGAATGCC  C GAGGA GC CTCAC GC G
MEXICO CTGTGGGTGCCCTGGTCGCTAATGAAGGCTGGAATGCCACCGAGGATGCGCTCACTGCAG 1150v      1160v      1170v      1180v      1190v      1200v
BURMA  TTATCACTGCCGCCTACCTTACCATTTGCCACCAGCGGTATCTCCGCACCCAGGCTATAT
       TTAT AC GC GC TACCT AC AT TG CA CAGCG TAT T CG ACCCAGGC AT T
MEXICO TTATTACGGCGGCTTACCTCACAATATGTCATCAGCGTTATTTGCGGACCCAGGCGATTT 1210v      1220v      1230v      1240v      1250v      1260v
BURMA  CCAAGGGGATGCGTCGTCTGGAACGGGAGCATGCCCAGAAGTTTATAACACGCCTCTACA
       C AAGGG ATGCG CG CT GA C  GA CATGC CAGAA TTTAT  CACGCCTCTACA
MEXICO CTAAGGGCATGCGCCGGCTTGAGCTTGAACATGCTCAGAAATTTATTTCACGCCTCTACA
```

-continued

```
              1270v        1280v        1290v        1300v        1310v        1320v
BURMA    GCTGGCTCTTCGAGAAGTCCGGCCGTGATTACATCCCTGGCCGTCAGTTGGAGTTCTACG
         GCTGGCT  TT GAGAAGTC  GG CGTGATTACATCCC GGCCG CAG TG AGTTCTACG
MEXICO   GCTGGCTATTTGAGAAGTCAGGTCGTGATTACATCCCAGGCCGCCAGCTGCAGTTCTACG 1330v        1340v        1350v        1360v        1370v        1380v
BURMA    CCCAGTGCAGGCGCTGGCTCTCCGCCGGCTTTCATCTTGATCCACGGGTGTTGGTTTTTG
         C CAGTGC  G CGCTGG T TC GCCGG TT CATCT GA CC CG   TT GTTTTTG
MEXICO   CTCAGTGCCGCCGCTGGTTATCTGCCGGGTTCCATCTCGACCCCCGCACCTTAGTTTTTG 1390v        1400v        1410v        1420v        1430v        1440v
BURMA    ACGAGTCGGCCCCCTGCCATTGTAGGACCGCGATCCGTAAGGCGCTCTCAAAGTTTTGCT
         A GAGTC  G  CC TG     TG  G ACC C ATCCG  G       AAA TTTTGCT
MEXICO   ATGAGTCAGTGCCTTGTAGCTGCCGAACCACCATCCGGCGGATCGCTGGAAAAATTTTGCT 1450v        1460v        1470v        1480v        1490v        1500v
BURMA    GCTTCATGAAGTGGCTTGGTCAGGAGTGCACCTGCTTCCTTCAGCCTGCAGAAGGCGCCG
         G TT ATGAAGTGGCT GGTCAGGAGTG  C TG TTCCT CAGCC GC GA GG    G
MEXICO   GTTTTATGAAGTGGCTCGGTCAGGAGTGTTCTTGTTTCCTCCAGCCCGCCGAGGGGCTGG 1510v        1520v        1530v        1540v        1550v        1560v
BURMA    TCGGCGACCAGGGTCATGATAATGAAGCCTATGAGGGGTCCGATGTTGACCCTGCTGAGT
            GGCGACCA GGTCATGA AATGA GCCTATGA GG TC GATGTTGA CTGCTGAG
MEXICO   CGGGCGACCAAGGTCATGACAATGAGGCCTATGAAGGCTCTGATGTTGATACTGCTGAGC 1570v        1580v        1590v        1600v        1610v        1620v
BURMA    CCGCCATTAGTGACATATCTGGGTCCTATGTCGTCCCTGGCACTGCCCTCCAACCGCTCT
         C GCCA       GACAT  C GG TC TA  TCGT    TGG    C CT CAA C  TCT
MEXICO   CTGCCACCCTAGACATTACAGGCTCATACATCGTGGATGGTCGGTCTCTGCAAACTGTCT 1630v        1640v        1650v        1660v        1670v        1680v
BURMA    ACCAGGCCCTCGATCTCCCCGCTGAGATTGTGGCTCGCGGGCCGGCTGACCGCCACAG
         A  CA GC CTCGA CT CC GCTGA   T GT GCTCGCGC G CCG CTG C GC ACAG
MEXICO   ATCAAGCTCTCGACCTGCCAGCTGACCTGGTAGCTCGCGCAGCCCGACTGTCTGCTACAG 1690v        1700v        1710v        1720v        1730v        1740v
BURMA    TAAAGGTCTCCCAGGTCGATGGGCGGATCGATTGCGGAGACCCTTCTTGGTAACAAAACCT
         T A GT  C  A   C  TGG CG  T GATTGC  A AC   T  T GG AA AA AC T
MEXICO   TTACTGTTACTGAAACCTCTGGCCGTCTGGATTGCCAAACAATGATCGGCAATAAGACTT 1750v        1760v        1770v        1780v        1790v        1800v
BURMA    TTCGCACGTCGTTCGTTGACGGGGCGGTCTTAGAGACCAATGGCCCAGAGCGCCACAATC
         TTC CAC   C TT GTTGA GGGGC   C T GAG   AA GG CC GAGC  C  AA C
MEXICO   TTCTCACTACCTTTGTTGATGGGGCACGCCTTGAGGTTAACGGGCCTGAGCAGCTTAACC 1810v        1820v        1830v        1840v        1850v        1860v
BURMA    TCTCCTTCGATGCCAGTCAGAGCACTATGGCCGCTGGCCCTTTCAGTCTCACCTATGCCG
         TCTC TT GA   C   CAG G A TATGGC GC GGCCC TT  G CTCACCTATGC G
MEXICO   TCTCTTTTGACAGCCAGCAGTGTAGTATGGCAGCCGGCCCGTTTTGCCTCACCTATGCTG 1870v        1880v        1890v        1900v        1910v        1920v
BURMA    CCTCTGCAGCTGGGCTGGAGGTGCGCTATGTTGCTGCCGGGCTTGACCATCGGGCGGTTT
         CC    G  G  GGGCTGGA GT C  T T     C GC GG CT GA   CG G GTTT
MEXICO   CCGTAGATGGCGGGCTGGAAGTTCATTTTTCCACCGCTGGCCTCGAGAGCCGTGTTGTTT 1930v        1940v        1950v        1960v        1970v        1980v
BURMA    TTGCCCCCGGTGTTTCACCCCGGTCAGCCCCCGGCGAGGTTACCGCCTTCTGCTCTGCCC
         T CCCC GGT  T C CC     C  C CC   G GAGGT ACCGCCTTCTGCTC GC C
MEXICO   TCCCCCCTGGTAATGCCCCGACTGCCCCGCCGAGTGAGGTCACCGCCTTCTGCTCAGCTC 1990v        2000v        2010v        2020v        2030v        2040v
BURMA    TATACAGGTTTAACCGTGAGGCCCAGCGCGCCATTCGTGATCGGTAACTTATGGTTCCATC
         T TA AGG    AACCG  AG  CCAGCGCCA TCG T AT GGTA  TT TGG T CA C
MEXICO   TTTATAGGCACAACCGGCAGAGCCAGCGCCAGTCGGTTATTGGTAGTTTGTGGCTGCACC 2050v        2060v        2070v        2080v        2090v        2100v
BURMA    CTGAGGGACTCATTGGCCTCTTCGCCCCGTTTTCGCCCGGGCATGTTTGGGAGTCGGCTA
         CTGA GG  T  T GGCCT TTC C CC TTTTC CCCGGGCATG  TGG  GTC GCTA
MEXICO   CTGAAGGTTTGCTCGGCCTGTTCCCGCCCTTTTCACCCGGGCATGAGTGGCGGTCTGCTA 2110v        2120v        2130v        2140v        2150v        2160v
BURMA    ATCCATTCTGTGGCGAGAGCACACTTTACACCCGTACTTGGTCGGAGGTTGATGCCGTCT
         A CCATT TG GGCGAGAGCAC CT TACACCCG ACTTGGTC      TT    G C
MEXICO   ACCCATTTTGCGGCGAGAGCACGCTCTACACCCGCACTTGGTCCACAATTACAGACACAC 2170v        2180v        2190v        2200v        2210v        2220v
BURMA    CTAGTCCAGCCCGGCCTGACTTAGGTTTTATGTCTGAGCCTTCTATACCTAGTAGGGCCG
         C    CG C GGC    T  GGT  T TG  TG  CT C      C  G GG C
MEXICO   CCTTAACTGTCGGGCTAATTTCCGGTCATTTGGATGCTGCTCCCCACTCGGGGGGGCCAC
```

-continued

```
                  2230v       2240v       2250v       2260v       2270v       2280v
BURMA   CCACGCCTACCCTGGCGGCCCCTCTACCCCCCCCTGCACCGGACCCTTCCCCCCCTCCCT
        C  C  CT CC    G    C  CT TA  C C   CTG    C         C   CCC C
MEXICO  CTGCTACTGCCACAGGCCCTGCTGTAGGCTCGTCTGACTCTCCAGACCCTGACCCGCTAC 2290v       2300v       2310v       2320v       2330v       2340v
BURMA   CTGCCCCGGCGCTTGCTGAGCCGGCCTTCTGGCGCTACCGCCGGGGCCCCGGCCATAACTC
        CTG    C    TG   C    C TCTGG GC      C G  G CCC    C    A T
MEXICO  CTGATGTTACAGATGGCTCACGCCCCTCTGGGGCCCGTCCGGCTGGCCCCAACCCGAATG 2350v       2360v       2370v       2380v       2390v       2400v
BURMA   ACCAGACGGCCCGGCACCGCCGCCTGCTCTTCACCTACCCGGATGGCTCTAAGGTATTCG
        C   CG         CGCCGC T CT    CACCTACCC GA GGC CTAAG T T    G
MEXICO  GCGTTCCGCAG------CGCCGCTTACTACACACCTACCCTGACGGCGCTAAGATCTATG 2410v       2420v       2430v       2440v       2450v       2460v
BURMA   CCGGCTCGCTGTTCGAGTCGACATGCACGTGGCTCGTTAACGCGTCTAATGTTGACCACC
           CGGCTC  T TTCGAGTC     TGCAC TGGCT GT AACGC TCTAA G  G CCACC
MEXICO  TCGGCTCCATTTTCGAGTCTGAGTGCACCTGGCTTGTCAACGCATCTAACGCCGGCCACC 2470v       2480v       2490v       2500v       2510v       2520v
BURMA   GCCCTGGCGGCGGGCTTTGCCATGCATTTTACCAAAGGTACCCCGCCTCCTTTGATGCTG
        GCCCTGG GGCGGGCTTTG CATGC TTTT  CA  G TACCC G  TC TTTGA GC
MEXICO  GCCCTGGTGGCGGGCTTTGTCATGCTTTTTTTCAGCGTTACCCTGATTCGTTTGACGCCA 2530v       2540v       2550v       2560v       2570v       2580v
BURMA   CCTCTTTTGTGATGCGCGACGGCGCGGCCGCGTACACACTAACCCCCCGGCCAATAATTC
        CC   TTTGTGATGCG GA GG    GCCGCGTA AC CT AC CCCCGGCC AT ATTC
MEXICO  CCAAGTTTGTGATGCGTGATGGTCTTGCCGCGTATACCCTTACACCCCGGCCGATCATTC 2590v       2600v       2610v       2620v       2630v       2640v
BURMA   ACGCTGTCGCCCCTGATTATAGGTTGGAACATAACCCAAAGAGGCTTGAGGCTGCTTATC
        A  GC GT GCCCC GA TAT G TTGGAACATAACCC AAGAGGCT GAGGCTGC TA C
MEXICO  ATGCGGTGGCCCCGGACTATCGATTGGAACATAACCCCAAGAGGCTCGAGGCTGCCTACC 2650v       2660v       2670v       2680v       2690v       2700v
BURMA   GGGAAACTTGCTCCCGCCTCGGCACCGCTGCATACCCGCTCCTCGGGACCGGCATATACC
        G GA ACTTGC CCCGCC  GGCAC GCTGC TA CC CTC T GG  C GGCAT TACC
MEXICO  GCGAGACTTGCGCCCGCCGAGGCACTGCTGCCTATCCACTCTTAGGCGCTGGCATTTACC 2710v       2720v       2730v       2740v       2750v       2760v
BURMA   AGGTGCCGATCGGCCCCAGTTTTGACGCCTGGGAGCGGAACCACCGCCCCGGGGATGAGT
        AGGTGCC   T  G   AGTTTTGA GCCTGGGAGCGGAACCACCGCCC    GA GAG
MEXICO  AGGTGCCTGTTAGTTTGAGTTTTGATGCCTGGGAGCGGAACCACCGCCCGTTTGACGAGC 2770v       2780v       2790v       2800v       2810v       2820v
BURMA   TGTACCTTCCTGAGCTTGCTGCCAGATGGTTTGAGGCCAATAGGCCGACCCGCCCGACTC
        T  TACCT  C GAGCT GC GC  G TGGTTTGA  CCAA  G CC    C  CC AC
MEXICO  TTTACCTAACAGAGCTGGCGGCTCGGTGGTTTGAATCCAACCGCCCCGGTCAGCCCACGT 2830v       2840v       2850v       2860v       2870v       2880v
BURMA   TCACTATAACTGAGGATGTTGCACGGACAGCGAATCTGGCCATCGAGCTTGACTCAGCCA
        T  A  ATAACTGAGGAT   GC CG  C GC AA CTGGCC T GAGCTTGACTC G A
MEXICO  TGAACATAACTGAGGATACCGCCCGTGCGGCCAACCTGGCCCTGGAGCTTGACTCCGGGA 2890v       2900v       2910v       2920v       2930v       2940v
BURMA   CAGATGTCGGCCGGGCCTGTGCCGGCTGTCGGGTCACCCCCGGCGTTGTTCAGTACCAGT
           GA GT GGCCG GC TGTGCCGG TGT    GTC    CC GGCGTTGT C GTA CAGT
MEXICO  GTGAAGTAGGCCGCGCATGTGCCGGGTGTAAAGTCGAGCCTGGCGTTGTGCGGTATCAGT 2950v       2960v       2970v       2980v       2990v       3000v
BURMA   TTACTGCAGGTGTGCCTGGATCCGGCAAGTCCCGCTCTATCACCCAAGCCGATGTGGACG
        TTAC GC GGTGT CC GG TC GGCAAGTC     TC  T     CA GC GATGTGGA G
MEXICO  TTACAGCCGGTGTCCCCGGCTCTGGCAAGTCAAAGTCCGTGCAACAGGCGGATGTGGATG 3010v       3020v       3030v       3040v       3050v       3060v
BURMA   TTGTCGTGGTCCCGACGCGTGAGTTGCGTAATGCCTGGCGCCGTCGCGGCTTTGCTGCTT
        TTGT GT GT CC AC CG GAG T CG AA GC TGGCG CG CG GGCTTTGC GC T
MEXICO  TTGTTGTTGTGCCCACTCGCGAGCTTCGGAACGCTTGGCGGCGCCGGGGCTTTGCGGCAT 3070v       3080v       3090v       3100v       3110v       3120v
BURMA   TTACCCCGCATACTGCCGCCAGAGTCACCCAGGGGCGCCGGGTTGTCATTGATGAGGCTC
        T  AC  CCGCA ACTGC GCC  G GTCAC     GG CG  GGGTTGTCATTGATGAGGC C
MEXICO  TCACTCCGCACACTGCGGCCCGTGTCACTAGCGGCCGTAGGGTTGTCATTGATGAGGCCC 3130v       3140v       3150v       3160v       3170v       3180v
BURMA   CATCCCTCCCCCCTCACCTGCTGCTGCTCCACATGCAGCGGGCCGCCACCGTCCACCTTC
        C  TC CTCCCCCC  CAC TGCTGCT  T CA ATGCAGCG GC GC   C GT CACCT C
MEXICO  CTTCGCTCCCCCCACACTTGCTGCTTTTACATATGCAGCGTGCTGCATCTGTGCACCTCC
```

-continued

```
              3190v      3200v      3210v      3220v      3230v      3240v
BURMA   TTGGCGACCCGAACCAGATCCCAGCCATCGACTTTGAGCACGCTGGGCTCGTCCCCGCCA
        TTGG GACCCGAA  CAGATCCC GCCAT GA TTTGAGCAC C GG CT  T  CC GC A
MEXICO  TTGGGGACCCGAATCAGATCCCCGCCATAGATTTTGAGCACACCGGTCTGATTCCAGCAA 3250v      3260v      3270v      3280v      3290v      3300v
BURMA   TCAGGCCCGACTTAGGCCCCACCTCCTGGTGGCATGTTACCCATCGCTGGCCTGCGGATG
        T  GGCC GA TT G CCC AC TC TGGTGGCATGT ACCCA CG TG CCTGC GATG
MEXICO  TACGGCCGGAGTTGGTCCCGACTTCATGGTGGCATGTCACCCACCGTTGCCCTGCAGATG 3310v      3320v      3330v      3340v      3350v      3360v
BURMA   TATGCGAGCTCATCCGTGGTGCATACCCCATGATCGAGACCACTAGCCGGGTTCTCCGTT
        T TG GAG T  TCCGTGGTGC TACCC A  ATCCAGAC AC AG   GGT CTCCGTT
MEXICO  TCTGTGAGTTAGTCCGTGGTGCTTACCCTAAAATCCAGACTACAAGTAAGGTGCTCCGTT 3370v      3380v      3390v      3400v      3410v      3420v
BURMA   CGTTGTTCTGGGGTGAGCCTGCCGTCGGGCAGAAACTAGTGTTCACCCAGGCGGCCAAGC
        C  T  TTCTGGGG GAGCC GC GTCGG CAGAA CTAGTGTTCAC CAGGC GC AAG
MEXICO  CCCTTTTCTGGGGAGAGCCAGCTGTCGGCCAGAAGCTAGTGTTCACACAGGCTGCTAAGG 3430v      3440v      3450v      3460v      3470v      3480v
BURMA   CCGCCAACCCCGGCTCAGTGACGGTCCACGAGGCGCAGGGCGCTACCTACACGGAGACCA
        CCGC  ACCCCGG TC  T ACGGTCCA GAGGC CAGGG GC AC T  AC   AC A
MEXICO  CCGCGCACCCCGGATCTATAACGGTCCATGAGGCCCAGGGTGCCACTTTTACCACTACAA 3490v      3500v      3510v      3520v      3530v      3540v
BURMA   CTATTATTGCCACAGCAGATGCCCGGGGCCTTATTCAGTCGTCTCGGGCTCATGCCATTG
        CTAT ATTGC AC GCAGATGCCCG GGCCT AT CAGTC TC CGGGCTCA GC AT G
MEXICO  CTATAATTGCAACTGCAGATGCCCGTGGCCTCATACAGTCCTCCCGGGCTCACGCTATAG 3550v      3560v      3570v      3580v      3590v      3600v
BURMA   TTGCTCTGACGCGCCACACTGAGAAGTGCGTCATCATTGACGCACCAGGCCTGCTTCGCG
        TTGCTCT AC   G CA ACTGA AA TG GT AT   TTGAC C  CC GGCCTG T CG G
MEXICO  TTGCTCTCACTAGGCATACTGAAAAATGTGTTATACTTGACTCTCCCGGCCTGTTGCGTG 3610v      3620v      3630v      3640v      3650v      3660v
BURMA   AGGTGGGCATCTCCGATGCAATCGTTAATAACTTTTTCCTCGCTGGTGGCGAAATTGGTC
        AGGTGGG ATCTC GATGC AT GTTAATAA TT TTCCT  C GGTGGCGA  TTGGTC
MEXICO  AGGTGGGTATCTCAGATGCCATTGTTAATAATTTCTTCCTTTCGGGTGGCGAGGTTGGTC 3670v      3680v      3690v      3700v      3710v      3720v
BURMA   ACCAGCGCCCATCAGTTATTCCCCGTGGCAACCCTGACGCCAATGTTGACACCCTGGCTG
        ACCAG G CCATC GT ATTCC CG GGCAACCCTGAC  CAATGTTGAC   CT GC G
MEXICO  ACCAGAGACCATCGGTCATTCCGCGAGGCAACCCTGACCECAATGTTGACGTGCTTGCGG 3730v      3740v      3750v      3760v      3770v      3780v
BURMA   CCTTCCCGCCGTCTTGCCAGATTAGTGCCTTCCATCAGTTGGCTGAGGAGCTTGGCCACA
        C  TT CC CC TC TGCCA AT AG GCCTTCCATCAG T GCTGAGGAGCT GGCCAC
MEXICO  CGTTTCCACCTTCATGCCAAATAAGCGCCTTCCATCAGCTTGCTGAGGAGCTGGGCCACC 3790v      3800v      3810v      3820v      3830v      3840v
BURMA   GACCTGTCCCTGTTGCAGCTGTTCTACCACCCTGCCCCGAGCTCGAACAGGGCCTTCTCT
        G CC G  CC GT GC GCTGT CTACC CCCTGCCC GAGCT GA CAGGGCCTTCTCT
MEXICO  GGCCGGCGCCGGTGGCGGCTGTGCTACCTCCCTGCCCTGAGCTTGAGCAGGGCCTTCTCT 3850v      3860v      3870v      3880v      3890v      3900v
BURMA   ACCTGCCCCAGGAGCTCACCACCTGTGATAGTGTCGTAACATTTGAATTAACAGACATTG
        A  CTGCC CAGGAGCT  CC CCTGTGA AGTGT GT ACATTTGA  TAAC GACATTG
MEXICO  ATCTGCCACAGGAGCTAGCCTCCTGTGACAGTGTTGTGACATTTGAGCTAACTGACATTG 3910v      3920v      3930v      3940v      3950v      3960v
BURMA   TGCACTGCCGCATGGCCGCCCCGAGCCAGCGCAAGGCCGTGCTGTCCACACTCGTGGGCC
        TGCACTGCCGCATGGC GCCCC AGCCA  G AA GC GT  TGTCCAC CT GT GGCC
MEXICO  TGCACTGCCGCATGGCGGCCCCTAGCCAAAGGAAAGCTGTTTTGTCCACGCTGGTAGGCC 3970v      3980v      3990v      4000v      4010v      4020v
BURMA   GCTACGGCGGTCGCACAAAGCTCTACAATGCTTCCCACTCTGATGTTCGCGACTCTCTCG
        G TA GGC G CGCACAA GCT TA ATGC   CAC C GATGT CGCG CTG CT G
MEXICO  GGTATGGCAGACGCACAAGGCTTTATGATGCGGGTCACACCGATGTCCGCGCCTCCCTTG 4030v      4040v      4050v      4060v      4070v      4080v
TASHKENT                         GGCCCCGTACAGGTCACAACCTGTGAGTTGTACGAGCTAG
                                 GGCCCCGTACAGGT ACAAC TGTGA TTGTACGAGCTAG
BURMA   CCCGTTTTATCCCGGCCATTGGCCCCGTACAGGTTACAACTTGTGAATTGTACGAGCTAG
        C  CG TTTAT CC  C  T GG C  GT    G AC AC TGTGAA T T GAGCT G
MEXICO  CGCGCTTTATTCCCACTCTCGGGCGGGTTACTGCCACCACCTGTGAACTCTTTGAGCTTG
```

-continued

```
           4090v      4100v      4110v      4120v      4130v      4140v
TASHKENT  TGGAGGCCATGGTCGAGAAAGGCCAGGATGGCTCCGCCGTCCTTGAGCTCGATCTCTGCA
          TGGAGGCCATGGTCGAGAA  GGCCAGGATGGCTCCGCCGTCCTTGAGCT GATCT TGCA
BURMA     TGGAGGCCATGGTCGAGAAGGGCCAGGATGGCTCCGCCGTCCTTGAGCTTGATCTTTGCA
          T GAGGC ATGGT GAGAAGGGCCA GA GG TC GCCGTCCT GAG T GAT T TGCA
MEXICO    TAGAGGCGATGGTGGAGAAGGGCCAAGACGGTTCAGCCGTCCTCGAGTTGGATTTGTGCA 4150v      4160v      4170v      4180v      4190v      4200v
TASHKENT  ACCGTGACGTGTCCAGGATCACCTTTTTCCAGAAAGATTGCAATAAGTTCACCACGGGAG
          ACCGTGACGTGTCCAGGATCACCTT TTCCAGAAAGATTG AA AAGTTCACCAC GG G
BURMA     ACCGTGACGTGTCCAGGATCACCTTCTTCCAGAAAGATTGTAACAAGTTCACCACAGGTG
          CCG GA GT TCC G AT ACCTT TTCCAGAA GATTGTAACAAGTTCAC AC GG G
MEXICO    GCCGAGATGTCTCCCGCATAACCTTTTTCCAGAAGGATTGTAACAAGTTCACGACCGGCG 4210v      4220v      4230v      4240v      4250v      4260v
TASHKENT  AGACCATCGCCCATGGTAAAGTGGGCCAGGGCATTTCGGCCTGGAGTAAGACCTTCTGTG
          AGACCAT GCCCATGGTAAAGTGGGCCAGGGCATTTCGGCCTGGAG AAGACCTTCTG G
BURMA     AGACCATTGCCCATGGTAAAGTGCCCAGGGCATCTCGGCCTGGAACAAGACCTTCTGCG
          AGAC ATTGC CATGG AAAGT GG CAGGG ATCT    CTGGAG AAGAC TT TG G
MEXICO    AGACAATTGCGCATGGCAAAGTCGGTCAGGGTATCTTCCGCTGGAGTAAGACGTTTTGTG 4270v      4280v      4290v      4300v      4310v      4320v
TASHKENT  CCCTTTTCGGCCCCTGGTTCCGTGCTATTGAGAAGGCTATTCTGGCCCTGCTCCCTCAGG
          CCCT TT GGCCC TGGTTCCG GCTATTGAGAAGGCTATTCTGGCCCTGCTCCCTCAGG
BURMA     CCCTCTTTGGCCCTTGGTTCCGCGCTATTGAGAAGGCTATTCTGGCCCTGCTCCCTCAGG
          CCCT TTTGGCCC TGGTTCCG GC ATTGAGAAGGCTATTCT  CCCT  T CC CA G
MEXICO    CCCTGTTTGGCCCCTGGTTCCGTGCGATTGAGAAGGCTATTCTATCCCTTTTACCACAAG 4330v      4340v      4350v      4360v      4370v      4380v
TASHKENT  GTGTGTTTTATGGGGATGCCTTTGATGACACCGTCTTCTCGGCGCGTGTGGCCGCAGCAA
          GTGTGTTTTA GG GATGCCTTTGATGACACCGTCTTCTCGGCG TGTGGCCGCAGCAA
BURMA     GTGTGTTTTACGGTGATGCCTTTGATGACACCGTCTTCTCGGCGGCTGTGGCCGCAGCAA
          TGTGTT TACGG GATGC T TGA GAC C GT TTCTC GC GC GTGGC G GC A
MEXICO    CTGTGTTCTACGGGGATGCTTATGACGACTCAGTATTCTCTGCTGCCGTGGCTGGCGCCA 4390v      4400v      4410v      4420v      4430v      4440v
TASHKENT  AGGCGTCCATGGTGTTTGAGAATGACTTTTCTGAGTTTGACTCCACCCAGAATAATTTTT
          AGGC TCCATGGTGTTTGAGAATGACTTTTCTGAGTTTGACTCCACCCAGAATAA TTTT
BURMA     AGGCATCCATGGTGTTTGAGAATGACTTTTCTGAGTTTGACTCCACCCAGAATAACTTTT
          CCATGGTGTTTGA AATGA TTTTCTGAGTTTGACTC AC CAGAATAACTTTT
MEXICO    GCCATGCCATGGTGTTTGAAAATGATTTTTCTGAGTTTGACTCGACTCAGAATAACTTTT 4450v      4460v      4470v      4480v      4490v      4500v
TASHKENT  CCCTGGGCCTAGAGTGTGCTATTATGGAGAAGTGTGGGATGCCGAAGTGGCTCATCCGCT
          C CTGGG CTAGAGTGTGCTATTATGGAG AGTGTGGGATGCCG AGTGGCTCATCCGC
BURMA     CTCTGGGTCTAGAGTGTGCTATTATGGAGGAGTGTGGGATGCCGCAGTGGCTCATCCGCC
          C CT GGTCT GAGTG GC ATTATGGA GAGTGTGG ATGCC CAGTGGCT    TC G
MEXICO    CCCTAGGTCTTGAGTGCGCCATTATGGAAGAGTGTGGTATGCCCCAGTGGCTTGTCAGGT 4510v      4520v      4530v      4540v      4550v      4560v
TASHKENT  TGTACCACCTTATAAGGTCTGCGTGGATCCTGCAGGCCCCGAAGGAGTCCCTGCGAGGGT
          TGTA CACCTTATAAGGTCTGCGTGGATG TGCAGGCCCCGAAGGAGTC CTGCGAGGGT
BURMA     TGTATCACCTTATAAGGTCTGCGTGGATCTTGCAGGCCCCGAAGGAGTCTCTGCGAGGGT
          TGTA CA    T GGTC GCGTGGATC TGCAGGCCCC AA GAGTCT TG GAGGGT
MEXICO    TGTACCATGCCGTCCGGTCGGCGTGGATCCTGCAGGCCCCAAAAGAGTCTTTGAGAGGGT 4570v      4580v      4590v      4600v      4610v      4620v
TASHKENT  GTTGGAAGAAACACTCCGGTGAGCCCGGCACTCTTCTATGGAATACTGTCTGGAACATGG
          TTGGAAGAAACACTCCGGTGAGCCCGGCACTCTTCTATGGAATACTGTCTGGAA ATGG
BURMA     TTTGGAAGAAACACTCCGGTGAGCCCGGCACTCTTCTATGGAATACTGTCTGGAATATGG
          T TGGAAGAA CA TC GGTGAGCC GGCA   T CT TGGAATAC GT TGGAA ATGG
MEXICO    TCTGGAAGAAGCATTCTGGTGAGCCGGGCAGCTTGCTCTGGAATACGGTGTGGAACATGG 4630v      4640v      4650v      4660v      4670v      4680v
TASKENT   CCGTTATCACCCATTGTTACGATTTCCGCGATTTGCAGGTGGCTGCCTTTAAAGGTGATG
          CCGTTAT ACCCA TGTTA GA TTCCGCGATTT  AGGTGGCTGCCTTTAAAGGTGATG
BURMA     CCGTTATTACCCACTGTTATGACTTCCGCGATTTTCAGGTGGCTGCCTTTAAAGGTGATG
          C  T ATT CCCA TG TATGA TTCCG GA  T CAGGT GC GCCTT AA GG GA G
MEXICO    CAATCATTGCCCATTGCTATGAGTTCCGGGACCTCCAGGTTGCCGCCTTCAAGGGCGACG 4690v      4700v      4710v      4720v      4730v      4740v
TASHKENT  ATTCGATAGTGCTTTGCAGTGAGTACCGTCAGAGTCCAGGGGCTGCTGTCCTGATTGCTG
          ATTCGATAGTGCTTTGCAGTGAGTA CGTCAGAGTCCAGG GCTGCTGTCCTGAT GC G
BURMA     ATTCGATAGTGCTTTGCAGTGAGTATCGTCAGAGTCCAGGAGCTGCTGTCCTGATCGCCG
          A TCG T GT CT TG AGTGA TA CG CAGAG CCAGG GC G T    CT AT GC G
MEXICO    ACTCGGTCGTCCTCTGTAGTGAATACCGCCAGAGCCCAGGCGCCGGTTCGCTTATAGCAG
```

-continued

```
              4750v         4760v         4770v         4780v         4790v         4800v
TASHKENT  GCTGTGGCTTAAAGCTGAAGGTGGGTTTCCGTCCGATTGGTTTGTATGCAGGTGTTGTGG
          GCTGTGGCTT AAG TGAAGGT G TTTCCG CCGAT GGTTTGTATGCAGGTGTTGTGG
BURMA     GCTGTGGCTTGAAGTTGAAGGTAGATTTCCGCCCGATCGGTTTGTATGCAGGTGTTGTGG
          GCTGTGG TTGAAGTTGAAGG  GA TTCCG CCGAT GG  TGTATGC GG GTTGT G
MEXICO    GCTGTGGTTTGAAGTTGAAGGCTGACTTCCGGCCGATTGGGCTGTATGCCGGGGTTGTCG 4810v         4820v         4830V         4840v         4850v         4860v
TASHKENT  TGACCCCCGGCCTTGGCGCGCTTCCCGACGTCGTGCGCTTGTCCGGCCGGCTTACTGAGA
          TG CCCCCGGCCTTGGCGCGCTTCCCGA GT GTGCGCTTG CCGGCCGGCTTAC GAGA
BURMA     TGGCCCCCGGCCTTGGCGCGCTCCCTGATGTTGTGCGCTTCGCCGGCCGGCTTACCGAGA
          T GCCCC GG CT GG GC CT CC GATGT GT CG TTCGCCGG CGGCTT C GAGA
MEXICO    TCGCCCCGGGGCTCGGGGCCCTACCCGATGTCGTTCGATTCGCCGGACGGCTTTCGGAGA 4870v         4880v         4890v         4900v         4910v         4920v
TASHKENT  AGAATTGGGGCCCTGGCCCTGAGCGGGCGGAGCAGCTCCGCCTTGCTGT
          AGAATTGGGGCCCTGGCCCTGAGCGGGCGGAGCAGCTCCGCCT GCTCT
BURMA     AGAATTGGGGCCCTGGCCCTGAGCGGGCGGAGCAGCTCCGCCTCGCTGTTAGTGATTTCC
          AGAA TGGGG CCTG  CC GAGCGGGC GAGCAGCTCCGCTCGC GT      GATTTCC
MEXICO    AGAACTGGGGGCCTGATCCGGAGCGGGCAGAGCAGCTCCGCCTCGCCGTGCAGGATTTCC 4930v         4940v         4950v         4960v         4970v         4980v
BURMA     TCCGCAAGCTCACGAATGTAGCTCAGATGTGTGTGGATGTTGTTTCCCGTGTTTATGGGG
          TCCG A G T ACGAATGT GC CAGAT TGTGT GA GT GT TC  G GTTA GGGG
MEXICO    TCCGTAGGTTAACGAATGTGGCCCAGATTTGTGTTGAGGTGGTGTCTAGAGTTTACGGGG 4990v         5000v         5010v         5020v         5030v         5040v
BURMA     TTTCCCCTGGACTCGTTCATAACCTGATTGGCATGCTACAGGCTGTTGCTGATGGCAAGG
          TTTCCCC GG CT GTTCATAACCTGAT GGCATGCT GAG CT TTG TGATGG AAGG
MEXICO    TTTCCCCGGGTCTGGTTCATAACCTGATAGGCATGCTCCAGACTATTGGTGATGGTAAGG 5050v         5060v         5070v         5080v         5090v         5100v
BURMA     CACATTTCACTGAGTCAGTAAAACCAGTGCTCGACTTGACAAATTGAATCTTGTGTCGGG
          C CATTT AC GAGTC GT AA CC  T CT GAC T ACA A TCAAT  TG   CGG
MEXICO    CGCATTTTACAGAGTCTGTTAAGCCTATACTTGACCTTACACACTCAATTATGCACCGGT 5110v         5120v         5130v         5140v         5150v         5160v
BURMA     TGGAATGAATAACATGTCTTTTGCTGCGCCCATGGGTTCGCGACCATGCGCCCTCGGCCT
          GAATGAATAACATGT   TTTGCTGCGCCCATGGGTTCGC ACCATGCGCCCT GGCCT
MEXICO    CTGAATGAATAACATGTGGTTTGCTGCGCCATGGGTTCGCCACCACTGCGCCCTAGGCCT 5170v         5180v         5190v         5200v         5210v         5220v
BURMA     ATTTGTTGCTGCTCCTCATGTTTTTGCCTATGCTGCCCGCGCCACCGCCCGGTCAGCCG
          TTTTG TG TG TCCTC TGTTT TGCCTATG TGCCCGCGCC ACCG CCGGTCAGCCG
MEXICO    CTTTTGCTGTTGTTCCTCTTGTTTCTGCCTATGTTGCCCGCGCCACCGACCGGTCAGCCG 5230v         5240v         5250v         5260v         5270v         5280v
BURMA     TCTGGCCGCCGTCGTGGGCGGCGCAGCGGCGGTTCCGGCGGTGGTTTCTGGGGTGACCGG
          TCTGGCCGCCGTCGTGGGCGGCGCAGCGGCGGT CCGGCGGTGGTTTCTGGGGTGACCGG
MEXICO    TCTGGCCGCCGTCGTGGGCGGCGCAGCGGCGGTACCGGCGGTGGTTTCTGGGGTGACCGG 5290v         5300v         5310v         5320v         5330v         5340v
BURMA     GTTGATTCTCAGCCCTTCGCAATCCCCTATATTCATCCAACCAACCCCTTCGCCCCCGAT
          GTTGATTCTCAGCCCTTCGCAATCCCCTATATTCATCCAACCAACCCCTT GCCCC GA
MEXICO    GTTGATTCTCAGCCCTTCGCAATCCCCTATATTCATCCAACCAACCCCTTTGCCCCAGAC 5350v         5360v         5370v         5380v         5390v         5400v
BURMA     GTCACCGCTGCGGCCGGGGCTGGACCTCGTGTTCGCCAACCCGCCCGACCACTCGGCTCC
          GT   CCGCTGCG CCGGG CTGGACCTCG TTCGCCAACC GCCCG CCACT GGCTCC
MEXICO    GTTGCCGCTGCGTCCGGGTCTGGACCTCGCCTTCGCCAACCAGCCCGGCCACTTGGCTCC 5410v         5420v         5430v         5440v         5450v         5460v
BURMA     GCTTGGCGTGACCAGGCCCAGCGCCCCGCCGTTGCCTCACGTCGTAGACCTACCACAGCT
          CTTGGCG GA CAGGCCCAGCGCCCC CCG TGCCTC CGTCG  GACCT CCACAGC
MEXICO    ACTTGGCGAGATCAGGCCCAGCGCCCCTCCGCTGCCTCCCGTCGCCGACCTGCCACAGCC 5470v         5480v         5490v         5500v         5510v         5520v
BURMA     GGGGCCGCGCCGCTAACCGCGGTCGCTCCGGCCCATGACACCCCGCCAGTGCCTGATGTC
          GGGGC GCG CGCT AC GC GT GC CC GCCCATGACACC C CC GT CC GA GT
MEXICO    GGGGCTGCGGCGCTGACGGCTGTGGCGCCTGCCCATGACACCTCACCCGTCCCGGACGTT 5530v         5540v         5550v         5560v         5570v         5580v
BURMA     GACTCCCGCGGCGCCATCTTGCGCCGGCAGTATAACCTATCAACATCTCCCCTTACCTCT
          GA TC CGCGG GC AT  T CGCCG CAGTATAA  T TC AC TC CCCCT AC TC
MEXICO    GATTCTCGCGGTGCAATTCTACGCCGCCAGTATAATTTGTCTACTTCACCCCTGACATCC 5590v         5600v         5610v         5620v         5630v         5640v
BURMA     TCCGTGGCCACCGGCACTAACCTGGTTCTTTATGCCGCCCCTCTTAGTCCGCTTTTACCC
          TC GTGGCC C GGCACTAA  T GT CT TATGC GCCCC CTTA TCCGC T T CC
MEXICO    TCTGTGGCCTCTGGCACTAATTTAGTCCTGTATGCAGCCCCCCTTAATCCGCCTCTGCCG
```

-continued

```
              5650v       5660v       5670v       5680v       5690v       5700v
BURMA   CTTCAGGACGGCACCAATACCCATATAATGGCCACGGAAGCTTCTAATTATGCCCAGTAC
        CT CAGGACGG AC AATAC CA AT ATGGCCAC GA GC TC AATTATGC CAGTAC
MEXICO  CTGCAGGACGGTACTAATACTCACATTATGGCCACAGAGGCCTCCAATTATGCACAGTAC 5710v       5720v       5730v       5740v       5750v       5760v
BURMA   CGGGTTGCCCGTGCCACAATCCGTTACCGCCCGCTGGTCCCCAATGCTGTCGGCGGTTAC
        CGGGTTGCCCG GC AC ATCCGTTACCG CC CT GT CC AATGC GT GG GG TA
MEXICO  CGGGTTGCCCGCGCTACTATCCGTTACCGGCCCCTAGTGCCTAATGCAGTTGGAGGCTAT 5770v       5780v       5790v       5800v       5810v       5820v
BURMA   GCCATCTCCATCTCATTCTGGCCACAGACCACCACCACCCCGACGTCCGTTGATATGAAT
        GC AT TCCAT TC TTCTGGCC CA AC ACCAC ACCCC AC TC GTTGA ATGAAT
MEXICO  GCTATATCCATTTCTTTCTGGCCTCAAACAACCACAACCCCTACATCTGTTGACATGAAT 5830v       5840v       5850v       5860v       5870v       5880v
BURMA   TCAATAACCTCGACGGATGTTCGTATTTTAGTCCAGCCCGGCATAGCCTCTGAGCTTGTG
        TC AT AC TC AC GATGT G ATT T GT CA CC GGCATAGC TCTGA T GT
MEXICO  TCCATTACTTCCACTGATGTCAGGATTCTTGTTCAACCTGGCATAGCATCTGAATTGGTC 5890v       5900v       5910v       5920v       5930v       5940v
BURMA   ATCCCAAGTGAGCGCCTACACTATCGTAACCAAGGCTGGCGCTCCGTCGAGACCTCTGGG
        ATCCCAAG GAGCGCCT CACTA CG AA CAAGG TGGCGCTC GT GAGAC TCTGG
MEXICO  ATCCCAAGCGAGCGCCTTCACTACCGCAATCAAGGTTGGCGCTCGGTTGAGACATCTGGT 5950v       5960v       5970v       5980v       5990v       6000v
BURMA   GTGGCTGAGGAGGAGGCTACCTCTGGTCTTGTTATGCTTTGCATACATGGCTCACTCGTA
        GT GCTGAGGAGGA GC ACCTC GGTCTTGT ATG T TGCATACATGGCTC C GT
MEXICO  GTTGCTGAGGAGGAAGCCACCTCCGGTCTTGTCATGTTATGCATACATGGCTCTCCAGTT 6010v       6020v       6030v       6040v       6050v       6060v
BURMA   AATTCCTATACTAATACACCCTATACCGGTGCCCTCGGGCTGTTGGACTTTGCCCTTGAG
        AA TCCTATAC AATAC CC TATACCGGTGCCCT GG T TGGACTTTGCC T GAG
MEXICO  AACTCCTATACCAATACCCCTTATACCGGTGCCCTTGGCTTACTGGACTTTGCCCTTAGAG 6070v       6080v       6090v       6100v       6110v       6120v
BURMA   CTTGAGTTTCGCAACCTTACCCCCGGTAACACCAATACGCGGGTCTCCCGTTATTCCAGC
        CTTGAGTTTCGCAA CT ACC CC GTAACACCAATAC CG GT TCCCGTTA TCCAGC
MEXICO  CTTGAGTTTCGCAATCTCACCACCTGTAACACCAATACACGTGTGTCCCGTTACTCCAGC 6130v       6140v       6150v       6160v       6170v       6180v
BURMA   ACTGCTCGCCACCGCCTTCGTCGCGGTGCGGACGGGACTGCCGAGCTCACCACCACGGCT
        ACTGCTCG CAC C    CG  G  G    GACGGGACTGC GAGCT ACCAC AC GC
MEXICO  ACTGCTCGTCACTCCGCCCGAGGGGCC---GACGGGACTGCGGAGCTGACCACAACTGCA 6190v       6200v       6210v       6220v       6230v       6240v
BURMA   GCTACCCGCTTTATGAAGGACCTCTATTTTACTAGTACTAATGGTGTCGGTGAGATCGGC
        GC ACC G TT ATGAA GA CTC A TTTAC G   TAATGG GT GGTGA TCGGC
MEXICO  GCCACCAGGTTCATGAAAGATCTCCACTTTACCGGCCTTAATGGGGTAGGTGAAGTCGGC 6250v       6260v       6270v       6280v       6290v       6300v
BURMA   CGCGGGATAGCCCTCACCCTGTTCAACCTTGCTGACACTCTGCTTGGCGGCCTGCCGACA
        CGCGGGATAGC CT AC  T  T AACCTTGCTGACAC CT CT GGCGG CT CCGACA
MEXICO  CGCGGGATAGCTCTAACATTACTTAACCTTGCTGACACGCTCCTCGGCGGGCTCCCGACA 6310v       6320v       6330v       6340v       6350v       6360v
BURMA   GAATTGATTTCGTCGGCTGGTGGCCAGCTGTTCTACTCCCGTCCCGTTGTCTCAGCCAAT
        GAATT ATTTCGTCGGCTGG GG CA CTGTT TA TCCCG CC GTTGTCTCAGCCAAT
MEXICO  GAATTAATTTCGTCGGCTGGCGGCAACTGTTTTATTCCCGCCCGGTTGTCTCAGCCAAT 6370v       6380v       6390v       6400v       6410v       6420v
BURMA   GGCGAGCCGACTGTTAAGTTGTATACATCTGTAGAGAATGCTCAGCAGGATAAGGGTATT
        GGCGAGCC AC GT AAG T TATACATC GT GAGAATGCTCAGCAGGATAAGGGT TT
MEXICO  GGCGAGCCAACCGTGAAGCTCTATACATCAGTGGAGAATGCTCAGCAGGATAAGGGTGTT 6430v       6440v       6450v       6460v       6470v       6480v
BURMA   GCAATCCCGCATGACATTGACCTCGGAGAATCTCGTGTGGTTATTCAGGATTATGATAAC
        GC ATCCC CA GA AT GA CT GG GA TC CGTGTGGT ATTCAGGATTATGA AAC
MEXICO  GCTATCCCCCACGATATCGATCTTGGTGATTCGCGTGTGGTCATTCAGGATTATGACAAC 6490v       6500v       6510v       6520v       6530v       6540v
BURMA   CAACATGAACAAGATCGGCCGACGCCTTCTCCAGCCCCATCGCGCCCTTTCTCTGTCCTT
        CA CATGA CA GATCGGCC AC CC TC CC GC CCATC CG CCTTT TCTGT CT
MEXICO  CAGCATGAGCAGGATCGGCCCACCCCGTCGCCTGCGCCATCTCGGCCTTTTTCTGTTCTC 6550v       6560v       6570v       6580v       6590v       6600v
BURMA   CGAGCTAATGATGTGCTTTGGCTCTCTCTCACCGCTGCCGAGTATGACCAGTCCACTTAT
        CGAGC AATGATGT CTTTGGCT TC CTCAC GC GCCGAGTATGACCAGTCCACTTA
MEXICO  CGAGCAAATGATGTACTTTGGCTGTCCCTCACTGCAGCCGAGTATGACCAGTCCACTTAC
```

```
                    6610v           6620v           6630v           6640v           6650v           6660v
BURMA    GGCTCTTCGACTGGCCCAGTTTATGTTTCTGACTCTGTGACCTTGGTTAATGTTGCGACC
         GG TC TC ACTGGCCC GTTTAT T TC GAC    GTGAC TTGGT AATGTTGCGAC
MEXICO   GGGTCGTCAACTGGCCCGGTTTATATCTCGGACAGCGTGACTTTGGTGAATGTTGCGACT 6670v           6680v           6690v           6700v           6710v           6720v
BURMA    GGCGCGCAGGCCGTTGCCCGGTCGCTCGATTGGAGGAAGGTCACACTTGACGGTCGCCCC
         GGCGCGC AGGCCGT GCCCG TCGCT GA TGG CCAA GTCAC CT GACGG CG CCC
MEXICO   GGCGCGCAGGCCGTAGCCCGATCGCTTGACTGGTCCAAAGTCACCCTCGACGGGCGGCCC 6730v           6740v           6750v           6760v           6770v           6780v
BURMA    CTCTCCACCATCCAGCAGTACTCGAAGACCTTCTTTGTCCTGCCGCTCCGCGGTAAGCTC
         CTC C AC    T    AGCA TA TC AAGAC TTCTTTGT CT CC CT CG GG AAGCTC
MEXICO   CTCCCGACTGTTGAGCAATATTCCAAGACATTCTTTGTGCTCCCCCTTCGTGGCAAGCTC 6790v           6800v           6810v           6820v           6830v           6840v
BURMA    TCTTTCTGGGAGGCAGGCACAACTAAAGCCGGGTACCCTTATAATTATAACACCACTGCT
         TC TT TGGGAGGC GGCACAAC AAAGC GG TA CCTTATAATTATAA AC ACTGCT
MEXICO   TCCTTTTGGGAGGCCGGCACAACAAAAGCAGGTTATCCTTATAATTATAATACTACTGCT 6850v           6960v           6870v           6880v           6890v           6900v
BURMA    AGCGACCAACTGCTTGTCGAGAATGCCGCCGGGCACCGGGTCGCTATTTCCACTTACACC
         AG GACCA   T CT   T GA AATGC GCCGG CA CGGGTCGC ATTTC AC TA ACC
MEXICO   AGTGACCAGATTCTGATTGAAAATGCTGCCGGCCATCGGGTCGCCATTTCAACCTATACC 6910v           6920v           6930v           6940v           6950v           6960v
BURMA    ACTAGCCTGGGTGCTGGTCCCGTCTCCATTTCTGCGGTTGCCGTTTTAGCCCCCCACTCT
         AC AG CT GG GC GGTCC GTC CCATTTCTGCGG   GC GTTTT GC CC C CTC
MEXICO   ACCAGGCTTGGGGCCGGTCCGGTCGCCATTTCTGCGGCCGCGGTTTTGGCTCCACGCTCC 6970v           6980v           6990v           7000v           7010v           7020v
BURMA    GCGCTAGCATTGCTTGAGGATACCTTGGACTACCCTGCCCGCGCCCATACTTTTGATGAT
         GC CT GC    TGCT GAGGATAC TT GA TA CC G   CG GC CA AC TTTGATGA
MEXICO   GCCCTGGCTCTGCTGGAGGATACTTTTGATTATCCGGGGCGGGCGCACACATTTGATGAC 7030v           7040v           7050v           7060v           7070v           7080v
BURMA    TTCTGCCCAGAGTGCCGCCCCCTTGGCCTTCAGGGCTGCGCTTTCCAGTCTACTGTCGCT
         TTCTGCCC GA TGCCGC C   T GGCCT CAGGG TG GCTTTCCAGTC ACTGTCGCT
MEXICO   TTCTGCCCTGAATGCCGCGCTTTAGGCCTCCAGGGTTGTGCTTTCCAGTCAACTGTCGCT 7090v           7100v           7110v           7120v           7130v           7140v
BURMA    GAGCTTCAGCGCCTTAAGATGAAGGTGGGTAAAACTCGGGAGTTGTAGTTTATTTGCTTG
         GAGCT CAGCGCCTTAA   T AAGGTGGGTAAAACTCGGGAGTTGTAGTTTATTTG TG
MEXICO   GAGCTCCAGCGCCTTAAAGTTAAGGTGGGTAAAACTCGGGAGTTGTAGTTTATTTGGCTG 7150v           7160v           7170v           7180v           7190v
BURMA    TGCCCCCCTTCTTTCTGTTGC---------TTATTTCTCATTTCTGCGTTCCGCGCTCCC
         TGCCC CCT CTT     TGC         TTATTTC    TTTCT GT CCGCGCTCCC
MEXICO   TGCCCACCTACTTATATCTGCTGATTTCCTTTATTTCCTTTTTCTCGGTCCCGCGCTCCC v 7195
BURMA    TGA
         TGA
MEXICO   TGA
```

A number of open reading frames, which are potential coding regions, have been found within the DNA sequences set forth above. As has already been noted, consensus residues for the RNA-directed RNA polymerase (RDRP) were identified in the HEV (Burma) strain clone ET1.1. Once a contiguous overlapping set of clones was accumulated, it became clear that the nonstructural elements containing the RDRP as well as what were identified as consensus residues for the helicase domain were located in the first large open reading frame (ORFl). ORFl covers the 5' half of the genome and begins at the first encoded met, after the 27th bp of the apparent non-coding sequence, and then extends 5079 bp before reaching a termination codon. Beginning 37 bp downstream from the ORF1 stop codon in the plus 1 frame is the second major opening reading frame (ORF2) extending 1980 bp and terminating 68 bp upstream from the point of poly A addition. The third forward ORF (in the plus 2 frame) is also utilized by HEV. ORF3 is only 370 bp in length and would not have been predicted to be utilized by the virus were it not for the identification of the immunoreactive cDNA clone 406.4-2 from the Mexico SISPA cDNA library (see below for detailed discussion). This epitope confirmed the utilization of ORF3 by the virus, although the means by which this ORF is expressed has not yet been fully elucidated. If we assume that the first met is utilized, ORF3 overlaps ORF1 by 1 bp at its 5' end and ORF2 by 328 bp at its 3' end. ORF2 contains the broadly reactive 406.3-2 epitope and also a signal sequence at its extreme 5' end. The first half of this ORF2 also has a high pI value (>10) similar to that seen with other virus capsid proteins. These data suggest that the ORF2 might be the predominant structural gene of HEV.

The existence of subgenomic transcripts prompted a set of experiments to determine whether these RNAs were produced by splicing from the 5' end of the genome. An analysis using subgenomic probes from throughout the genome, including the extreme 5' end, did not provide evidence for a spliced transcript. However, it was discovered that a region of the genome displayed a high degree of homology with a 21 bp segment identified in Sindbis as a probably internal initiation site for RNA transcription used in the production of its subgenomic messages. Sixteen of 21 (76%) of the nucleotides are identical.

Two cDNA clones which encode an epitope of HEV that is recognized by sera collected from different ET-NANB outbreaks (i.e., a universally recognized epitope) have been isolated and characterized. One of the clones immunoreacted with 8 human sera from different infected individuals and the other clone immunoreacted with 7 of the human sera tested. Both clones immunoreacted specifically with cyno sera from infected animals and exhibited no immunologic response to sera from uninfected animals. The sequences of the cDNAs in these recombinant phages, designated 406.3-2 and 406.4-2 have been determined. The HEV open reading frames are shown to encode epitopes specifically recognized by sera from patients with HEV infections. The cDNA sequences and the polypeptides that they encode are set forth below.

Epitopes derived from Mexican strain of HEV:

406.4-2 sequence (nucleotide sequence has SEQ ID NO.13; amino acid sequence has SEQ ID NO.14):

406.3-2 sequence (nucleotide sequence has SEQ ID NO.15; amino acid sequence has SEQ ID NO.16).

The universal nature of these epitopes is evident from the homology exhibited by the DNA that encodes them. If the epitope coding sequences from the Mexican strains shown above are compared to DNA sequences from other strains, such as the Burmese strain also set forth above, similarities are evident, as shown in the following comparisons.

Comparison of 406.4-2 epitopes, HEV Mexico and Burma strains:

```
                        10         20         30
MEXICAN (SEQ ID NO.17)  ANQPGHLAPLGEI RPSAPPLPP VADLPQPGLRR
                        :: .: . ::::  .::::::::.:.:::: : ::
BURMA (SEQ ID NO.18 )   ANP PDHS APLGVTRPSAPPLPH VVDLPQLGPRR
                        10         20         30
```

There is 73.5% identity in a 33-amino acid overlap.
Comparison of 406.3-2 epitopes, HEV Mexico and Burma strains:
MEXICAN(SEQ ID No.19)

```
         10         20         30         40
TFDYPGRAHTFDDFCPECRALGLQGCAFQSTVAELQRLKV KV
:.:::.::::::::::::::: :::::::::::::::::: ::
TLDYPARAHTFDDFCPECRPLGLQGCAFQSTVAELQRLKMKV
         10         20         30         40
```

BURMA(SEQ ID No.20) There is 90.5% identity in the 42-amino acid overlap.

It will be recognized by one skilled in the art of molecular genetics that each of the specific DNA sequences given above shows a corresponding complementary DNA sequence as well as RNA sequences corresponding to both the principal sequence shown and the complementary DNA sequence. Additionally, open reading frames encoding peptides are present, and expressible peptides are disclosed by the nucleotide sequences without setting forth the amino acid sequences explicitly, in the same manner as if the amino acid sequences were explicitly set forth as in the ET1.1 sequence or other sequences above.

DETAILED DESCRIPTION OF THE INVENTION

I. Definitions

The terms defined below have the following meaning herein:

1. "Enterically transmitted non-A/non-B hepatitis viral agent, ET-NANB, or HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in *E. coli* strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an ET-NANB viral agent if it has the same or substantially the same basepair sequence as a region of the viral agent genome.

5. A protein is "derived from" an ET-NANB viral agent if it is encoded by an open reading frame of a DNA or RNA fragment derived from an ET-NANB viral agent.

II. Obtaining Cloned ET-NANB Fragments

According to one aspect of the invention, it has been found that a virus-specific DNA clone can be produced by (a) isolating RNA from the bile of a cynomolgus monkey having a known ET-NANB infection, (b) cloning the cDNA fragments to form a fragment library, and (c) screening the library by differential hybridization to radiolabeled cDNAs from infected and non-infected bile sources.

A. cDNA Fragment Mixture

ET-NANB infection in cynomolgus monkeys is initiated by inoculating the animals intravenously with a 10% w/v suspension from human case stools positive for 27–34 nm ET-NANB particles (mean diameter 32 nm). An infected animal is monitored for elevated levels of alanine aminotransferase, indicating hepatitis infection. ET-NANB infection is confirmed by immunospecific binding of seropositive antibodies to virus-like particles (VLPs), according to published methods (Gravelle). Briefly, a stool (or bile) specimen taken from the infected animal 3–4 weeks after infection is diluted 1:10 with phosphate-buffered saline, and the lot suspension is clarified by low-speed centrifugation and filtration successively through 1.2 and 0.45 micron filters. The material may be further purified by pelleting through a 30% sucrose cushion (Bradley). The resulting preparation of VLPs is mixed with diluted serum from human patients with known ET-NANB infection. After incubation overnight, the mixture is centrifuged overnight to pellet immune aggregates, and these are stained and examined by electron microscopy for antibody binding to the VLPs.

ET-NANB infection can also be confirmed by seroconversion to VLP-positive serum. Here the serum of the infected animal is mixed as above with 27–34 nm VLPs isolated from the stool specimens of infected human cases and examined by immune electron microscopy for antibody binding to the VLPs.

Bile can be collected from ET-NANB positive animals by either cannulating the bile duct and collecting the bile fluid or by draining the bile duct during necropsy. Total RNA is extracted from the bile by hot phenol extraction, as outlined in Example 1A. The RNA fragments are used to synthesize corresponding duplex cDNA fragments by random priming, also as referenced in Example 1A. The cDNA fragments may be fractionated by gel electrophoresis or density gradient centrifugation to obtain a desired size class of fragments, e.g., 500–4,000 basepair fragments.

Although alternative sources of viral material, such as VLPs obtained from stool samples (as described in Example 4), may be used for producing a CDNA fraction, the bile source is preferred. According to one aspect of the invention, it has been found that bile from ET-NANB-infected monkeys shows a greater number of intact viral particles than material obtained from stool samples, as evidenced by immune electron microscopy. Bile obtained from an ET-NANB infected human or cynomolgus macaque, for use as a source of ET-NANB viral protein or genomic material, or intact virus, forms part of the present invention.

B. cDNA Library and Screening

The cDNA fragments from above are cloned into a suitable cloning vector to form a cDNA library. This may be done by equipping blunt-ended fragments with a suitable end linker, such as an EcoRI sequence, and inserting the fragments into a suitable insertion site of a cloning vector, such as at a unique EcoRI site. After initial cloning, the library may be re-cloned, if desired, to increase the percentage of vectors containing a fragment insert. The library construction described in Example 1B is illustrative. Here cDNA fragments were blunt-ended, equipped with EcoRI ends, and inserted into the EcoRI site of the lambda phage vector gt10. The library phage, which showed less than 5% fragment inserts, was isolated, and the fragment inserts re-cloned into the lambda gt10 vector, yielding more than 95% insert-containing phage.

The cDNA library is screened for sequences specific for ET-NANB by differential hybridization to cDNA probes derived from infected and non-infected sources. cDNA fragments from infected and non-infected source bile or stool viral isolates can be prepared as above. Radiolabeling the fragments is by random labeling, nick translation, or end labeling, according to conventional methods (Maniatis, p. 109). The cDNA library from above is screened by transfer to duplicate nitrocellulose filters, and hybridization with both infected-source and non-infected-source (control) radiolabeled probes, as detailed in Example 2. In order to recover sequences that hybridize at the preferred outer limit of 25–30% basepair mismatches, clones can be selected if they hybridize under the conditions described in Maniatis et al., op. cit., pp. 320–323, but using the following wash conditions: 2×SCC, 0.1% SDS, room temperature—twice, 30 minutes each; then 2×SCC, 0.1% SDS, 50° C.—once, 30 minutes; then 2×SCC, room temperature—twice, 10 minutes each. These conditions allowed identification of the Mexican isolate discussed above using the ET1.1 sequence as a probe. Plaques which show selective hybridization to the infected-source probes are preferably re-plated at low plating density and re-screened as above, to isolate single clones which are specific for ET-NANB sequences. As indicated in Example 2, sixteen clones which hybridized specifically with infected-source probes were identified by these procedures. One of the clones, designated lambda gt101.1, contained a 1.33 kilobase fragment insert.

C. ET-NANB Sequences

The basepair sequence of cloned regions of the ET-NANB fragments from Part B are determined by standard sequencing methods. In one illustrative method, described in Example 3, the fragment insert from the selected cloning vector is excised, isolated by gel electrophoresis, and inserted into a cloning vector whose basepair sequence on either side of the insertion site is known. The particular vector employed in Example 3 is a pTZKF1 vector shown at the left in FIG. 1. The ET-NANB fragment from the gt10-1.1 phage was inserted at the unique EcoRI site of the pTZKF1 plasmid. Recombinants carrying the desired insert were identified by hybridization with the isolated 1.33 kilobase fragment, as described in Example 3. One selected plasmid, identified as pTZKF1 (ET1.1), gave the expected 1.33 kb fragment after vector digestion with EcoRI. *E. coli* strain BB4 infected with the pTZKF1(ET1.1) plasmid has been deposited with the American Type Culture Collection, Rockville, Md., and is identified by ATCC deposit number 67717.

The pTZKF1(ET1.1) plasmid is illustrated at the bottom in FIG. 1. The fragment insert has 5' and 3' end regions denoted at A and C, respectively, and an intermediate region, denoted at B. The sequences in these regions were determined by standard dideoxy sequencing and were set forth in an earlier application in this series. The three short sequences (A, B, and C) are from the same insert strand. As will be seen in Example 3, the B-region sequence was actually determined from the opposite strand, so that the B region sequence shown above represents the complement of the sequence in the sequenced strand. The base numbers of the partial sequences are approximate.

Later work in the laboratory of the inventors identified the full sequence, set forth above. Fragments of this total sequence can readily be prepared using restriction endonucleases. Computer analysis of both the forward and reverse sequence has identified a number of cleavage sites.

III. ET-NANB Fragments

According to another aspect, the invention includes ET-NANB-specific fragments or probes which hybridize with ET-NANB genomic sequences or cDNA fragments derived therefrom. The fragments may include full-length cDNA fragments such as described in Section II, or may be derived from shorter sequence regions within cloned cDNA fragments. Shorter fragments can be prepared by enzymatic digestion of full-length fragments under conditions which yield desired-sized fragments, as will be described in Section IV. Alternatively, the fragments can be produced by oligonucleotide synthetic methods, using sequences derived from the cDNA fragments. Methods or commercial services for producing selected-sequence oligonucleotide fragments are available. Fragments are usually at least 12 nucleotides in length, preferably at least 14, 20, 30 or 50 nucleotides, when used as probes. Probes can be full length or less than 500, preferably less than 300 or 200, nucleotides in length.

To confirm that a given ET-NANB fragment is in fact derived from the ET-NANB viral agent, the fragment can be shown to hybridize selectively with cDNA from infected sources. By way of illustration, to confirm that the 1.33 kb fragment in the pTZKF1(ET1.1) plasmid is ET-NANB in origin, the fragment was excised from the pTZKF1(ET1.1) plasmid, purified, and radiolabeled by random labeling. The radiolabeled fragment was hybridized with fractionated cDNAs from infected and non-infected sources to confirm that the probe reacts only with infected-source cDNAs. This method is illustrated in Example 4, where the above radiolabeled 1.33 kb fragment from pTZKF1(ET1.1) plasmid was examined for binding to cDNAs prepared from infected and non-infected sources. The infected sources are (1) bile from a cynomolgus macaque infected with a strain of virus derived from stool samples from human patients from Burma with known ET-NANB infections and (2) a viral agent derived from the stool sample of a human ET-NANB patient from Mexico. The cDNAs in each fragment mixture were first amplified by a linker/primer amplification method described in Example 4. Fragment separation was on agarose gel, followed by Southern blotting and then hybridization to bind the radiolabeled 1.33 kb fragment to the fractionated cDNAs. The lane containing cDNAs from the infected sources showed a smeared band of bound probe, as expected (cDNAs amplified by the linker/primer amplification method would be expected to have a broad range of sizes). No probe binding to the amplified cDNAs from the non-infected sources was observed. The results indicate that the 1.33 kb probe is specific for cDNA fragments associated with ET-NANB infection. This same type of study, using ET 1.1 as the probe, has demonstrated hybridization to ET-NANB samples collected from Tashkent, Somalia, Borneo and Pakistan. Secondly, the fact that the probe is specific for ET-NANB related sequences derived from different continents (Asia, Africa and North America) indicates the cloned ET-NANB Burma sequence (ET1.1) is derived from a common ET-NANB virus or virus class responsible for ET-NANB hepatitis infection worldwide.

In a related confirmatory study, probe binding to fractionated genomic fragments prepared from human or cynomolgus macaque genomic DNA (both infected and uninfected) was examined. No probe binding was observed to either genomic fraction, demonstrating that the ET-NANB fragment is not an endogenous human or cynomolgus genomic fragment and additionally demonstrating that HEV is an RNA virus.

Another confirmation of ET-NANB specific sequences in the fragments is the ability to express ET-NANB proteins from coding regions in the fragments and to demonstrated specific sero-reactivity of these proteins with sera collected during documented outbreaks of ET-NANB. Section IV below discusses methods of protein expression using the fragments.

One important use of the ET-NANB-specific fragments is for identifying ET-NANB-derived cDNAs which contain additional sequence information. The newly identified cDNAs, in turn, yield new fragment probes, allowing further iterations until the entire viral genome is identified and sequenced. Procedures for identifying additional ET-NANB library clones and generating new probes therefrom generally follow the cloning and selection procedures described in Section II.

The fragments (and oligonucleotides prepared based on the sequences given above) are also useful as primers for a polymerase chain reaction method of detecting ET-NANB viral genomic material in a patient sample. This diagnostic method will be described in Section V below.

Two specific genetic sequences derived from the Mexican strain, identified herein as 406.3-2 and 406.4-2, have been identified that encode immunogenic epitopes. This was done by isolating clones which encode epitopes that immunologically react specifically with sera from individuals and experimental animals infected with HEV. Comparison of the isolated sequences with those in the Genebank collection of genetic sequences indicate that these viral sequences are novel. Since these sequences are unique, they can be used to identify the presence of HEV and to distinguish this strain of hepatitis from HAV, HBV, and HCV strains. The sequences are also useful for the design of oligonucleotide probes to diagnose the presence of virus in samples. They can be used for the synthesis of polypeptides that themselves are used in immunoassays. The specific 406.3-2 and 406.4-2 sequences can be incorporated into other genetic material, such as vectors, for ease of expression or replication. They can also be used (as demonstrated above) for identifying similar antigenic regions encoded by related viral strains, such as the Burmese strain.

IV. ET-NANB Proteins

As indicated above, ET-NANB proteins can be prepared by expressing open reading-frame coding regions in ET-NANB fragments. In one preferred approach, the ET-NANB fragments used for protein expression are derived from cloned cDNAs which have been treated to produce desired-size fragments, and preferably random fragments with sizes predominantly between about 100 to about 300 base pairs. Example 5 describes the preparation of such fragments by DNAs digestion. Because it is desired to obtain peptide antigens of between about 30 to about 100 amino acids, the digest fragments are preferably size fractionated, for example by gel electrophoresis, to select those in the approximately 100–300 basepair size range. Alternatively, cDNA libraries constructed directly from HEV-containing sources (e.g., bile or stool) can be screened directly if cloned into an appropriate expression vector (see below).

For example, the ET-NANB proteins expressed by the 406.3-2 and 406.4-2 sequences (and peptide fragments thereof) are particularly preferred since these proteins have been demonstrated to be immunoreactive with a variety of different human sera, thereby indicating the presence of one or more epitopes specific for HEV on their surfaces. These clones were identified by direct screening of a gt11 library.

A. Expression Vector

The ET-NANB fragments are inserted into a suitable expression vector. One exemplary expression vector is lambda gt11, which contains a unique EcoRI insertion site 53 base pairs upstream of the translation termination codon of the beta-galactosidase gene. Thus, the inserted sequence will be expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (c1857) which causes viral lysogeny at permissive temperatures, e.g., 32° C., and leads to viral lysis at elevated temperatures, e.g., 37° C. Advantages of this vector include: (1) highly efficient recombinant generation, (2) ability to select lysogenized host cells on the basis of host-cell growth at permissive, but not non-permissive, temperatures, and (3) high levels of recombinant fusion protein production. Further, since phage containing a heterologous insert produces an inactive beta-galactosidase enzyme, phage with inserts can be readily identified by a beta-galactosidase colored-substrate reaction.

For insertion into the expression vector, the viral digest fragments may be modified, if needed, to contain selected restriction-site linkers, such as EcoRI linkers, according to conventional procedures. Example 1 illustrates methods for cloning the digest fragments into lambda gt11, which includes the steps of blunt-ending the fragments, ligating with EcoRI linkers, and introducing the fragments into EcoRI-cut lambda gt11. The resulting viral genomic library may be checked to confirm that a relatively large (representative) library has been produced. This can be done, in the case of the lambda gt11 vector, by infecting a suitable bacterial host, plating the bacteria, and examining the plaques for loss of beta-galactosidase activity. Using the procedures described in Example 1, about 50% of the plaques showed loss of enzyme activity.

B. Peptide Antigen Expression

The viral genomic library formed above is screened for production of peptide antigen (expressed as a fusion protein) which is immunoreactive with antiserum from ET-NANB seropositive individuals. In a preferred screening method, host cells infected with phage library vectors are plated, as above, and the plate is blotted with a nitrocellulose filter to transfer recombinant protein antigens produced by the cells onto the filter. The filter is then reacted with the ET-NANB antiserum, washed to remove unbound antibody, and reacted with reporter-labeled, anti-human antibody, which becomes bound to the filter, in sandwich fashion, through the anti-ET-NANB antibody.

Typically phage plaques which are identified by virtue of their production of recombinant antigen of interest are re-examined at a relatively low density for production of antibody-reactive fusion protein. Several recombinant phage clones which produced immunoreactive recombinant antigen were identified in the procedure.

The selected expression vectors may be used for scale-up production, for purposes of recombinant protein purification. Scale-up production is carried out using one of a variety of reported methods for (a) lysogenizing a suitable host, such as E. coli, with a selected lambda gt11 recombinant (b) culturing the transduced cells under conditions that yield high levels of the heterologous peptide, and (c) purifying the recombinant antigen from the lysed cells.

In one preferred method involving the above lambda gt11 cloning vector, a high-producer E. coli host, BNN103, is infected with the selected library phage and replica plated on two plates. One of the plates is grown at 32° C., at which viral lysogeny can occur, and the other at 42° C., at which the infecting phage is in a lytic stage and therefore prevents cell growth. Cells which grow at the lower but not the higher temperature are therefore assumed to be successfully lysogenized.

The lysogenized host cells are then grown under liquid culture conditions which favor high production of the fused protein containing the viral insert, and lysed by rapid freezing to release the desired fusion protein.

C. Peptide Purification

The recombinant peptide can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused protein prepared as above, the protein isolation techniques which are used can be adapted from those used in isolation of the native protein. Thus, for isolation of a soluble betagalactosidase fusion protein, the protein can be isolated readily by simple affinity chromatography, by passing the cell lysis material over a solid support having surface-bound anti-beta-galactosidase antibody.

D. Viral Proteins

The ET-NANB protein of the invention may also be derived directly from the ET-NANB viral agent. VLPs or protein isolated from stool or liver samples from an infected individual, as above, are one suitable source of viral protein material. The VLPs isolated from the stool sample may be further purified by affinity chromatography prior to protein isolation (see below). The viral agent may also be raised in cell culture, which provides a convenient and potentially concentrated source of viral protein. Co-owned U.S. patent application Ser. No. 846,757, filed Apr. 1, 1986, now abandoned, describes an immortalized trioma liver cell which supports NANB infection in cell culture. The trioma cell line is prepared by fusing human liver cells with a mouse/human fusion partner selected for human chromosome stability. Cells containing the desired NANB viral agent can be identified by immunofluorescence methods, employing anti-ET-NANB human antibodies.

The viral agent is disrupted, prior to protein isolation, by conventional methods, which can include sonication, high- or low-salt conditions, or use of detergents.

Purification of ET-NANB viral protein can be carried out by affinity chromatography, using a purified anti-ET-NANB antibody attached according to standard methods to a suitable solid support. The antibody itself may be purified by affinity chromatography, where an immunoreactive recombinant ETNANB protein, such as described above, is attached to a solid support, for isolation of anti-ET-NANB antibodies from an immune serum source. The bound antibody is released from the support by standard methods.

Alternatively, the anti-ET-NANB antibody may be an antiserum or a monoclonal antibody (Mab) prepared by immunizing a mouse or other animal with recombinant ETNANB protein. For Mab production, lymphocytes are isolated from the animal and immortalized with a suitable fusion partner, and successful fusion products which react with the recombinant protein immunogen are selected. These in turn may be used in affinity purification procedures, described above, to obtain native ET-NANB antigen.

V. Utility

Although ET-NANB is primarily of interest because of its effects on humans, recent data has shown that this virus is also capable of infecting other animals, especially mammals. Accordingly, any discussion herein of utility applies to both human and veterinary uses, especially commercial veterinary uses, such as the diagnosis and treatment of pigs, cattle, sheep, horses, and other domesticated animals.

A. Diagnostic Methods

The particles and antigens of the invention, as well as the genetic material, can be used in diagnostic assays. Methods for detecting the presence of ET-NANB hepatitis comprise analyzing a biological sample such as a blood sample, stool sample or liver biopsy specimen for the presence of an analyte associated with ET-NANB hepatitis virus.

The analyte can be a nucleotide sequence which hybridizes with a probe comprising a sequence of at least about 16 consecutive nucleotides, usually 30 to 200 nucleotides, up to substantially the full sequence of the sequences shown above (cDNA sequences). The analyte can be RNA or cDNA. The analyte is typically a virus particle suspected of being ET-NANB or a particle for which this classification is being ruled out. The virus particle can be further characterized as having an RNA viral genome comprising a sequence at least about 70% homologous to a sequence of at least 12 consecutive nucleotides of the "forward" and "reverse" sequences given above, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Particularly preferred for use as a probe are sequences of consecutive nucleotides derived from the 406.3-2 and 406.4-2 clones described herein, since these clones appear to be particularly diagnostic for HEV.

The analyte can also comprise an antibody which recognizes an antigen, such as a cell surface antigen, on a ET-NANB virus particle. The analyte can also be a ET-NANB viral antigen. Where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by ET-NANB hepatitis virus or by assays that directly determine the presence of virus particles or antigens. Such techniques are well known and need not be described here in detail. Examples include both heterogeneous and homogeneous immunoassay techniques. Both techniques are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

When assaying for the presence of antibodies induced by ET-NANB viruses, the viruses and antigens of the invention can be used as specific binding agents to detect either IgG or IgM antibodies. Since IgM antibodies are typically the first antibodies that appear during the course of an infection, when IgG synthesis may not yet have been initiated, specifically distinguishing between IgM and IgG antibodies present in the blood stream of a host will enable a physician or other investigator to determine whether the infection is recent or convalescent. Proteins expressed by the 406.3-2 and 406.4-2 clones described herein and peptide fragments thereof are particularly preferred for use as specific binding agents to detect antibodies since they have been demonstrated to be reactive with a number of different human HEV sera. Further, they are reactive with both acute and convalescent sera.

In one diagnostic configuration, test serum is reacted with a solid phase reagent having surface-bound ET-NANB protein antigen. After binding anti-ET-NANB antibody to the reagent and removing unbound serum components by washing, the reagent is reacted with reporter-labeled anti-human antibody to bind reporter to the reagent in proportion to the amount of bound anti-ET-NANB antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or colorimetric substrate.

The solid surface reagent in the above assay prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined, either IgM (acute phase) or IgG (convalescent phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant protein antigen which is (a) immunoreactive with antibodies present in individuals infected with enterically transmitted nonA/nonB viral agent and (b) derived from a viral hepatitis agent whose genome contains a region which is homologous to the 1.33 kb DNA EcoRI insert present in plasmid pTZKF1(ET1.1) carried in *E. Coli* strain BB4, and having ATCC deposit no. 67717. A reporter-labeled anti-human antibody in the kit is used for detecting surface-bound anti-ET-NANB antibody.

B. Viral Genome Diagnostic Applications

The genetic material of the invention can itself be used in numerous assays as probes for genetic material present in naturally occurring infections. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers spaced apart from each other and based on the genetic sequence set forth above. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree-of-amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683, 195; and 4,683,202.

The invention includes a specific diagnostic method for determination of ET-NANB viral agent, based on selective amplification of ET-NANB fragments. This method employs a pair of single-strand primers derived from non-homologous regions of opposite strands of a DNA duplex fragment, which in turn is derived from an enterically transmitted viral hepatitis agent whose genome contains a region which is homologous to the 1.33 kb DNA EcoRI insert present in plasmid pTZKF1(ET1.1) carried in E. coli strain BB4, and having ATCC deposit no. 67717. These "primer fragments," which form one aspect of the invention, are prepared from ET-NANB fragments such as described in Section III above. The method follows the process for amplifying selected nucleic acid sequences as disclosed in U.S. Pat. No. 4,683,202, as discussed above.

C. Peptide Vaccine

Any of the antigens of the invention can be used in preparation of a vaccine. A preferred starting material for preparation of a vaccine is the particle antigen isolated from bile. The antigens are preferably initially recovered as intact particles as described above. However, it is also possible to prepare a suitable vaccine from particles isolated from other sources or non-particle recombinant antigens. When non-particle antigens are used (typically soluble antigens), proteins derived from the viral envelope or viral capsid are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet hemocyanin and the like. It is desirable, but not necessary, to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

A specific example of a vaccine composition includes, in a pharmacologically acceptable adjuvant, a recombinant protein or protein mixture derived from an enterically transmitted nonA/nonB viral hepatitis agent whose genome contains a region which is homologous to the 1.33 kb DNA EcoRI insert present in plasmid pTZKF1(ET1.1) carried in E. coli strain BB4, and having ATCC deposit no. 67717. The vaccine is administered at periodic intervals until a significant titer of anti-ET-NANB antibody is detected in the serum. The vaccine is intended to protect against ET-NANB infection.

Particularly preferred are vaccines prepared using proteins expressed by the 406.3-2 and 406.4-2 clones described herein and equivalents thereof, including fragments of the expressed proteins. Since these clones have already been demonstrated to be reactive with a variety of human HEV-positive sera, their utility in protecting against a variety of HEV strains is indicated.

D. Prophylactic and Therapeutic Antibodies and Antisera

In addition to use as a vaccine, the compositions can be used to prepare antibodies to ET-NANB virus particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the FC portion of a foreign species antibody or using an antibody of the same species as the host animal, for example, the use of antibodies from human/human hybridomas.

The antibodies can also be used as a means of enhancing the immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the ET-NANB virus particle can be passively administered alone or in conjunction with another anti-viral agent to a host infected with an ET-NANB virus to enhance the immune response and/or the effectiveness of an antiviral drug.

Alternatively, anti-ET-NANB-virus antibodies can be induced by administering anti-idiotype antibodies as immunogens. Conveniently, a purified anti-ET-NANB-virus antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-ET-NANB virus antibodies, or by affinity chromatography using anti-ET-NANB-virus antibodies bound to the affinity matrix. The anti-idiotype antibodies produced are similar in conformation to the authentic ET-NANB antigen and may be used to prepare an ET-NANB vaccine rather than using a ET-NANB particle antigen.

When used as a means of inducing anti-ET-NANB virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The anti-idiotype method of induction of anti-ET-NANB virus antibodies can alleviate problems which may be caused by passive administration of anti-ET-NANB-virus antibodies, such as an adverse immune response, and those associated with administration of purified blood components, such as infection with as yet undiscovered viruses.

The ET-NANB derived proteins of the invention are also intended for use in producing antiserum designed for pre- or post-exposure prophylaxis. Here an ET-NANB protein, or mixture of proteins is formulated with a suitable adjuvant and administered by injection to human volunteers, according to known methods for producing human antisera. Antibody response to the injected proteins is monitored, during a several-week period following immunization, by periodic serum sampling to detect the presence an anti-ET-NANB serum antibodies, as described in Section IIA above.

The antiserum from immunized individuals may be administered as a pre-exposure prophylactic measure for individuals who are at risk of contracting infection. The antiserum is also useful in treating an individual post-exposure, -analogous to the use of high titer antiserum against hepatitis B virus for post-exposure prophylaxis.

E. Monoclonal Antibodies

For both in vivo use of antibodies to ET-NANB virus particles and proteins and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a ET-NANB virus (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to ET-NANB virus particles. For monoclonal anti-idiotype antibodies, the antibodies must bind to anti-virus particle antibodies. Cells producing antibodies of the desired specificity are selected.

The following examples illustrate various aspects of the invention, but are in no way intended to limit the scope thereof.

Material

The materials used in the following Examples were as follows:

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I. from New England Biolabs (NEB, Beverly Mass.); and RNase A was obtained from Sigma (St. Louis, Mo.).

Other reagents: EcoRI linkers were obtained from NEB; and nitro blue tetrazolium (NBT), S-bromo-4-chloro-3-indolyl phosphate (BCIP) S-bromo-4-chloro-3-indolyl-B-D-galactopyranoside (Xgal) and isopropyl B-D-thiogalactopyranoside (IPTG) were obtained from Sigma.

cDNA synthesis kit and random priming labeling kits are available from Boehringer-Mannheim Biochemical (BMB, Indianapolis, Ind.).

EXAMPLE 1

Preparing cDNA Library

A. Source of ET-NANB virus

Two cynomolgus monkeys (cynos) were intravenously injected with a 10% suspension of a stool pool obtained from a second-passage cyno (cyno #37) infected with a strain of ET-NANB virus isolated from Burma cases whose stools were positive for ET-NANB, as evidenced by binding of 27–34 nm virus-like particles (VLPS) in the stool to immune serum from a known ETNANB patient. The animals developed elevated levels of alanine aminotransferase (ALT) between 24–36 days after inoculation, and one excreted 27–34 nm VLPs in its bile in the pre-acute phase of infection.

The bile duct of each infected animal was cannulated and about 1–3 cc of bile was collected daily. RNA was extracted from one bile specimen (cyno #121) by hot phenol extraction, using a standard RNA isolation procedure. Double-strand cDNA was formed from the isolated RNA by a random primer for first-strand generation, using a cDNA synthesis kit obtained from Boehringer-Mannheim (Indianapolis, Ind.).

B. Cloning the Duplex Fragments

The duplex cDNA fragments were blunt-ended with T4 DNA polymerase under standard conditions (Maniatis, p. 118), then extracted with phenol/chloroform and precipitated with ethanol. The blunt-ended material was ligated with EcoRI linkers under standard conditions (Maniatis, pp. 396–397) and digested with EcoRI to remove redundant linker ends. Non-ligated linkers were removed by sequential isopropanol precipitation.

Lambda gt10 phage vector (Huynh) was obtained from Promega Biotec (Madison, Wis.). This cloning vector has a unique EcoRI cloning site in the phage CI repressor gene. The cDNA fragments from above were introduced into the EcoRI site by mixing 0.5– 1.0 µg EcoRI-cleaved gt10, 0.5–3 µl of the above duplex fragments, 0.5 µl 10X ligation buffer, 0.5 µl ligase (200 units), and distilled water to 5 pl. The mixture was incubated overnight at 14° C., followed by in vitro packaging, according to standard methods (Maniatis, pp. 256–268).

The packaged phage were used to infect an E. coli hfl strain, such as strain HG415. Alternatively, E. coli, strain C600 hfl available from Promega Biotec, Madison, Wis., could be used. The percentage of recombinant plaques obtained with insertion of the EcoRI-ended fragments was less than 5% by analysis of 20 random plaques.

The resultant cDNA library was plated and phage were eluted from the selection plates by addition of elution buffer. After DNA extraction from the phage, the DNA was digested with EcoRI to release the heterogeneous insert population, and the DNA fragments were fractionated on agarose to remove phage fragments. The 500–4,000 basepair inserts were isolated and recloned into lambda gt10 as above, and the packaged phage was used to infect *E. coli* strain HG415. The percentage of successful recombinants was greater than 95%. The phage library was plated on *E. coli* strain HG415, at about 5,000 plaques/plate, on a total of 8 plates.

EXAMPLE 2

Selecting ET-NANB Cloned Fragments

A. cDNA Probes

Duplex cDNA fragments from noninfected and ETNANB-infected cynomolgus monkeys were prepared as in Example 1. The cDNA fragments were radiolabeled by random priming, using a random-priming labeling kit obtained from Boehringer-Mannheim (Indianapolis, Ind.).

B. Clone Selection

The plated cDNA library from Example 1 was transferred to each of two nitrocellulose filters, and the phage DNA was fixed on the filters by baking, according to standard methods (Maniatis, pp. 320–323). The duplicate filters were hybridized with either infected-source or control CDNA probes from above. Autoradiographs of the filters were examined to identify library clones which hybridized with radiolabeled CDNA probes from infected source only, i.e., did not hybridize with cDNA probes from the non-infected source. Sixteen such clones, out of a total of about 40,000 clones examined, were identified by this subtraction selection method.

Each of the sixteen clones was picked and replated at low concentration on an agar plate. The clones on each plate were transferred to two nitro-cellulose ag duplicate lifts, and examined for hybridization to radiolabeled cDNA probes from infected and noninfected sources, as above. Clones were selected which showed selective binding for infected-source probes (i.e., binding with infected-source probes and substantially no binding with non-infected-source probes). One of the clones which bound selectively to probe from infected source was isolated for further study. The selected vector was identified as lambda gt10-1.1, indicated in FIG. 1.

EXAMPLE 3

ET-NANB Sequence

Clone lambda gt10-1.1 from Example 2 was digested with EcoRI to release the heterologous insert, which was separated from the vector fragments by gel electrophoresis. The electrophoretic mobility of the fragment was consistent with a 1.33 kb fragment. This fragment, which contained EcoRI ends, was inserted into the EcoRI site of a pTZKF1 vector, whose construction and properties are described in co-owned U.S. patent application for "Cloning Vector System and Method for Rare Clone Identification", Serial No. 125, 650, filed Nov. 25, 1987, now abandoned. Briefly, and as illustrated in FIG. 1, this plasmid contains a unique EcoRI site adjacent a T7 polymerase promoter site, and plasmid and phage origins of replication. The sequence immediately adjacent each side of the EcoRI site is known. *E. coli* BB4 bacteria, obtained from Stratagene (La Jolla, Calif., were transformed with the plasmid.

Radiolabeled ET-NANB probe was prepared by excising the 1.33 kb insert from the lambda gt10-1.1 phage in Example 2, separating the fragment by gel electrophoresis, and randomly labeling as above. Bacteria transfected with the above pTZKF1 and containing the desired ET-NANB insert were selected by replica lift and hybridization with the radiolabeled ET-NANB probe, according to methods outlined in Example 2.

One bacterial colony containing a successful recombinant was used for sequencing a portion of the 1.33 kb insert. This isolate, designated pTZKF1(ET1.1), has been deposited with the American Type Culture Collection, and is identified by ATCC deposit no. 67717. Using a standard dideoxy sequencing procedure, and primers for the sequences flanking the EcoRI site, about 200–250 basepairs of sequence from the 5'-end region and 3'-end region of the insert were obtained. The sequences are given above in Section II. Later sequencing by the same techniques gave the full sequence in both directions, also given above.

EXAMPLE 4

Detecting ET-NANB Sequences cDNA fragment mixtures from the bile of noninfected and ET-NANB-infected cynomolgus monkeys were prepared as above. The cDNA fragments obtained from human stool samples were prepared as follows. Thirty ml of a 10% stool suspension obtained from an individual from Mexico diagnosed as infected with ET-NANB as a result of an ET-NANB outbreak, and a similar volume of stool from a healthy, non-infected individual, were layered over a 30% sucrose density gradient cushion, and centrifuged at 25,000×g for 6 hr in an SW27 rotor, at 15° C. The pelleted material from the infected-source stool contained 27–34 nm VLP particles characteristic of ET-NANB infection in the infected-stool sample. RNA was isolated from the sucrose-gradient pellets in both the infected and non-infected samples, and the isolated RNA was used to produce cDNA fragments as described in Example 1.

The cDNA fragment mixtures from infected and non-infected bile source, and from infected and non-infected human-stool source were each amplified by a novel linker/primer replication method described in co-owned patent application Ser. No. 07/208,512 for "DNA Amplification and Subtraction Technique," filed Jun. 17, 1988. Briefly, the fragments in each sample were blunt-ended with DNA Pol I then extracted with phenol/chloroform and precipitated with ethanol. The blunt-ended material was ligated with linkers having the following sequence (top or 5' sequence has SEQ ID NO.3; bottom or 3' sequence has SEQ ID NO:4):

5'-GGAATTCGCGGCCGCTCG-3'

3'-TTCCTTAAGCGCCGGCGAGC-5'

The duplex fragments were digested with NruI to remove linker dimers, mixed with a primer having the sequence represented by SEQ ID NO:3, and then heat denatured and cooled to room temperature to form single-strand DNA/primer complexes. The complexes were replicated to form duplex fragments by addition of *Thermus aquaticus* (Taq) polymerase and all four deoxynucleotides. The replication procedures, involving successive strand denaturation, formation of strand/primer complexes, and replication, was repeated 25 times.

Figure 2:
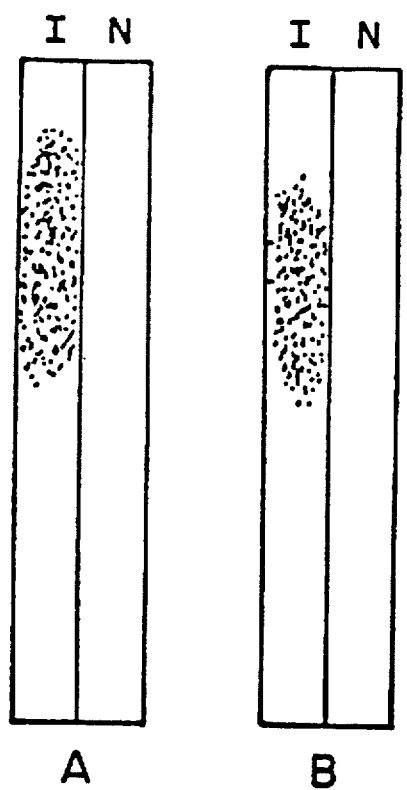
FIGS. 2A–2B are representations of Southern blots in which a radiolabeled ET-NANB probe was hybridized with amplified cDNA fragments prepared from RNA isolated from infected (I) and non-infected (N) bile sources (2A), and from infected (I) and non-infected (N) stool-sample sources (2B).

The amplified cDNA sequences were fractionated by agarose gel electrophoresis, using a 2% agarose matrix. After transfer of the DNA fragments from the agarose gels to nitrocellulose paper, the filters were hybridized to a random-labeled 32p probe prepared by (i) treating the pTZKF1(ET1.1) plasmid from above with EcoRI, (ii) isolating the released 1.33 kb ET-NANB fragment, and (iii) randomly labeling the isolated fragment. The probe hybridization was performed by conventional Southern blotting methods (Maniatis, pp. 382–389). FIG. 2 shows the hybridization pattern obtained with cDNAs from infected (I) and non-infected (N) bile sources (2A) and from infected (I) and noninfected (N) human stool sources (2B). As seen, the ET-NANB probe hybridized with fragments obtained from both of the infected sources, but was non-homologous to sequences obtained from either of the non-infected sources, thus confirming the specificity of derived sequence.

Southern blots of the radiolabeled 1.33 kb fragment with genomic DNA fragments from both human and cynomolgus-monkey DNA were also prepared. No probe hybridization to either of the genomic fragment mixtures was observed, confirming that the ET-NANB sequence is exogenous to either human or cynomolgus genome.

EXAMPLE 5

Expressing ET-NANB Proteins

A. Preparing ET-NANB Coding Sequences

The pTZKF1(ET1.1) plasmid from Example 2 was digested with EcoRI to release the 1.33 kb ET-NANB insert which was purified from the linearized plasmid by gel electrophoresis. The purified fragment was suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers as in Example 1. The resultant fragments were analyzed by electrophoresis (5–10V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 µl TE (0.01M Tris HCl, pH 7.5, 0.001M EDTA).

B. Cloning in an Expression Vector

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences (Example 5) or after amplification of cDNA (Example 4), were introduced into the EcoRI site by mixing 0.5–1.0 µg EcoRI-cleaved gt11, 0.3–3 µl of the above sized fragments, 0.5 µl 10X ligation buffer (above), 0.5 µl ligase (200 units), and distilled water to 5 µl. The mixture was incubated overnight at 14° C., followed by in vitro packaging, according to standard methods (Maniatis, pp. 256–268).

The packaged phage were used to infect E. coli strain KM392, obtained from Dr. Kevin Moore, DNAX (Palo Alto, Calif.). Alternatively, E. Coli strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for ET-NANB Recombinant Proteins

ET-NANB convalescent antiserum was obtained from patients infected during documented ET-NANB outbreaks in Mexico, Borneo, Pakistan, Somalia, and Burma. The sera were immunoreactive with VLPs in stool specimens from each of several other patients with ET-NANB hepatitis.

A lawn of E. coli KM392 cells infected with about 104 pfu of the phage stock from above was prepared on a 150 mm plate and incubated, inverted, for 5–8 hours at 37° C. The lawn was overlaid with a nitrocellulose sheet, causing transfer of expressed ETNANB recombinant protein from the plaques to the paper. The plate and filter were indexed for matching corresponding plate and filter positions.

The filter was washed twice in TBST buffer (10 mM Tris, pH 8.0, 150 mM NaCl, 0.05% TWEEN 20), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 µl NBT (50 mg/ml stock solution maintained at 4° C.) mixed with 16 µl BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the ET-NANB antibody. The identified plaques were picked and eluted in phage buffer (Maniatis, p. 443).

E. Epitope Identification

A series of subclones derived from the original pTZKF1 (ET1.1) plasmid from Example 2 were isolated using the same techniques described above. Each of these five subclones were immunoreactive with a pool of anti-ET antisera noted in C. The subclones contained short sequences from the "reverse" sequence set forth previously. The beginning and ending points of the sequences in the subclones (relative to the full "reverse" sequence), are identified in the table below.

TABLE 1

| | Position in "Reverse" Sequence | |
|---|---|---|
| Subclone | 5'-end | 3'-end |
| Y1 | 509 | 630 |
| Y2 | 581 | 654 |
| Y3 | 495 | 652 |
| Y4 | 545 | 739 |
| Y5 | 532 | 652 |

Since all of the gene sequences identified in the table must contain the coding sequence for the epitope, it is apparent that the coding sequence for the epitope falls in the region between nucleotide 581 (5'-end) and 630 (3'-end). Genetic sequences equivalent to and complementary to this relatively short sequence are therefore particularly preferred aspects of the present invention, as are peptides produced using this coding region.

A second series of clones identifying an altogether different epitope was isolated with only Mexican serum.

TABLE 2

| Subclone | Position in "Forward" Sequence | |
|---|---|---|
| | 5'-end | 3'-end |
| ET 2-2 | 1 | 156 |
| ET 8-3 | 1 | 98 |
| ET 9-1 | 1 | 72 |
| ET 13-1 | 1 | 64 |

The coding system for this epitope falls between nucleotide 1 (5'-end) and 64 (3'-end). Genetic sequences related to this short sequence are therefore also preferred, as are peptides produced using this coding region.

Two particularly preferred subclones for use in preparing polypeptides containing epitopes specific for HEV are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 3 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the Y2 clone identified in Table 1 above. Only one of the sera reacted with the polypeptide expressed by this clone. No immunoreactivity was seen for normal expression products of the gt11 vector.

TABLE 3

Immunoreactivity of HEV Recombinant Proteins: Human Sera

| Sera | Source | Stage[1] | 406.3-2 | 406.4-2 | Y2 | λgt11 |
|---|---|---|---|---|---|---|
| FVH-21 | Burma | A | − | − | − | − |
| FVH-8 | Burma | A | − | + | + | − |
| SOM-19 | Somalia | A | + | + | − | − |
| SOM-20 | Somalia | A | + | + | − | − |
| IM-35 | Borneo | A | + | + | − | − |
| IM-36 | Borneo | A | − | − | − | − |
| PAK-1 | Pakistan | A | + | + | − | − |
| FFI-4 | Mexico | A | + | + | − | − |
| FFI-125 | Mexico | A | − | + | − | − |
| F 387 IC | Mexico | C | + | + | ND | − |
| Normal | U.S.A. | | − | − | − | − |

[1]A = acute; C = convalenscent

While the invention has been described with reference to particular embodiments, methods, construction and use, it will be apparent to those skilled in the art that various changes and modifications can be made without departing from the invention.

We claim:

1. An isolated DNA comprising the genome of an enterically transmitted nonA/nonB (ET-NANB) viral hepatitis agent, said genome containing a region consisting of the sequence of the 1.33 kb DNA EcoRI insert present in plasmid pTZKF1(ET1.1) carried in *E. coli* strain BB4 and having ATCC deposit No. 67717, or a fragment of such isolated DNA, said fragment comprising a nucleotide residue sequence found only in an ET-NANB viral hepatitis agent.

2. The fragment of claim 1, wherein said fragment comprises the nucleotide residue sequence of the 1.33 kb DNA EcoRI insert present in plasmid pTZKF1(ET1.1) carried in *E. coli* strain BB4 and having ATCC deposit No. 67717.

3. An isolated DNA comprising the genome of an enterically transmitted nonA/nonB (ET-NANB) viral hepatitis agent, said genome comprising a region consisting of the sequence of the 1.33 kb DNA EcoRI insert present in plasmid pTZKF1(ET1.1) carried in *E. coli* strain BB4 and having ATCC deposit No. 67717, or a fragment of such isolated DNA, said fragment (i) being capable of selectively hybridizing to said genome, and (ii) having a length of at least 12 nucleotides.

4. The fragment of claim 3, wherein said fragment has a length of at least 14 nucleotides.

5. The fragment of claim 4, wherein said fragment has a length of at least 20 nucleotides.

6. The fragment of claim 5, wherein said fragment has a length of at least 30 nucleotides.

7. The fragment of claim 6, wherein said fragment has a length of at least 50 nucleotides.

8. The fragment of claim 7, wherein said fragment comprises the nucleotide residue sequence of the 1.33 kb DNA EcoRI insert present in plasmid pTZKF1(ET1.1) carried in *E. coli* strain BB4 and hating ATCC deposit No. 67717.

* * * * *

UNITED STATES PATENT AND TRADEMARK OFFICE
CERTIFICATE OF CORRECTION

PATENT NO : 5,789,559
DATED : August 4, 1998
INVENTOR(S) : Gregory R. Reyes et al.

It is certified that error appears in the above-identified patent and that said Letters Patent is hereby corrected as shown below:

Col. 1, line 20, insert -- This invention was made with Government support under contracts 17-90-C-0092 awarded by the Department of Defense and AI35400-01 awarded by the National Institutes of Health. The Government has certain rights in this invention.--

Col. 84, line 50, replace "hating" with --having--.

Signed and Sealed this

Eighteenth Day of May, 1999

Attest:

Q. TODD DICKINSON

*Attesting Officer*         *Acting Commissioner of Patents and Trademarks*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1295 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 1.33 kb EcoRI insert of ET1.1, forward sequence ( i x ) FEATURE:
        ( A ) NAME/KEY: CDS
        ( B ) LOCATION: 1..1293

( i x ) FEATURE:
        ( A ) NAME/KEY: CDS
        ( B ) LOCATION: 2..1294

( i x ) FEATURE:
        ( A ) NAME/KEY: CDS
        ( B ) LOCATION: 3..1295

( x i ) SEQUENCE DESCRIPTION: SEQ ID NO:1:

```
AGACCTGTCC  CTGTTGCAGC  TGTTCTACCA  CCCTGCCCCG  AGCTCGAACA  GGGCCTTCTC        6
TACCTGCCCC  AGGAGCTCAC  CACCTGTGAT  AGTGTCGTAA  CATTTGAATT  AACAGACATT       1 2
```

```
GTGCACTGCC GCATGGCCGC CCCGAGCCAG CGCAAGGCCG TGCTGTCCAC ACTCGTGGGC      18
CGCTACGGCG GTCGCACAAA GCTCTACAAT GCTTCCCACT CTGATGTTCG CGACTCTCTC      24
GCCCGTTTTA TCCCGGCCAT TGGCCCCGTA CAGGTTACAA CTTGTGAATT GTACGAGCTA      30
GTGGAGGCCA TGGTCGAGAA GGGCCAGGAT GGCTCCGCCG TCCTTGAGCT TGATCTTTGC      36
AACCGTGACG TGTCCAGGAT CACCTTCTTC CAGAAAGATT GTAACAAGTT CACCACAGGT      42
GAGACCATTG CCCATGGTAA AGTGGGCCAG GGCATCTCGG CCTGGAGCAA GACCTTCTGC      48
GCCCTCTTTG GCCCTTGGTT CCGCGCTATT GAGAAGGCTA TTCTGGCCCT GCTCCCTCAG      54
GGTGTGTTTT ACGGTGATGC CTTTGATGAC ACCGTCTTCT CGGCGGCTGT GGCCGCAGCA      60
AAGGCATCCA TGGTGTTTGA GAATGACTTT TCTGAGTTTG ACTCCACCCA GAATAACTTT      66
TCTCTGGGTC TAGAGTGTGC TATTATGGAG GAGTGTGGGA TGCCGCAGTG GCTCATCCGC      72
CTGTATCACC TTATAAGGTC TGCGTGGATC TTGCAGGCCC CGAAGGAGTC TCTGCGAGGG      78
TTTTGGAAGA AACACTCCGG TGAGCCCGGC ACTCTTCTAT GGAATACTGT CTGGAATATG      84
GCCGTTATTA CCCACTGTTA TGACTTCCGC GATTTCAGG TGGCTGCCTT TAAAGGTGAT       90
GATTCGATAG TGCTTTGCAG TGAGTATCGT CAGAGTCCAG GAGCTGCTGT CCTGATCGCC      96
GGCTGTGGCT TGAAGTTGAA GGTAGATTTC CGCCCGATCG GTTTGTATGC AGGTGTTGTG     102
GTGGCCCCCG GCCTTGGCGC GCTCCCTGAT GTTGTGCGCT TCGCCGGCCG GCTTACCGAG     108
AAGAATTGGG GCCCTGGCCC TGAGCGGGCG GAGCAGCTCC GCCTCGCTGT TAGTGATTTC     114
CTCCGCAAGC TCACGAATGT AGCTCAGATG TGTGTGGATG TTGTTTCCCG TGTTTATGGG     120
GTTTCCCCTG GACTCGTTCA TAACCTGATT GGCATGCTAC AGGCTGTTGC TGATGGCAAG     126
GCACATTTCA CTGAGTCAGT AAAACCAGTG CTCGA                                 129
```

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Arg Pro Val Pro Val Ala Ala Val Leu Pro Pro Cys Pro Glu Leu Glu
 1               5                  10                  15

Gln Gly Leu Leu Tyr Leu Pro Gln Glu Leu Thr Thr Cys Asp Ser Val
            20                  25                  30

Val Thr Phe Glu Leu Thr Asp Ile Val His Cys Arg Met Ala Ala Pro
        35                  40                  45

Ser Gln Arg Lys Ala Val Leu Ser Thr Leu Val Gly Arg Tyr Gly Gly
    50                  55                  60

Arg Thr Lys Leu Tyr Asn Ala Ser His Ser Asp Val Arg Asp Ser Leu
65                  70                  75                  80

Ala Arg Phe Ile Pro Ala Ile Gly Pro Val Gln Val Thr Thr Cys Glu
                85                  90                  95

Leu Tyr Glu Leu Val Glu Ala Met Val Glu Lys Gly Gln Asp Gly Ser
            100                 105                 110

Ala Val Leu Glu Leu Asp Leu Cys Asn Arg Asp Val Ser Arg Ile Thr
        115                 120                 125

Phe Phe Gln Lys Asp Cys Asn Lys Phe Thr Thr Gly Glu Thr Ile Ala
    130                 135                 140

His Gly Lys Val Gly Gln Gly Ile Ser Ala Trp Ser Lys Thr Phe Cys
```

|  | 145 |  |  |  | 150 |  |  |  | 155 |  |  |  | 160 |  |
|---|---|---|---|---|---|---|---|---|---|---|---|---|---|---|
| Ala | Leu | Phe | Gly | Pro 165 | Trp | Phe | Arg | Ala | Ile 170 | Glu | Lys | Ala | Ile 175 | Ala |
| Leu | Leu | Pro | Gln 180 | Gly | Val | Phe | Tyr | Gly 185 | Asp | Ala | Phe | Asp 190 | Thr | Val |
| Phe | Ser | Ala 195 | Ala | Val | Ala | Ala | Ala 200 | Lys | Ala | Ser | Met | Val 205 | Phe | Glu | Asn |
| Asp | Phe 210 | Ser | Glu | Phe | Asp | Ser 215 | Thr | Gln | Asn | Asn | Phe 220 | Ser | Leu | Gly | Leu |
| Glu 225 | Cys | Ala | Ile | Met | Glu 230 | Glu | Cys | Gly | Met | Pro 235 | Gln | Trp | Leu | Ile | Arg 240 |
| Leu | Tyr | His | Leu | Ile 245 | Arg | Ser | Ala | Trp | Ile 250 | Leu | Gln | Ala | Pro | Lys 255 | Glu |
| Ser | Leu | Arg | Gly 260 | Phe | Trp | Lys | Lys | His 265 | Ser | Gly | Glu | Pro | Gly 270 | Thr | Leu |
| Leu | Trp | Asn 275 | Thr | Val | Trp | Asn | Met 280 | Ala | Val | Ile | Thr | His 285 | Cys | Tyr | Asp |
| Phe | Arg 290 | Asp | Phe | Gln | Val | Ala 295 | Ala | Phe | Lys | Gly | Asp 300 | Asp | Ser | Ile | Val |
| Leu 305 | Cys | Ser | Glu | Tyr | Arg 310 | Gln | Ser | Pro | Gly | Ala 315 | Ala | Val | Leu | Ile | Ala 320 |
| Gly | Cys | Gly | Leu | Lys 325 | Leu | Lys | Val | Asp | Phe 330 | Arg | Pro | Ile | Gly | Leu 335 | Tyr |
| Ala | Gly | Val | Val 340 | Val | Ala | Pro | Gly | Leu 345 | Gly | Ala | Leu | Pro 350 | Asp | Val | Val |
| Arg | Phe | Ala 355 | Gly | Arg | Leu | Thr | Glu 360 | Lys | Asn | Trp | Gly | Pro 365 | Gly | Pro | Glu |
| Arg | Ala 370 | Glu | Gln | Leu | Arg | Leu 375 | Ala | Val | Ser | Asp | Phe 380 | Leu | Arg | Lys | Leu |
| Thr 385 | Asn | Val | Ala | Gln | Met 390 | Cys | Val | Asp | Val | Val 395 | Ser | Arg | Val | Tyr | Gly 400 |
| Val | Ser | Pro | Gly | Leu 405 | Val | His | Asn | Leu | Ile 410 | Gly | Met | Leu | Gln | Ala 415 | Val |
| Ala | Asp | Gly | Lys 420 | Ala | His | Phe | Thr | Glu 425 | Ser | Val | Lys | Pro | Val 430 | Leu |

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: linker - top (5') sequence ( x i ) SEQUENCE DESCRIPTION: SEQ ID NO:3:

GGAATTCGCG GCCGCTCG 15

( 2 ) INFORMATION FOR SEQ ID NO:4:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: linker - top (3') sequence (xi) SEQUENCE DESCRIPTION: SEQ ID NO:4:

| GGAGCGGCCG CGAAATTCCTT | 15 |

(2) INFORMATION FOR SEQ ID NO:5:

(i) SEQUENCE CHARACTERISTICS:
(A) LENGTH: 1295 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: 1.33 kb EcoRI insert of ET1.1, reverse sequence (xi) SEQUENCE DESCRIPTION: SEQ ID NO:5:

| TCGAGCACTG | GTTTTACTGA | CTCAGTGAAA | TGTGCCTTGC | CATCAGCAAC | AGCCTGTAGC | 60 |
| ATGCCAATCA | GGTTATGAAC | GAGTCCAGGG | GAAACCCCAT | AAACACGGGA | AACAACATCC | 120 |
| ACACACATCT | GAGCTACATT | CGTGAGCTTG | CGGAGGAAAT | CACTAACAGC | GAGGCGGAGC | 180 |
| TGCTCCGCCC | GCTCAGGGCC | AGGGCCCCAA | TTCTTCTCGG | TAAGCCGGCC | GGCGAAGCGC | 240 |
| ACAACATCAG | GGAGCGCGCC | AAGGCCGGGG | GCCACCACAA | CACCTGCATA | CAAACCGATC | 300 |
| GGGCGGAAAT | CTACCTTCAA | CTTCAAGCCA | CAGCCGGCGA | TCAGGACAGC | AGCTCCTGGA | 360 |
| CTCTGACGAT | ACTCACTGCA | AAGCACTATC | GAATCATCAC | CTTTAAAGGC | AGCCACCTGA | 420 |
| AAATCGCGGA | AGTCATAACA | GTGGGTAATA | ACGGCCATAT | TCCAGACAGT | ATTCCATAGA | 480 |
| AGAGTGCCGG | GCTCACCGGA | GTGTTTCTTC | CAAACCCTC | GCAGAGACTC | CTTCGGGGCC | 540 |
| TGCAAGATCC | ACGCAGACCT | TATAAGGTGA | TACAGGCGGA | TGAGCCACTG | CGGCATCCCA | 600 |
| CACTCCTCCA | TAATAGCACA | CTCTAGACCC | AGAGAAAAGT | TATTCTGGGT | GGAGTCAAAC | 660 |
| TCAGAAAAGT | CATTCTCAAA | CACCATGGAT | GCCTTTGCTG | CGGCCACAGC | CGCCGAGAAG | 720 |
| ACGGTGTCAT | CAAAGGCATC | ACCGTAAAAC | ACACCCTGAG | GGAGCAGGGC | CAGAATAGCC | 780 |
| TTCTCAATAG | CGCGGAACCA | AGGGCCAAAG | AGGGCGCAGA | AGGTCTTGCT | CCAGGCCGAG | 840 |
| ATGCCCTGGC | CCACTTTACC | ATGGGCAATG | GTCTCACCTG | TGGTGAACTT | GTTACAATCT | 900 |
| TTCTGGAAGA | AGGTGATCCT | GGACACGTCA | CGGTTGCAAA | GATCAAGCTC | AAGGACGGCG | 960 |
| GAGCCATCCT | GGCCCTTCTC | GACCATGGCC | TCCACTAGCT | CGTACAATTC | ACAAGTTGTA | 1020 |
| ACCTGTACGG | GGCCAATGGC | CGGGATAAsA | CGGGCGAGAG | AGTCGCGAAC | ATCAGAGTGG | 1080 |
| GAAGCATTGT | AGAGCTTTGT | GCGACCGCCG | TAGCGGCCCA | CGAGTGTGGA | CAGCACGGCC | 1140 |
| TTGCGCTGGC | TCGGGCGGC | CATGCGGCAG | TGCACAATGT | CTGTTAATTC | AAATGTTACG | 1200 |
| ACACTATCAC | AGGTGGTGAG | CTCCTGGGGC | AGGTAGAGAA | GGCCCTGTTC | GAGCTCGGGG | 1260 |

CAGGGTGGTA GAACAGCTGC AACAGGGACA GGTCT 1295

(2) INFORMATION FOR SEQ ID NO:6:

(i) SEQUENCE CHARACTERISTICS:
        (A) LENGTH: 7195 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HEV - Burma strain (ix) FEATURE:
        (A) NAME/KEY: CDS
        (B) LOCATION: 28..5106

(ix) FEATURE:
        (A) NAME/KEY: CDS
        (B) LOCATION: 5147..7126

(ix) FEATURE:
        (A) NAME/KEY: CDS
        (B) LOCATION: 5106..5474

(xi) SEQUENCE DESCRIPTION: SEQ ID NO:6:

```
AGGCAGAC

```
GACGAGTCGG CCCCCTGCCA TTGTAGGACC GCGATCCGTA AGGCGCTCTC AAAGTTTTGC  1440
TGCTTCATGA AGTGGCTTGG TCAGGAGTGC ACCTGCTTCC TTCAGCCTGC AGAAGGCGCC  1500
GTCGGCGACC AGGGTCATGA TAATGAAGCC TATGAGGGGT CCGATGTTGA CCCTGCTGAG  1560
TCCGCCATTA GTGACATATC TGGGTCCTAT GTCGTCCCTG GCACTGCCCT CCAACCGCTC  1620
TACCAGGCCC TCGATCTCCC CGCTGAGATT GTGGCTCGCG CGGGCCGGCT GACCGCCACA  1680
GTAAAGGTCT CCCAGGTCGA TGGGCGGATC GATTGCGAGA CCCTTCTTGG TAACAAAACC  1740
TTTCGCACGT CGTTCGTTGA CGGGGCGGTC TTAGAGACCA ATGGCCCAGA GCGCCACAAT  1800
CTCTCCTTCG ATGCCAGTCA GAGCACTATG GCCGCTGGCC CTTTCAGTCT CACCTATGCC  1860
GCCTCTGCAG CTGGGCTGGA GGTGCGCTAT GTTGCTGCCG GGCTTGACCA TCGGGCGGTT  1920
TTTGCCCCCG GTGTTTCACC CCGGTCAGCC CCCGGCGAGG TTACCGCCTT CTGCTCTGCC  1980
CTATACAGGT TTAACCGTGA GGCCCAGCGC CATTCGCTGA TCGGTAACTT ATGGTTCCAT  2040
CCTGAGGGAC TCATTGGCCT CTTCGCCCCG TTTTCGCCCG GCATGTTTG GGAGTCGGCT  2100
AATCCATTCT GTGGCGAGAG CACACTTTAC ACCCGTACTT GGTCGGAGGT TGATGCCGTC  2160
TCTAGTCCAG CCCGGCCTGA CTTAGGTTTT ATGTCTGAGC CTTCTATACC TAGTAGGGCC  2220
GCCACGCCTA CCCTGGCGGC CCCTCTACCC CCCCTGCAC CGGACCCTTC CCCCCCTCCC  2280
TCTGCCCCGG CGCTTGCTGA GCCGGCTTCT GGCGCTACCG CCGGGGCCCC GGCCATAACT  2340
CACCAGACGG CCCGGCACCG CCGCCTGCTC TTCACCTACC CGGATGGCTC TAAGGTATTC  2400
GCCGGCTCGC TGTTCGAGTC GACATGCACG TGGCTCGTTA ACGCGTCTAA TGTTGACCAC  2460
CGCCCTGGCG GCGGGCTTTG CCATGCATTT TACCAAAGGT ACCCCGCCTC CTTTGATGCT  2520
GCCTCTTTTG TGATGCGCGA CGGCGCGGCC GCGTACACAC TAACCCCCCG GCCAATAATT  258Q
CACGCTGTCG CCCCTGATTA TAGGTTGGAA CATAACCCAA AGAGGCTTGA GGCTGCTTAT  2640
CGGGAAACTT GCTCCCGCCT CGGCACCGCT GCATACCCGC TCCTCGGGAC CGGCATATAC  2700
CAGGTGCCGA TCGGCCCCAG TTTTGACGCC TGGGAGCGGA ACCACCGCCC CGGGGATGAG  2760
TTGTACCTTC CTGAGCTTGC TGCCAGATGG TTTGAGGCCA ATAGGCCGAC CCGCCCGACT  2820
CTCACTATAA CTGAGGATGT TGCACGGACA GCGAATCTGG CCATCGAGCT TGACTCAGCC  2880
ACAGATGTCG GCCGGGCCTG TGCCGGCTGT CGGGTCACCC CCGGCGTTGT TCAGTACCAG  2940
TTTACTGCAG GTGTGCCTGG ATCCGGCAAG TCCGCTCTA TCACCCAAGC CGATGTGGAC  3000
GTTGTCGTGG TCCCGACGCG TGAGTTGCGT AATGCCTGGC GCCGTCGCGG CTTTGCTGCT  3060
TTTACCCCGC ATACTGCCGC CAGAGTCACC CAGGGGCGCC GGGTTGTCAT TGATGAGGCT  3120
CCATCCCTCC CCCCTCACCT GCTGCTGCTC CACATGCAGC GGGCCGCCAC CGTCCACCTT  3180
CTTGGCGACC CGAACCAGAT CCCAGCCATC GACTTTGAGC ACGCTGGGCT CGTCCCCGCC  3240
ATCAGGCCCG ACTTAGGCCC CACCTCCTGG TGGCATGTTA CCCATCGCTG GCCTGCGGAT  3300
GTATGCGAGC TCATCCGTGG TGCATACCCC ATGATCCAGA CCACTAGCCG GGTTCTCCGT  3360
TCGTTGTTCT GGGGTGAGCC TGCCGTCGGG CAGAAACTAG TGTTCACCCA GGCGGCCAAG  3420
CCCGCCAACC CCGGCTCAGT GACGGTCCAC GAGGCGCAGG GCGCTACCTA CACGGAGACC  3480
ACTATTATTG CCACAGCAGA TGCCCGGGGC CTTATTCAGT CGTCTCGGGC TCATGCCATT  3540
GTTGCTCTGA CGCGCCACAC TGAGAAGTGC GTCATCATTG ACGCACCAGG CCTGCTTCGC  3600
GAGGTGGGCA TCTCCGATGC AATCGTTAAT AACTTTTTCC TCGCTGGTGG CGAAATTGGT  3660
CACCAGCGCC CATCAGTTAT TCCCCGTGGC AACCCTGACG CCAATGTTGA CACCCTGGCT  3720
GCCTTCCCGC CGTCTTGCCA GATTAGTGCC TTCCATCAGT TGGCTGAGGA GCTTGGCCAC  3780
```

-continued

| | | | | | | |
|---|---|---|---|---|---|---|
| AGACCTGTCC | CTGTTGCAGC | TGTTCTACCA | CCCTGCCCCG | AGCTCGAACA | GGGCCTTCTC | 3840 |
| TACCTGCCCC | AGGAGCTCAC | CACCTGTGAT | AGTGTCGTAA | CATTTGAATT | AACAGACATT | 3900 |
| GTGCACTGCC | GCATGGCCGC | CCCGAGCCAG | CGCAAGGCCG | TGCTGTCCAC | ACTCGTGGGC | 3960 |
| CGCTACGGCG | GTCGCACAAA | GCTCTACAAT | GCTTCCCACT | CTGATGTTCG | CGACTCTCTC | 4020 |
| GCCCGTTTTA | TCCCGGCCAT | TGGCCCCGTA | CAGGTTACAA | CTTGTGAATT | GTACGAGCTA | 4080 |
| GTGGAGGCCA | TGGTCGAGAA | GGGCCAGGAT | GGCTCCGCCG | TCCTTGAGCT | TGATCTTTGC | 4140 |
| AACCGTGACG | TGTCCAGGAT | CACCTTCTTC | CAGAAAGATT | GTAACAAGTT | CACCACAGGT | 4200 |
| GAGACCATTG | CCCATGGTAA | AGTGGGCCAG | GGCATCTCGG | CCTGGAGCAA | GACCTTCTGC | 4260 |
| GCCCTCTTTG | GCCCTTGGTT | CCGCGCTATT | GAGAAGGCTA | TTCTGGCCCT | GCTCCCTCAG | 4320 |
| GGTGTGTTTT | ACGGTGATGC | CTTTGATGAC | ACCGTCTTCT | CGGCGGCTGT | GGCCGCAGCA | 4380 |
| AAGGCATCCA | TGGTGTTTGA | GAATGACTTT | TCTGAGTTTG | ACTCCACCCA | GAATAACTTT | 4440 |
| TCTCTGGGTC | TAGAGTGTGC | TATTATGGAG | GAGTGTGGGA | TGCCGCAGTG | GCTCATCCGC | 4500 |
| CTGTATCACC | TTATAAGGTC | TGCGTGGATC | TTGCAGGCCC | CGAAGGAGTC | TCTGCGAGGG | 4560 |
| TTTTGGAAGA | AACACTCCGG | TGAGCCCGGC | ACTCTTCTAT | GGAATACTGT | CTGGAATATG | 4620 |
| GCCGTTATTA | CCCACTGTTA | TGACTTCCGC | GATTTCAGG | TGGCTGCCTT | TAAAGGTGAT | 4680 |
| GATTCGATAG | TGCTTTGCAG | TGAGTATCGT | CAGAGTCCAG | GAGCTGCTGT | CCTGATCGCC | 4740 |
| GGCTGTGGCT | TGAAGTTGAA | GGTAGATTTC | CGCCCGATCG | GTTTGTATGC | AGGTGTTGTG | 4800 |
| GTGGCCCCCG | GCCTTGGCGC | GCTCCCTGAT | GTTGTGCGCT | TCGCCGGCCG | GCTTACCGAG | 4860 |
| AAGAATTGGG | CCCTGGCCC | TGAGCGGGCG | GAGCAGCTCC | GCCTCGCTGT | TAGTGATTTC | 4920 |
| CTCCGCAAGC | TCACGAATGT | AGCTCAGATG | TGTGTGGATG | TTGTTTCCCG | TGTTTATGGG | 4980 |
| GTTCCCCTG | GACTCGTTCA | TAACCTGATT | GGCATGCTAC | AGGCTGTTGC | TGATGGCAAG | 5040 |
| GCACATTTCA | CTGAGTCAGT | AAAACCAGTG | CTCGACTTGA | CAAATTCAAT | CTTGTGTCGG | 5100 |
| GTGGAATGAA | TAACATGTCT | TTTGCTGCGC | CCATGGGTTC | GCGACCATGC | GCCCTCGGCC | 5160 |
| TATTTTGTTG | CTGCTCCTCA | TGTTTTTGCC | TATGCTGCCC | GCGCCACCGC | CCGGTCAGCC | 5220 |
| GTCTGGCCGC | CGTCGTGGGC | GGCGCAGCGG | CGGTTCCGGC | GGTGGTTTCT | GGGGTGACCG | 5280 |
| GGTTGATTCT | CAGCCCTTCG | CAATCCCCTA | TATTCATCCA | ACCAACCCCT | TCGCCCCCGA | 5340 |
| TGTCACCGCT | GCGGCCGGGG | CTGGACCTCG | TGTTCGCCAA | CCCGCCCGAC | CACTCGGCTC | 5400 |
| CGCTTGGCGT | GACCAGGCCC | AGCGCCCCGC | CGTTGCCTCA | CGTCGTAGAC | CTACCACAGC | 5460 |
| TGGGGCCGCG | CCGCTAACCG | CGGTCGCTCC | GGCCCATGAC | ACCCCGCCAG | TGCCTGATGT | 5520 |
| CGACTCCCGC | GGCGCCATCT | TGCGCCGGCA | GTATAACCTA | TCAACATCTC | CCCTTACCTC | 5580 |
| TTCCGTGGCC | ACCGGCACTA | ACCTGGTTCT | TTATGCCGCC | CCTCTTAGTC | CGCTTTTACC | 5640 |
| CCTTCAGGAC | GGCACCAATA | CCCATATAAT | GGCCACGGAA | GCTTCTAATT | ATGCCCAGTA | 5700 |
| CCGGGTTGCC | CGTGCCACAA | TCCGTTACCG | CCCGCTGGTC | CCCAATGCTG | TCGGCGGTTA | 5760 |
| CGCCATCTCC | ATCTCATTCT | GGCCACAGAC | CACCACCACC | CCGACGTCCG | TTGATATGAA | 5820 |
| TTCAATAACC | TCGACGGATG | TTCGTATTTT | AGTCCAGCCC | GGCATAGCCT | CTGAGCTTGT | 5880 |
| GATCCCAAGT | GAGCGCCTAC | ACTATCGTAA | CCAAGGCTGG | CGCTCCGTCG | AGACCTCTGG | 5940 |
| GGTGGCTGAG | GAGGAGGCTA | CCTCTGGTCT | TGTTATGCTT | TGCATACATG | GCTCACTCGT | 6000 |
| AAATTCCTAT | ACTAATACAC | CCTATACCGG | TGCCCTCGGG | CTGTTGGACT | TTGCCCTTGA | 6060 |
| GCTTGAGTTT | CGCAACCTTA | CCCCCGGTAA | CACCAATACG | CGGGTCTCCC | GTTATTCCAG | 6120 |
| CACTGCTCGC | CACCGCCTTC | GTCGCGGTGC | GGACGGGACT | GCCGAGCTCA | CCACCACGGC | 6180 |

```
TGCTACCCGC TTTATGAAGG ACCTCTATTT TACTAGTACT AATGGTGTCG GTGAGATCGG      6240

CCGCGGGATA GCCCTCACCC TGTTCAACCT TGCTGACACT CTGCTTGGCG GCCTGCCGAC      6300

AGAATTGATT TCGTCGGCTG GTGGCCAGCT GTTCTACTCC CGTCCCGTTG TCTCAGCCAA      6360

TGGCGAGCCG ACTGTTAAGT TGTATACATC TGTAGAGAAT GCTCAGCAGG ATAAGGGTAT      6420

TGCAATCCCG CATGACATTG ACCTCGGAGA ATCTCGTGTG GTTATTCAGG ATTATGATAA      6480

CCAACATGAA CAAGATCGGC CGACGCCTTC TCCAGCCCCA TCGCGCCCTT TCTCTGTCCT      6540

TCGAGCTAAT GATGTGCTTT GGCTCTCTCT CACCGCTGCC GAGTATGACC AGTCCACTTA      6600

TGGCTCTTCG ACTGGCCCAG TTTATGTTTC TGACTCTGTG ACCTTGGTTA ATGTTGCGAC      6660

CGGCGCGCAG GCCGTTGCCC GGTCGCTCGA TTGGACCAAG GTCACACTTG ACGGTCGCCC      6720

CCTCTCCACC ATCCAGCAGT ACTCGAAGAC CTTCTTTGTC CTGCCGCTCC GCGGTAAGCT      6780

CTCTTTCTGG GAGGCAGGCA CAACTAAAGC CGGGTACCCT TATAATTATA ACACCACTGC      6840

TAGCGACCAA CTGCTTGTCG AGAATGCCGC CGGGCACCGG GTCGCTATTT CCACTTACAC      6900

CACTAGCCTG GGTGCTGGTC CCGTCTCCAT TTCTGCGGTT GCCGTTTTAG CCCCCCACTC      6960

TGCGCTAGCA TTGCTTGAGG ATACCTTGGA CTACCCTGCC CGCGCCCATA CTTTTGATGA      7020

TTTCTGCCCA GAGTGCCGCC CCCTTGGCCT TCAGGGCTGC GCTTTCCAGT CTACTGTCGC      7080

TGAGCTTCAG CGCCTTAAGA TGAAGGTGGG TAAAACTCGG GAGTTGTAGT TTATTTGCTT      7140

GTGCCCCCCT TCTTTCTGTT GCTTATTTCT CATTTCTGCG TTCCGCGCTC CCTGA          7195
```

( 2 ) INFORMATION FOR SEQ ID NO:7:

( i ) SEQUENCE CHARACTERISTICS:
        ( A ) LENGTH: 1693 amino acids
        ( B ) TYPE: amino acid
        ( D ) TOPOLOGY: linear ( i i ) MOLECULE TYPE: Protein ( x i ) SEQUENCE DESCRIPTION: SEQ ID NO:7:

```
Met Glu Ala His Gln Phe Ile Lys Ala Pro Gly Ile Thr Thr Ala Ile
 1               5                  10                  15

Glu Gln Ala Ala Leu Ala Ala Ala Asn Ser Ala Leu Ala Asn Ala Val
                20                  25                  30

Val Val Arg Pro Phe Leu Ser His Gln Gln Ile Glu Ile Leu Ile Asn
            35                  40                  45

Leu Met Gln Pro Arg Gln Leu Val Phe Arg Pro Glu Val Phe Trp Asn
 50                  55                  60

His Pro Ile Gln Arg Val Ile His Asn Glu Leu Glu Leu Tyr Cys Arg
 65                  70                  75                  80

Ala Arg Ser Gly Arg Cys Leu Glu Ile Gly Ala His Pro Arg Ser Ile
                85                  90                  95

Asn Asp Asn Pro Asn Val Val His Arg Cys Phe Leu Arg Pro Val Gly
               100                 105                 110

Arg Asp Val Gln Arg Trp Tyr Thr Ala Pro Thr Arg Gly Pro Ala Ala
            115                 120                 125

Asn Cys Arg Arg Ser Ala Leu Arg Gly Leu Pro Ala Ala Asp Arg Thr
130                 135                 140

Tyr Cys Leu Asp Gly Phe Ser Gly Cys Agn Phe Pro Ala Glu Thr Gly
145                 150                 155                 160

Ile Ala Leu Tyr Ser Leu His Asp Met Ser Pro Ser Asp Val Ala Glu
                165                 170                 175

Ala Met Phe Arg His Gly Met Thr Arg Leu Tyr Ala Ala Leu His Leu
```

|     |     |     |     |     |     | 180 |     |     |     |     | 185 |     |     |     |     | 190 |     |     |     |
| --- | --- | --- | --- | --- | --- | --- | --- | --- | --- | --- | --- | --- | --- | --- | --- | --- | --- | --- | --- |
| Pro | Pro | Glu | Val | Leu | Leu | Pro | Pro | Gly | Thr | Tyr | Arg | Thr | Ala | Ser | Tyr |
|     |     | 195 |     |     |     |     | 200 |     |     |     |     | 205 |     |     |     |
| Leu | Leu | Ile | His | Asp | Gly | Arg | Val | Val | Val | Thr | Tyr | Glu | Gly | Asp |
|     | 210 |     |     |     |     | 215 |     |     |     |     | 220 |     |     |     |
| Thr | Ser | Ala | Gly | Tyr | Asn | His | Asp | Val | Ser | Asn | Leu | Arg | Ser | Trp | Ile |
| 225 |     |     |     |     | 230 |     |     |     |     | 235 |     |     |     |     | 240 |
| Arg | Thr | Thr | Lys | Val | Thr | Gly | Asp | His | Pro | Leu | Val | Ile | Glu | Arg | Val |
|     |     |     |     | 245 |     |     |     |     | 250 |     |     |     |     | 255 |     |
| Arg | Ala | Ile | Gly | Cys | His | Phe | Val | Leu | Leu | Thr | Ala | Ala | Pro | Glu |
|     |     |     | 260 |     |     |     |     | 265 |     |     |     |     | 270 |     |
| Pro | Ser | Pro | Met | Pro | Tyr | Val | Pro | Tyr | Pro | Arg | Ser | Thr | Glu | Val | Tyr |
|     |     | 275 |     |     |     |     | 280 |     |     |     |     | 285 |     |     |     |
| Val | Arg | Ser | Ile | Phe | Gly | Pro | Gly | Gly | Thr | Pro | Ser | Leu | Phe | Pro | Thr |
|     | 290 |     |     |     |     | 295 |     |     |     |     | 300 |     |     |     |     |
| Ser | Cys | Ser | Thr | Lys | Ser | Thr | Phe | His | Ala | Val | Pro | Ala | His | Ile | Trp |
| 305 |     |     |     |     | 310 |     |     |     |     | 315 |     |     |     |     | 320 |
| Asp | Arg | Leu | Met | Leu | Phe | Gly | Ala | Thr | Leu | Asp | Asp | Gln | Ala | Phe | Cys |
|     |     |     |     | 325 |     |     |     |     | 330 |     |     |     |     | 335 |     |
| Cys | Ser | Arg | Leu | Met | Thr | Tyr | Leu | Arg | Gly | Ile | Ser | Tyr | Lys | Val | Thr |
|     |     |     | 340 |     |     |     |     | 345 |     |     |     |     | 350 |     |     |
| Val | Gly | Thr | Leu | Val | Ala | Asn | Glu | Gly | Trp | Asn | Ala | Ser | Glu | Asp | Ala |
|     |     | 355 |     |     |     |     | 360 |     |     |     |     | 365 |     |     |     |
| Leu | Thr | Ala | Val | Ile | Thr | Ala | Ala | Tyr | Leu | Thr | Ile | Cys | His | Gln | Arg |
|     | 370 |     |     |     |     | 375 |     |     |     |     | 380 |     |     |     |     |
| Tyr | Leu | Arg | Thr | Gln | Ala | Ile | Ser | Lys | Gly | Met | Arg | Arg | Leu | Glu | Arg |
| 385 |     |     |     |     | 390 |     |     |     |     | 395 |     |     |     |     | 400 |
| Glu | His | Ala | Gln | Lys | Phe | Ile | Thr | Arg | Leu | Tyr | Ser | Trp | Leu | Phe | Glu |
|     |     |     |     | 405 |     |     |     |     | 410 |     |     |     |     | 415 |     |
| Lys | Ser | Gly | Arg | Asp | Tyr | Ile | Pro | Gly | Arg | Gln | Leu | Glu | Phe | Tyr | Ala |
|     |     |     | 420 |     |     |     |     | 425 |     |     |     |     | 430 |     |     |
| Gln | Cys | Arg | Arg | Trp | Leu | Ser | Ala | Gly | Phe | His | Leu | Asp | Pro | Arg | Val |
|     |     |     | 435 |     |     |     |     | 440 |     |     |     |     | 445 |     |     |
| Leu | Val | Phe | Asp | Glu | Ser | Ala | Pro | Cys | His | Cys | Arg | Thr | Ala | Ile | Arg |
|     | 450 |     |     |     |     | 455 |     |     |     |     | 460 |     |     |     |     |
| Lys | Ala | Leu | Ser | Lys | Phe | Cys | Cys | Phe | Met | Lys | Trp | Leu | Gly | Gln | Glu |
| 465 |     |     |     |     | 470 |     |     |     |     | 475 |     |     |     |     | 480 |
| Cys | Thr | Cys | Phe | Leu | Gln | Pro | Ala | Glu | Gly | Ala | Val | Gly | Asp | Gln | Gly |
|     |     |     |     | 485 |     |     |     |     | 490 |     |     |     |     | 495 |     |
| His | Asp | Asn | Glu | Ala | Tyr | Glu | Gly | Ser | Asp | Val | Asp | Pro | Ala | Glu | Ser |
|     |     |     | 500 |     |     |     |     | 505 |     |     |     |     | 510 |     |     |
| Ala | Ile | Ser | Asp | Ile | Ser | Gly | Ser | Tyr | Val | Val | Pro | Gly | Thr | Ala | Leu |
|     |     | 515 |     |     |     |     | 520 |     |     |     |     | 525 |     |     |     |
| Gln | Pro | Leu | Tyr | Gln | Ala | Leu | Asp | Leu | Pro | Ala | Glu | Ile | Val | Ala | Arg |
|     | 530 |     |     |     |     | 535 |     |     |     |     | 540 |     |     |     |     |
| Ala | Gly | Arg | Leu | Thr | Ala | Thr | Val | Lys | Val | Ser | Gln | Val | Asp | Gly | Arg |
| 545 |     |     |     |     | 550 |     |     |     |     | 555 |     |     |     |     | 560 |
| Ile | Asp | Cys | Glu | Thr | Leu | Leu | Gly | Asn | Lys | Thr | Phe | Arg | Thr | Ser | Phe |
|     |     |     |     | 565 |     |     |     |     | 570 |     |     |     |     | 575 |     |
| Val | Asp | Gly | Ala | Val | Leu | Glu | Thr | Asn | Gly | Pro | Glu | Arg | His | Asn | Leu |
|     |     |     | 580 |     |     |     |     | 585 |     |     |     |     | 590 |     |     |
| Ser | Phe | Asp | Ala | Ser | Gln | Ser | Thr | Met | Ala | Ala | Gly | Pro | Phe | Ser | Leu |
|     |     |     |     | 595 |     |     |     |     | 600 |     |     |     |     | 605 |     |

-continued

| | | | | | | | | | | | | | | |
|---|---|---|---|---|---|---|---|---|---|---|---|---|---|---|
| Thr | Tyr | Ala | Ala | Ser | Ala | Ala | Gly | Leu | Glu | Val | Arg | Tyr | Val | Ala | Ala |
| | 610 | | | | 615 | | | | | 620 | | | | | |
| Gly | Leu | Asp | His | Arg | Ala | Val | Phe | Ala | Pro | Gly | Val | Ser | Pro | Arg | Ser |
| 625 | | | | 630 | | | | | 635 | | | | | 640 | |
| Ala | Pro | Gly | Glu | Val | Thr | Ala | Phe | Cys | Ser | Ala | Leu | Tyr | Arg | Phe | Asn |
| | | | | 645 | | | | 650 | | | | | 655 | | |
| Arg | Glu | Ala | Gln | Arg | His | Ser | Leu | Ile | Gly | Asn | Leu | Trp | Phe | His | Pro |
| | | | 660 | | | | | 665 | | | | | 670 | | |
| Glu | Gly | Leu | Ile | Gly | Leu | Phe | Ala | Pro | Phe | Ser | Pro | Gly | His | Val | Trp |
| | | | 675 | | | | 680 | | | | | 685 | | | |
| Glu | Ser | Ala | Asn | Pro | Phe | Cys | Gly | Glu | Ser | Thr | Leu | Tyr | Thr | Arg | Thr |
| | | 690 | | | | 695 | | | | | 700 | | | | |
| Trp | Ser | Glu | Val | Asp | Ala | Val | Ser | Ser | Pro | Ala | Arg | Pro | Asp | Leu | Gly |
| 705 | | | | | 710 | | | | | 715 | | | | | 720 |
| Phe | Met | Ser | Glu | Pro | Ser | Ile | Pro | Ser | Arg | Ala | Ala | Thr | Pro | Thr | Leu |
| | | | | 725 | | | | | 730 | | | | | 735 | |
| Ala | Ala | Pro | Leu | Pro | Pro | Ala | Pro | Asp | Pro | Ser | Pro | Pro | Pro | Ser | |
| | | | 740 | | | | 745 | | | | | 750 | | | |
| Ala | Pro | Ala | Leu | Ala | Glu | Pro | Ala | Ser | Gly | Ala | Thr | Ala | Gly | Ala | Pro |
| | | 755 | | | | 760 | | | | | 765 | | | | |
| Ala | Ile | Thr | His | Gln | Thr | Ala | Arg | His | Arg | Arg | Leu | Phe | Thr | Tyr | |
| | 770 | | | | | 775 | | | | | 780 | | | | |
| Pro | Asp | Gly | Ser | Lys | Val | Phe | Ala | Gly | Ser | Leu | Phe | Glu | Ser | Thr | Cys |
| 785 | | | | | 790 | | | | | 795 | | | | | 800 |
| Thr | Trp | Leu | Val | Asn | Ala | Ser | Asn | Val | Asp | His | Arg | Pro | Gly | Gly | Gly |
| | | | | 805 | | | | | 810 | | | | | 815 | |
| Leu | Cys | His | Ala | Phe | Tyr | Gln | Arg | Tyr | Pro | Ala | Ser | Phe | Asp | Ala | Ala |
| | | | 820 | | | | | 825 | | | | | 830 | | |
| Ser | Phe | Val | Met | Arg | Asp | Gly | Ala | Ala | Tyr | Thr | Leu | Thr | Pro | Arg | |
| | | | 835 | | | | | 840 | | | | | 845 | | |
| Pro | Ile | Ile | His | Ala | Val | Ala | Pro | Asp | Tyr | Arg | Leu | Glu | His | Asn | Pro |
| | 850 | | | | | 855 | | | | | 860 | | | | |
| Lys | Arg | Leu | Glu | Ala | Ala | Tyr | Arg | Glu | Thr | Cys | Ser | Arg | Leu | Gly | Thr |
| 865 | | | | | 870 | | | | | 875 | | | | | 880 |
| Ala | Ala | Tyr | Pro | Leu | Leu | Gly | Thr | Gly | Ile | Tyr | Gln | Val | Pro | Ile | Gly |
| | | | | 885 | | | | | 890 | | | | | 895 | |
| Pro | Ser | Phe | Asp | Ala | Trp | Glu | Arg | Asn | His | Arg | Pro | Gly | Asp | Glu | Leu |
| | | | 900 | | | | | 905 | | | | | 910 | | |
| Tyr | Leu | Pro | Glu | Leu | Ala | Ala | Arg | Trp | Phe | Glu | Ala | Asn | Arg | Pro | Thr |
| | | 915 | | | | | 920 | | | | | 925 | | | |
| Arg | Pro | Thr | Leu | Thr | Ile | Thr | Glu | Asp | Val | Ala | Arg | Thr | Ala | Asn | Leu |
| | 930 | | | | | 935 | | | | | 940 | | | | |
| Ala | Ile | Glu | Leu | Asp | Ser | Ala | Thr | Asp | Val | Gly | Arg | Ala | Cys | Ala | Gly |
| 945 | | | | | 950 | | | | | 955 | | | | | 960 |
| Cys | Arg | Val | Thr | Pro | Gly | Val | Val | Gln | Tyr | Gln | Phe | Thr | Ala | Gly | Val |
| | | | | 965 | | | | | 970 | | | | | 975 | |
| Pro | Gly | Ser | Gly | Lys | Ser | Arg | Ser | Ile | Thr | Gln | Ala | Asp | Val | Asp | Val |
| | | | 980 | | | | | 985 | | | | | 990 | | |
| Val | Val | Val | Pro | Thr | Arg | Glu | Leu | Arg | Asn | Ala | Trp | Arg | Arg | Arg | Gly |
| | | 995 | | | | | 1000 | | | | | 1005 | | | |
| Phe | Ala | Ala | Phe | Thr | Pro | His | Thr | Ala | Ala | Arg | Val | Thr | Gln | Gly | Arg |
| | 1010 | | | | | 1015 | | | | | 1020 | | | | |
| Arg | Val | Val | Ile | Asp | Glu | Ala | Pro | Ser | Leu | Pro | Pro | His | Leu | Leu | Leu |
| 1025 | | | | | 1030 | | | | | 1035 | | | | | 1040 |

-continued

```
Leu His Met Gln Arg Ala Ala Thr Val His Leu Leu Gly Asp Pro Asn
             1045                1050                1055
Gln Ile Pro Ala Ile Asp Phe Glu His Ala Gly Leu Val Pro Ala Ile
             1060                1065                1070
Arg Pro Asp Leu Gly Pro Thr Ser Trp Trp His Val Thr His Arg Trp
             1075                1080                1085
Pro Ala Asp Val Cys Glu Leu Ile Arg Gly Ala Tyr Pro Met Ile Gln
             1090                1095                1100
Thr Thr Ser Arg Val Leu Arg Ser Leu Phe Trp Gly Glu Pro Ala Val
1105              1110                1115                1120
Gly Gln Lys Leu Val Phe Thr Gln Ala Ala Lys Pro Ala Asn Pro Gly
             1125                1130                1135
Ser Val Thr Val His Glu Ala Gln Gly Ala Thr Tyr Thr Glu Thr Thr
             1140                1145                1150
Ile Ile Ala Thr Ala Asp Ala Arg Gly Leu Ile Gln Ser Ser Arg Ala
             1155                1160                1165
His Ala Ile Val Ala Leu Thr Arg His Thr Glu Lys Cys Val Ile Ile
             1170                1175                1180
Asp Ala Pro Gly Leu Leu Arg Glu Val Gly Ile Ser Asp Ala Ile Val
1185              1190                1195                1200
Asn Asn Phe Phe Leu Ala Gly Gly Glu Ile Gly His Gln Arg Pro Ser
             1205                1210                1215
Val Ile Pro Arg Gly Asn Pro Asp Ala Asn Val Asp Thr Leu Ala Ala
             1220                1225                1230
Phe Pro Pro Ser Cys Gln Ile Ser Ala Phe His Gln Leu Ala Glu Glu
             1235                1240                1245
Leu Gly His Arg Pro Val Pro Val Ala Ala Val Leu Pro Pro Cys Pro
             1250                1255                1260
Glu Leu Glu Gln Gly Leu Leu Tyr Leu Pro Gln Glu Leu Thr Thr Cys
1265              1270                1275                1280
Asp Ser Val Val Thr Phe Glu Leu Thr Asp Ile Val His Cys Arg Met
             1285                1290                1295
Ala Ala Pro Ser Gln Arg Lys Ala Val Leu Ser Thr Leu Val Gly Arg
             1300                1305                1310
Tyr Gly Gly Arg Thr Lys Leu Tyr Asn Ala Ser His Ser Asp Val Arg
             1315                1320                1325
Asp Ser Leu Ala Arg Phe Ile Pro Ala Ile Gly Pro Val Gln Val Thr
             1330                1335                1340
Thr Cys Glu Leu Tyr Glu Leu Val Glu Ala Met Val Glu Lys Gly Gln
1345              1350                1355                1360
Asp Gly Ser Ala Val Leu Glu Leu Asp Leu Cys Asn Arg Asp Val Ser
             1365                1370                1375
Arg Ile Thr Phe Phe Gln Lys Asp Cys Asn Lys Phe Thr Thr Gly Glu
             1380                1385                1390
Thr Ile Ala His Gly Lys Val Gly Gln Gly Ile Ser Ala Trp Ser Lys
             1395                1400                1405
Thr Phe Cys Ala Leu Phe Gly Pro Trp Phe Arg Ala Ile Glu Lys Ala
             1410                1415                1420
Ile Leu Ala Leu Leu Pro Gln Gly Val Phe Tyr Gly Asp Ala Phe Asp
1425              1430                1435                1440
Asp Thr Val Phe Ser Ala Ala Val Ala Ala Ala Lys Ala Ser Met Val
             1445                1450                1455
Phe Glu Asn Asp Phe Ser Glu Phe Asp Ser Thr Gln Asn Asn Phe Ser
```

-continued

|   |   |   | 1460 |   |   |   |   | 1465 |   |   |   |   | 1470 |   |
|---|---|---|---|---|---|---|---|---|---|---|---|---|---|---|
| Leu | Gly | Leu | Glu | Cys | Ala | Ile | Met | Glu | Glu | Cys | Gly | Met | Pro | Gln | Trp |
|   |   |   | 1475 |   |   |   |   | 1480 |   |   |   |   | 1485 |   |
| Leu | Ile | Arg | Leu | Tyr | His | Leu | Ile | Arg | Ser | Ala | Trp | Ile | Leu | Gln | Ala |
|   |   |   | 1490 |   |   |   |   | 1495 |   |   |   |   | 1500 |   |
| Pro | Lys | Glu | Ser | Leu | Arg | Gly | Phe | Trp | Lys | Lys | His | Ser | Gly | Glu | Pro |
| 1505 |   |   |   |   | 1510 |   |   |   |   | 1515 |   |   |   |   | 1520 |
| Gly | Thr | Leu | Leu | Trp | Asn | Thr | Val | Trp | Asn | Met | Ala | Val | Ile | Thr | His |
|   |   |   |   | 1525 |   |   |   |   | 1530 |   |   |   |   | 1535 |   |
| Cys | Tyr | Asp | Phe | Arg | Asp | Phe | Gln | Val | Ala | Ala | Phe | Lys | Gly | Asp | Asp |
|   |   |   | 1540 |   |   |   |   | 1545 |   |   |   |   | 1550 |   |
| Ser | Ile | Val | Leu | Cys | Ser | Glu | Tyr | Arg | Gln | Ser | Pro | Gly | Ala | Ala | Val |
|   |   |   | 1555 |   |   |   |   | 1560 |   |   |   |   | 1565 |   |
| Leu | Ile | Ala | Gly | Cys | Gly | Leu | Lys | Leu | Lys | Val | Asp | Phe | Arg | Pro | Ile |
|   |   |   | 1570 |   |   |   |   | 1575 |   |   |   |   | 1580 |   |
| Gly | Leu | Tyr | Ala | Gly | Val | Val | Val | Ala | Pro | Gly | Leu | Gly | Ala | Leu | Pro |
| 1585 |   |   |   |   | 1590 |   |   |   |   | 1595 |   |   |   |   | 1600 |
| Asp | Val | Val | Arg | Phe | Ala | Gly | Arg | Leu | Thr | Glu | Lys | Asn | Trp | Gly | Pro |
|   |   |   |   | 1605 |   |   |   |   | 1610 |   |   |   |   | 1615 |   |
| Gly | Pro | Glu | Arg | Ala | Glu | Gln | Leu | Arg | Leu | Ala | Val | Ser | Asp | Phe | Leu |
|   |   |   | 1620 |   |   |   |   | 1625 |   |   |   |   | 1630 |   |
| Arg | Lys | Leu | Thr | Asn | Val | Ala | Gln | Met | Cys | Val | Asp | Val | Val | Ser | Arg |
|   |   |   | 1635 |   |   |   |   | 1640 |   |   |   |   | 1645 |   |
| Val | Tyr | Gly | Val | Ser | Pro | Gly | Leu | Val | His | Asn | Leu | Ile | Gly | Met | Leu |
|   |   |   | 1650 |   |   |   |   | 1655 |   |   |   |   | 1660 |   |
| Gln | Ala | Val | Ala | Asp | Gly | Lys | Ala | His | Phe | Thr | Glu | Ser | Val | Lys | Pro |
| 1665 |   |   |   |   | 1670 |   |   |   |   | 1675 |   |   |   |   | 1680 |
| Val | Leu | Asp | Leu | Thr | Asn | Ser | Ile | Leu | Cys | Arg | Val | Glu |
|   |   |   |   | 1685 |   |   |   |   | 1690 |   |

( 2 ) INFORMATION FOR SEQ ID NO:8:

( i ) SEQUENCE CHARACTERISTICS:
        ( A ) LENGTH: 660 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Arg | Pro | Arg | Pro | Ile | Leu | Leu | Leu | Leu | Met | Phe | Leu | Pro | Met |
|---|---|---|---|---|---|---|---|---|---|---|---|---|---|---|
| 1 |   |   |   | 5 |   |   |   |   | 10 |   |   |   |   | 15 |
| Leu | Pro | Ala | Pro | Pro | Gly | Gln | Pro | Ser | Gly | Arg | Arg | Arg | Gly | Arg |
|   |   |   | 20 |   |   |   |   | 25 |   |   |   |   | 30 |   |
| Arg | Ser | Gly | Gly | Ser | Gly | Gly | Gly | Phe | Trp | Gly | Asp | Arg | Val | Asp | Ser |
|   |   |   | 35 |   |   |   |   | 40 |   |   |   |   | 45 |   |
| Gln | Pro | Phe | Ala | Ile | Pro | Tyr | Ile | His | Pro | Thr | Asn | Pro | Phe | Ala | Pro |
|   |   | 50 |   |   |   |   | 55 |   |   |   |   | 60 |   |   |
| Asp | Val | Thr | Ala | Ala | Ala | Gly | Ala | Gly | Pro | Arg | Val | Arg | Gln | Pro | Ala |
| 65 |   |   |   |   | 70 |   |   |   |   | 75 |   |   |   |   | 80 |
| Arg | Pro | Leu | Gly | Ser | Ala | Trp | Arg | Asp | Gln | Ala | Gln | Arg | Pro | Ala | Val |
|   |   |   |   | 85 |   |   |   |   | 90 |   |   |   |   | 95 |   |
| Ala | Ser | Arg | Arg | Arg | Pro | Thr | Thr | Ala | Gly | Ala | Ala | Pro | Leu | Thr | Ala |
|   |   |   | 100 |   |   |   |   | 105 |   |   |   |   | 110 |   |
| Val | Ala | Pro | Ala | His | Asp | Thr | Pro | Pro | Val | Pro | Asp | Val | Asp | Ser | Arg |
|   |   |   | 115 |   |   |   |   | 120 |   |   |   |   | 125 |   |

```
Gly Ala Ile Leu Arg Arg Gln Tyr Asn Leu Ser Thr Ser Pro Leu Thr
    130                 135                 140
Ser Ser Val Ala Thr Gly Thr Asn Leu Val Leu Tyr Ala Ala Pro Leu
145                 150                 155                 160
Ser Pro Leu Leu Pro Leu Gln Asp Gly Thr Asn Thr His Ile Met Ala
                165                 170                 175
Thr Glu Ala Ser Asn Tyr Ala Gln Tyr Arg Val Ala Arg Ala Thr Ile
                180                 185                 190
Arg Tyr Arg Pro Leu Val Pro Asn Ala Val Gly Gly Tyr Ala Ile Ser
            195                 200                 205
Ile Ser Phe Trp Pro Gln Thr Thr Thr Thr Pro Thr Ser Val Asp Met
210                 215                 220
Asn Ser Ile Thr Ser Thr Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Ser Gly Val Ala Glu Glu Ala Thr
                260                 265                 270
Ser Gly Leu Val Met Leu Cys Ile His Gly Ser Leu Val Asn Ser Tyr
            275                 280                 285
Thr Asn Thr Pro Tyr Thr Gly Ala Leu Gly Leu Leu Asp Phe Ala Leu
290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
                325                 330                 335
Gly Thr Ala Glu Leu Thr Thr Thr Ala Ala Thr Arg Phe Met Lys Asp
                340                 345                 350
Leu Tyr Phe Thr Ser Thr Asn Gly Val Gly Glu Ile Gly Arg Gly Ile
            355                 360                 365
Ala Leu Thr Leu Phe Asn Leu Ala Asp Thr Leu Leu Gly Gly Leu Pro
370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
            435                 440                 445
Gln Asp Arg Pro Thr Pro Ser Pro Ala Pro Ser Arg Pro Phe Ser Val
450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
                500                 505                 510
Ser Leu Asp Trp Thr Lys Val Thr Leu Asp Gly Arg Pro Leu Ser Thr
            515                 520                 525
Ile Gln Gln Tyr Ser Lys Thr Phe Phe Val Leu Pro Leu Arg Gly Lys
530                 535                 540
Leu Ser Phe Trp Glu Ala Gly Thr Thr Lys Ala Gly Tyr Pro Tyr Asn
545                 550                 555                 560
```

| Tyr | Asn | Thr | Thr | Ala | Ser | Asp | Gln | Leu | Leu | Val | Glu | Asn | Ala | Ala | Gly |
| | | | | 565 | | | | 570 | | | | | | 575 | |

| His | Arg | Val | Ala | Ile | Ser | Thr | Tyr | Thr | Thr | Ser | Leu | Gly | Ala | Gly | Pro |
| | | | 580 | | | | | 585 | | | | | | 590 | |

| Val | Ser | Ile | Ser | Ala | Val | Ala | Val | Leu | Ala | Pro | His | Ser | Ala | Leu | Ala |
| | | 595 | | | | | 600 | | | | | 605 | | | |

| Leu | Leu | Glu | Asp | Thr | Leu | Asp | Tyr | Pro | Ala | Arg | Ala | His | Thr | Phe | Asp |
| | 610 | | | | | 615 | | | | | 620 | | | | |

| Asp | Phe | Cys | Pro | Glu | Cys | Arg | Pro | Leu | Gly | Leu | Gln | Gly | Cys | Ala | Phe |
| 625 | | | | | 630 | | | | | 635 | | | | | 640 |

| Gln | Ser | Thr | Val | Ala | Glu | Leu | Gln | Arg | Leu | Lys | Met | Lys | Val | Gly | Lys |
| | | | | 645 | | | | | 650 | | | | | 655 | |

| Thr | Arg | Glu | Leu |
| | | | 660 |

( 2 ) INFORMATION FOR SEQ ID NO:9:

( i ) SEQUENCE CHARACTERISTICS:
        ( A ) LENGTH: 123 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Asn | Asn | Met | Ser | Phe | Ala | Ala | Pro | Met | Gly | Ser | Arg | Pro | Cys | Ala |
| 1 | | | | 5 | | | | | 10 | | | | | 15 | |

| Leu | Gly | Leu | Phe | Cys | Cys | Cys | Ser | Ser | Cys | Phe | Cys | Leu | Cys | Cys | Pro |
| | | | 20 | | | | | 25 | | | | | 30 | | |

| Arg | His | Arg | Pro | Val | Ser | Arg | Leu | Ala | Ala | Val | Val | Gly | Gly | Ala | Ala |
| | | 35 | | | | | 40 | | | | | 45 | | | |

| Ala | Val | Pro | Ala | Val | Val | Ser | Gly | Val | Thr | Gly | Leu | Ile | Leu | Ser | Pro |
| | 50 | | | | | 55 | | | | | 60 | | | | |

| Ser | Gln | Ser | Pro | Ile | Phe | Ile | Gln | Pro | Thr | Pro | Ser | Pro | Pro | Met | Ser |
| 65 | | | | | 70 | | | | | 75 | | | | | 80 |

| Pro | Leu | Arg | Pro | Gly | Leu | Asp | Leu | Val | Phe | Ala | Asn | Pro | Pro | Asp | His |
| | | | | 85 | | | | | 90 | | | | | 95 | |

| Ser | Ala | Pro | Leu | Gly | Val | Thr | Arg | Pro | Ser | Ala | Pro | Pro | Leu | Pro | His |
| | | | 100 | | | | | 105 | | | | | 110 | | |

| Val | Val | Asp | Leu | Pro | Gln | Leu | Gly | Pro | Arg | Arg |
| | | 115 | | | | | 120 | | | |

( 2 ) INFORMATION FOR SEQ ID NO:10:

( i ) SEQUENCE CHARACTERISTICS:
        ( A ) LENGTH: 7171 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Composite Mexico strain ( x i ) SEQUENCE DESCRIPTION: SEQ ID NO:10:

```
GCCATGGAGG  CCCACCAGTT  CATTAAGGCT  CCTGGCATCA  CTACTGCTAT  TGAGCAAGCA     60
```

-continued

| | | | | | |
|---|---|---|---|---|---|
| GCTCTAGCAG | CGGCCAACTC | CGCCCTTGCG | AATGCTGTGG | TGGTCCGGCC | TTTCCTTTCC | 120 |
| CATCAGCAGG | TTGAGATCCT | TATAAATCTC | ATGCAACCTC | GGCAGCTGGT | GTTTCGTCCT | 180 |
| GAGGTTTTTT | GGAATCACCC | GATTCAACGT | GTTATACATA | ATGAGCTTGA | GCAGTATTGC | 240 |
| CGTGCTCGCT | CGGGTCGCTG | CCTTGAGATT | GGAGCCCACC | CACGCTCCAT | TAATGATAAT | 300 |
| CCTAATGTCC | TCCATCGCTG | CTTTCTCCAC | CCCGTCGGCC | GGGATGTTCA | GCGCTGGTAC | 360 |
| ACAGCCCCGA | CTAGGGGACC | TGCGGCGAAC | TGTCGCCGCT | CGGCACTTCG | TGGTCTGCCA | 420 |
| CCAGCCGACC | GCACTTACTG | TTTTGATGGC | TTTGCCGGCT | GCCGTTTTGC | CGCCGAGACT | 480 |
| GGTGTGGCTC | TCTATTCTCT | CCATGACTTG | CAGCCGGCTG | ATGTTGCCGA | GGCGATGGCT | 540 |
| CGCCACGGCA | TGACCCGCCT | TTATGCAGCT | TTCCACTTGC | CTCCAGAGGT | GCTCCTGCCT | 600 |
| CCTGGCACCT | ACCGGACATC | ATCCTACTTG | CTGATCCACG | ATGGTAAGCG | CGCGGTTGTC | 660 |
| ACTTATGAGG | GTGACACTAG | CGCCGGTTAC | AATCATGATG | TTGCCACCCT | CCGCACATGG | 720 |
| ATCAGGACAA | CTAAGGTTGT | GGGTGAACAC | CCTTGGTGA | TCGAGCGGGT | GCGGGGTATT | 780 |
| GGCTGTCACT | TTGTGTTGTT | GATCACTGCG | GCCCCTGAGC | CCTCCCCGAT | GCCCTACGTT | 840 |
| CCTTACCCGC | GTTCGACGGA | GGTCTATGTC | CGGTCTATCT | TTGGGCCCGG | CGGGTCCCCG | 900 |
| TCGCTGTTCC | CGACCGCTTG | TGCTGTCAAG | TCCACTTTTC | ACGCCGTCCC | CACGCACATC | 960 |
| TGGGACCGTC | TCATGCTCTT | TGGGGCCACC | CTCGACGACC | AGGCCTTTTG | CTGCTCCAGG | 1020 |
| CTTATGACGT | ACCTTCGTGG | CATTAGCTAT | AAGGTAACTG | TGGGTGCCCT | GGTCGCTAAT | 1080 |
| GAAGGCTGGA | ATGCCACCGA | GGATGCGCTC | ACTGCAGTTA | TTACGGCGGC | TTACCTCACA | 1140 |
| ATATGTCATC | AGCGTTATTT | GCGGACCCAG | GCGATTTCTA | AGGGCATGCG | CCGGCTTGAG | 1200 |
| CTTGAACATG | CTCAGAAATT | TATTTCACGC | CTCTACAGCT | GGCTATTTGA | GAAGTCAGGT | 1260 |
| CGTGATTACA | TCCCAGGCCG | CCAGCTGCAG | TTCTACGCTC | AGTGCCGCCG | CTGGTTATCT | 1320 |
| GCCGGGTTCC | ATCTCGACCC | CCGCACCTTA | GTTTTGATG | AGTCAGTGCC | TTGTAGCTGC | 1380 |
| CGAACCACCA | TCCGGCGGAT | CGCTGGAAAA | TTTTGCTGTT | TATGAAGTG | GCTCGGTCAG | 1440 |
| GAGTGTTCTT | GTTTCCTCCA | GCCCGCCGAG | GGGCTGGCGG | GCGACCAAGG | TCATGACAAT | 1500 |
| GAGGCCTATG | AAGGCTCTGA | TGTTGATACT | GCTGAGCCTG | CCACCCTAGA | CATTACAGGC | 1560 |
| TCATACATCG | TGGATGGTCG | GTCTCTGCAA | ACTGTCTATC | AAGCTCTCGA | CCTGCCAGCT | 1620 |
| GACCTGGTAG | CTCGCGCAGC | CCGACTGTCT | GCTACAGTTA | CTGTTACTGA | AACCTCTGGC | 1680 |
| CGTCTGGATT | GCCAAACAAT | GATCGGCAAT | AAGACTTTTC | TCACTACCTT | TGTTGATGGG | 1740 |
| GCACGCCTTG | AGGTTAACGG | GCCTGAGCAG | CTTAACCTCT | CTTTTGACAG | CCAGCAGTGT | 1800 |
| AGTATGGCAG | CCGGCCCGTT | TTGCCTCACC | TATGCTGCCG | TAGATGGCGG | GCTGGAAGTT | 1860 |
| CATTTTTCCA | CCGCTGGCCT | CGAGAGCCGT | GTTGTTTCC | CCCTGGTAA | TGCCCCGACT | 1920 |
| GCCCCGCCGA | GTGAGGTCAC | CGCCTTCTGC | TCAGCTCTTT | ATAGGCACAA | CCGGCAGAGC | 1980 |
| CAGCGCCAGT | CGGTTATTGG | TAGTTTGTGG | CTGCACCCTG | AAGGTTTGCT | CGGCCTGTTC | 2040 |
| CCGCCCTTTT | CACCCGGGCA | TGAGTGGCGG | TCTGCTAACC | CATTTGCGG | CGAGAGCACG | 2100 |
| CTCTACACCC | GCACTTGGTC | CACAATTACA | GACACACCCT | TAACTGTCGG | GCTAATTTCC | 2160 |
| GGTCATTTGG | ATGCTGCTCC | CCACTCGGGG | GGGCCACCTG | CTACTGCCAC | AGGCCCTGCT | 2220 |
| GTAGGCTCGT | CTGACTCTCC | AGACCCTGAC | CCGCTACCTG | ATGTTACAGA | TGGCTCACGC | 2280 |
| CCCTCTGGGG | CCCGTCCGGC | TGGCCCCAAC | CCGAATGGCG | TTCCGCAGCG | CCGCTTACTA | 2340 |
| CACACCTACC | CTGACGGCGC | TAAGATCTAT | GTCGGCTCCA | TTTTCGAGTC | TGAGTGCACC | 2400 |
| TGGCTTGTCA | ACGCATCTAA | CGCCGGCCAC | CGCCCTGGTG | GCGGGCTTTG | TCATGCTTTT | 2460 |

-continued

```
TTTCAGCGTT  ACCCTGATTC  GTTTGACGCC  ACCAAGTTTG  TGATGCGTGA  TGGTCTTGCC   2520
GCGTATACCC  TTACACCCCG  GCCGATCATT  CATGCGGTGG  CCCCGGACTA  TCGATTGGAA   2580
CATAACCCCA  AGAGGCTCGA  GGCTGCCTAC  CGCGAGACTT  GCGCCCGCCG  AGGCACTGCT   2640
GCCTATCCAC  TCTTAGGCGC  TGGCATTTAC  CAGGTGCCTG  TTAGTTTGAG  TTTTGATGCC   2700
TGGGAGCGGA  ACCACCGCCC  GTTTGACGAG  CTTTACCTAA  CAGAGCTGGC  GGCTCGGTGG   2760
TTTGAATCCA  ACCGCCCCGG  TCAGCCCACG  TTGAACATAA  CTGAGGATAC  CGCCCGTGCG   2820
GCCAACCTGG  CCCTGGAGCT  TGACTCCGGG  AGTGAAGTAG  GCCGCGCATG  TGCCGGGTGT   2880
AAAGTCGAGC  CTGGCGTTGT  GCGGTATCAG  TTTACAGCCG  GTGTCCCCGG  CTCTGGCAAG   2940
TCAAAGTCCG  TGCAACAGGC  GGATGTGGAT  GTTGTTGTTG  TGCCCACTCG  CGAGCTTCGG   3000
AACGCTTGGC  GGCGCCGGGG  CTTTGCGGCA  TTCACTCCGC  ACACTGCGGC  CCGTGTCACT   3060
AGCGGCCGTA  GGGTTGTCAT  TGATGAGGCC  CCTTCGCTCC  CCCACACTT   GCTGCTTTTA   3120
CATATGCAGC  GTGCTGCATC  TGTGCACCTC  CTTGGGGACC  CGAATCAGAT  CCCCGCCATA   3180
GATTTGAGC   ACACCGGTCT  GATTCCAGCA  ATACGGCCGG  AGTTGGTCCC  GACTTCATGG   3240
TGGCATGTCA  CCCACCGTTG  CCCTGCAGAT  GTCTGTGAGT  TAGTCCGTGG  TGCTTACCCT   3300
AAAATCCAGA  CTACAAGTAA  GGTGCTCCGT  TCCCTTTTCT  GGGGAGAGCC  AGCTGTCGGC   3360
CAGAAGCTAG  TGTTCACACA  GGCTGCTAAG  GCCGCGCACC  CCGGATCTAT  AACGGTCCAT   3420
GAGGCCCAGG  GTGCCACTTT  TACCACTACA  ACTATAATTG  CAACTGCAGA  TGCCCGTGGC   3480
CTCATACAGT  CCTCCCGGGC  TCACGCTATA  GTTGCTCTCA  CTAGGCATAC  TGAAAAATGT   3540
GTTATACTTG  ACTCTCCCGG  CCTGTTGCGT  GAGGTGGGTA  TCTCAGATGC  CATTGTTAAT   3600
AATTTCTTCC  TTTCGGGTGG  CGAGGTTGGT  CACCAGAGAC  CATCGGTCAT  TCCGCGAGGC   3660
AACCCTGACC  GCAATGTTGA  CGTGCTTGCG  GCGTTTCCAC  CTTCATGCCA  AATAAGCGCC   3720
TTCCATCAGC  TTGCTGAGGA  GCTGGGCCAC  CGGCCGGCGC  CGGTGGCGGC  TGTGCTACCT   3780
CCCTGCCCTG  AGCTTGAGCA  GGGCCTTCTC  TATCTGCCAC  AGGAGCTAGC  CTCCTGTGAC   3840
AGTGTTGTGA  CATTTGAGCT  AACTGACATT  GTGCACTGCC  GCATGGCGGC  CCCTAGCCAA   3900
AGGAAAGCTG  TTTTGTCCAC  GCTGGTAGGC  CGGTATGGCA  GACGCACAAG  GCTTTATGAT   3960
GCGGGTCACA  CCGATGTCCG  CGCCTCCCTT  GCGCGCTTTA  TTCCCACTCT  CGGGCGGGTT   4020
ACTGCCACCA  CCTGTGAACT  CTTTGAGCTT  GTAGAGGCGA  TGGTGGAGAA  GGGCCAAGAC   4080
GGTTCAGCCG  TCCTCGAGTT  GGATTTGTGC  AGCCGAGATG  TCTCCCGCAT  AACCTTTTTC   4140
CAGAAGGATT  GTAACAAGTT  CACGACCGGC  GAGACAATTG  CGCATGGCAA  AGTCGGTCAG   4200
GGTATCTTCC  GCTGGAGTAA  GACGTTTTGT  GCCCTGTTTG  GCCCCTGGTT  CCGTGCGATT   4260
GAGAAGGCTA  TTCTATCCCT  TTTACCACAA  GCTGTGTTCT  ACGGGGATGC  TTATGACGAC   4320
TCAGTATTCT  CTGCTGCCGT  GGCTGGCGCC  AGCCATGCCA  TGGTGTTTGA  AAATGATTTT   4380
TCTGAGTTTG  ACTCGACTCA  GAATAACTTT  TCCCTAGGTC  TTGAGTGCGC  CATTATGGAA   4440
GAGTGTGGTA  TGCCCCAGTG  GCTTGTCAGG  TTGTACCATG  CCGTCCGGTC  GGCGTGGATC   4500
CTGCAGGCCC  CAAAAGAGTC  TTTGAGAGGG  TTCTGGAAGA  AGCATTCTGG  TGAGCCGGGC   4560
AGCTTGCTCT  GGAATACGGT  GTGGAACATG  GCAATCATTG  CCCATTGCTA  TGAGTTCCGG   4620
GACCTCCAGG  TTGCCGCCTT  CAAGGGCGAC  GACTCGGTCG  TCCTCTGTAG  TGAATACCGC   4680
CAGAGCCCAG  GCGCCGGTTC  GCTTATAGCA  GGCTGTGGTT  TGAAGTTGAA  GGCTGACTTC   4740
CGGCCGATTG  GGCTGTATGC  CGGGGTTGTC  GTCGCCCCGG  GGCTCGGGGC  CCTACCCGAT   4800
GTCGTTCGAT  TCGCCGGACG  GCTTTCGGAG  AAGAACTGGG  GGCCTGATCC  GGAGCGGGCA   4860
```

-continued

| | | | | | |
|---|---|---|---|---|---|
| GAGCAGCTCC | GCCTCGCCGT | GCAGGATTTC | CTCCGTAGGT | TAACGAATGT | GGCCCAGATT | 4920 |
| TGTGTTGAGG | TGGTGTCTAG | AGTTTACGGG | GTTTCCCCGG | GTCTGGTTCA | TAACCTGATA | 4980 |
| GGCATGCTCC | AGACTATTGG | TGATGGTAAG | GCGCATTTTA | CAGAGTCTGT | TAAGCCTATA | 5040 |
| CTTGACCTTA | CACACTCAAT | TATGCACCGG | TCTGAATGAA | TAACATGTGG | TTTGCTGCGC | 5100 |
| CCATGGGTTC | GCCACCATGC | GCCCTAGGCC | TCTTTTGCTG | TTGTTCCTCT | TGTTTCTGCC | 5160 |
| TATGTTGCCC | GCGCCACCGA | CCGGTCAGCC | GTCTGGCCGC | CGTCGTGGGC | GGCGCAGCGG | 5220 |
| CGGTACCGGC | GGTGGTTTCT | GGGGTGACCG | GGTTGATTCT | CAGCCCTTCG | CAATCCCCTA | 5280 |
| TATTCATCCA | ACCAACCCCT | TTGCCCCAGA | CGTTGCCGCT | GCGTCCGGGT | CTGGACCTCG | 5340 |
| CCTTCGCCAA | CCAGCCCGGC | CACTTGGCTC | CACTTGGCGA | GATCAGGCCC | AGCGCCCCTC | 5400 |
| CGCTGCCTCC | CGTCGCCGAC | CTGCCACAGC | CGGGGCTGCG | GCGCTGACGG | CTGTGGCGCC | 5460 |
| TGCCCATGAC | ACCTCACCCG | TCCCGGACGT | TGATTCTCGC | GGTGCAATTC | TACGCCGCCA | 5520 |
| GTATAATTTG | TCTACTTCAC | CCCTGACATC | CTCTGTGGCC | TCTGGCACTA | ATTTAGTCCT | 5580 |
| GTATGCAGCC | CCCCTTAATC | CGCCTCTGCC | GCTGCAGGAC | GGTACTAATA | CTCACATTAT | 5640 |
| GGCCACAGAG | GCCTCCAATT | ATGCACAGTA | CCGGGTTGCC | CGCGCTACTA | TCCGTTACCG | 5700 |
| GCCCCTAGTG | CCTAATGCAG | TTGGAGGCTA | TGCTATATCC | ATTTCTTTCT | GGCCTCAAAC | 5760 |
| AACCACAACC | CCTACATCTG | TTGACATGAA | TTCCATTACT | TCCACTGATG | TCAGGATTCT | 5820 |
| TGTTCAACCT | GGCATAGCAT | CTGAATTGGT | CATCCCAAGC | GAGCGCCTTC | ACTACCGCAA | 5880 |
| TCAAGGTTGG | CGCTCGGTTG | AGACATCTGG | TGTTGCTGAG | GAGGAAGCCA | CCTCCGGTCT | 5940 |
| TGTCATGTTA | TGCATACATG | GCTCTCCAGT | TAACTCCTAT | ACCAATACCC | CTTATACCGG | 6000 |
| TGCCCTTGGC | TTACTGGACT | TTGCCTTAGA | GCTTGAGTTT | CGCAATCTCA | CCACCTGTAA | 6060 |
| CACCAATACA | CGTGTGTCCC | GTTACTCCAG | CACTGCTCGT | CACTCCGCCC | GAGGGGCCGA | 6120 |
| CGGGACTGCG | GAGCTGACCA | CAACTGCAGC | CACCAGGTTC | ATGAAAGATC | TCCACTTTAC | 6180 |
| CGGCCTTAAT | GGGGTAGGTG | AAGTCGGCCG | CGGGATAGCT | CTAACATTAC | TTAACCTTGC | 6240 |
| TGACACGCTC | CTCGGCGGGC | TCCCGACAGA | ATTAATTTCG | TCGGCTGGCG | GGCAACTGTT | 6300 |
| TTATTCCCGC | CCGGTTGTCT | CAGCCAATGG | CGAGCCAACC | GTGAAGCTCT | ATACATCAGT | 6360 |
| GGAGAATGCT | CAGCAGGATA | AGGGTGTTGC | TATCCCCCAC | GATATCGATC | TTGGTGATTC | 6420 |
| GCGTGTGGTC | ATTCAGGATT | ATGACAACCA | GCATGAGCAG | GATCGGCCCA | CCCCGTCGCC | 6480 |
| TGCGCCATCT | CGGCCTTTTT | CTGTTCTCCG | AGCAAATGAT | GTACTTTGGC | TGTCCCTCAC | 6540 |
| TGCAGCCGAG | TATGACCAGT | CCACTTACGG | GTCGTCAACT | GGCCCGGTTT | ATATCTCGGA | 6600 |
| CAGCGTGACT | TTGGTGAATG | TTGCGACTGG | CGCGCAGGCC | GTAGCCCGAT | CGCTTGACTG | 6660 |
| GTCCAAAGTC | ACCCTCGACG | GGCGGCCCCT | CCCGACTGTT | GAGCAATATT | CCAAGACATT | 6720 |
| CTTTGTGCTC | CCCCTTCGTG | GCAAGCTCTC | CTTTTGGGAG | GCCGGCACAA | CAAAAGCAGG | 6780 |
| TTATCCTTAT | AATTATAATA | CTACTGCTAG | TGACCAGATT | CTGATTGAAA | ATGCTGCCGG | 6840 |
| CCATCGGGTC | GCCATTTCAA | CCTATACCAC | CAGGCTTGGG | GCCGGTCCGG | TCGCCATTTC | 6900 |
| TGCGGCCGCG | GTTTGGCTC | CACGCTCCGC | CCTGGCTCTG | CTGGAGGATA | CTTTGATTA | 6960 |
| TCCGGGGCGG | GCGCACACAT | TGATGACTT | CTGCCCTGAA | TGCCGCGCTT | TAGGCCTCCA | 7020 |
| GGGTTGTGCT | TTCCAGTCAA | CTGTCGCTGA | GCTCCAGCGC | CTTAAAGTTA | AGGTGGGTAA | 7080 |
| AACTCGGGAG | TTGTAGTTTA | TTTGGCTGTG | CCCACCTACT | TATATCTGCT | GATTTCCTTT | 7140 |
| ATTTCCTTTT | TCTCGGTCCC | GCGCTCCCTG | A | | | 7171 |

(2) INFORMATION FOR SEQ ID NO:11:

( i ) SEQUENCE CHARACTERISTICS:
  ( A ) LENGTH: 1575 base pairs
  ( B ) TYPE: nucleic acid
  ( C ) STRANDEDNESS: double
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: T: Mexican strain ( x i ) SEQUENCE DESCRIPTION: SEQ ID NO:11:

| | | | | | |
|---|---|---|---|---|---|
| GTTGCGTGAG | GTGGGTATCT | CAGATGCCAT | TGTTAATAAT | TTCTTCCTTT | CGGGTGGCGA | 60 |
| GGTTGGTCAC | CAGAGACCAT | CGGTCATTCC | GCGAGGCAAC | CCTGACCGCA | ATGTTGACGT | 120 |
| GCTTGCGGCG | TTTCCACCTT | CATGCCAAAT | AAGCGCCTTC | CATCAGCTTG | CTGAGGAGCT | 180 |
| GGGCCACCGG | CCGGCGCCGG | TGGCGGCTGT | GCTACCTCCC | TGCCCTGAGC | TTGAGCAGGG | 240 |
| CCTTCTCTAT | CTGCCACAGG | AGCTAGCCTC | CTGTGACAGT | GTTGTGACAT | TTGAGCTAAC | 300 |
| TGACATTGTG | CACTGCCGCA | TGGCGGCCCC | TAGCCAAAGG | AAAGCTGTTT | TGTCCACGCT | 360 |
| GGTAGGCCGG | TATGGCAGAC | GCACAAGGCT | TTATGATGCG | GGTCACACCG | ATGTCCGCGC | 420 |
| CTCCCTTGCG | CGCTTTATTC | CCACTCTCGG | GCGGGTTACT | GCCACCACCT | GTGAACTCTT | 480 |
| TGAGCTTGTA | GAGGCGATGG | TGGAGAAGGG | CCAAGACGGT | TCAGCCGTCC | TCGAGTTGGA | 540 |
| TTTGTGCAGC | CGAGATGTCT | CCCGCATAAC | CTTTTCCAG | AAGGATTGTA | ACAAGTTCAC | 600 |
| GACCGGCGAG | ACAATTGCGC | ATGGCAAAGT | CGGTCAGGGT | ATCTTCCGCT | GGAGTAAGAC | 660 |
| CTTTTGTGCC | CTGTTTGGCC | CCTGGTTCCG | TGCGATTGAG | AAGGCTATTC | TATCCCTTTT | 720 |
| ACCACAAGCT | GTGTTCTACG | GGGATGCTTA | TGACGACTCA | GTATTCTCTG | CTGCCGTGGC | 780 |
| TGGCGCCAGC | CATGCCATGG | TGTTTGAAAA | TGATTTTTCT | GAGTTTGACT | CGACTCAGAA | 840 |
| TAACTTTTCC | CTAGGTCTTG | AGTGCGCCAT | TATGGAAGAG | TGTGGTATGC | CCCAGTGGCT | 900 |
| TGTCAGGTTG | TACCATGCCG | TCCGGTCGGC | GTGGATCCTG | CAGGCCCCAA | AAGAGTCTTT | 960 |
| GAGAGGGTTC | TGGAAGAAGC | ATTCTGGTGA | GCCGGGCACG | TTGCTCTGGA | ATACGGTGTG | 1020 |
| GAACATGGCA | ATCATTGCCC | ATTGCTATGA | GTTCCGGGAC | CTCCAGGTTG | CCGCCTTCAA | 1080 |
| GGGCGACGAC | TCGGTCGTCC | TCTGTAGTGA | ATACCGCCAG | AGCCCAGGCG | CCGGTTCGCT | 1140 |
| TATAGCAGGC | TGTGGTTTGA | AGTTGAAGGC | TGACTTCCGG | CCGATTGGGC | TGTATGCCGG | 1200 |
| GGTTGTCGTC | GCCCCGGGGC | TCGGGCCCT | ACCCGATGTC | GTTCGATTCG | CCGGACGGCT | 1260 |
| TTCGGAGAAG | AACTGGGGGC | CTGATCCGGA | GCGGGCAGAG | CAGCTCCGCC | TCGCCGTGCA | 1320 |
| GGATTTCCTC | CGTAGGTTAA | CGAATGTGGC | CCAGATTTGT | GTTGAGGTGG | TGTCTAGAGT | 1380 |
| TTACGGGGTT | TCCCCGGGTC | TGGTTCATAA | CCTGATAGGC | ATGCTCCAGA | CTATTGGTGA | 1440 |
| TGGTAAGGCG | CATTTTACAG | AGTCTGTTAA | GCCTATACTT | GACCTTACAC | ACTCAATTAT | 1500 |
| GCACCGGTCT | GAATGAATAA | CATGTGGTTT | GCTGCGCCCA | TGGGTTCGCC | ACCATGCGCC | 1560 |
| CTAGGCCTCT | TTTGC | | | | | 1575 |

( 2 ) INFORMATION FOR SEQ ID NO:12:

( i ) SEQUENCE CHARACTERISTICS:
    ( A ) LENGTH: 874 base pairs
    ( B ) TYPE: nucleic acid
    ( C ) STRANDEDNESS: double
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: Tashkent strain ( x i ) SEQUENCE DESCRIPTION: SEQ ID NO:12:

| CGGGCCCCGT | ACAGGTCACA | ACCTGTGAGT | TGTACGAGCT | AGTGGAGGCC | ATGGTCGAGA | 60 |
|---|---|---|---|---|---|---|
| AAGGCCAGGA | TGGCTCCGCC | GTCCTTGAGC | TCGATCTCTG | CAACCGTGAC | GTGTCCAGGA | 120 |
| TCACCTTTTT | CCAGAAAGAT | TGCAATAAGT | TCACCACGGG | AGAGACCATC | GCCCATGGTA | 180 |
| AAGTGGGCCA | GGGCATTTCG | GCCTGGAGTA | AGACCTTCTG | TGCCCTTTTC | GGCCCCTGGT | 240 |
| TCCGTGCTAT | TGAGAAGGCT | ATTCTGGCCC | TGCTCCCTCA | GGGTGTGTTT | TATGGGGATG | 300 |
| CCTTTGATGA | CACCGTCTTC | TCGGCGCGTG | TGGCCGCAGC | AAAGGCGTCC | ATGGTGTTTG | 360 |
| AGAATGACTT | TTCTGAGTTT | GACTCCACCC | AGAATAATTT | TTCCCTGGGC | CTAGAGTGTG | 420 |
| CTATTATGGA | GAAGTGTGGG | ATGCCGAAGT | GGCTCATCCG | CTTGTACCAC | CTTATAAGGT | 480 |
| CTGCGTGGAT | CCTGCAGGCC | CCGAAGGAGT | CCCTGCGAGG | GTGTTGGAAG | AAACACTCCG | 540 |
| GTGAGCCCGG | CACTCTTCTA | TGGAATACTG | TCTGGAACAT | GGCCGTTATC | ACCCATTGTT | 600 |
| ACGATTTCCG | CGATTTGCAG | GTGGCTGCCT | TTAAAGGTGA | TGATTCGATA | GTGCTTTGCA | 660 |
| GTGAGTACCG | TCAGAGTCCA | GGGGCTGCTG | TccTGATTGc | TGGCTGTGGC | TTAAAGCTGA | 720 |
| AGGTGGGTTT | CCGTCCGATT | GGTTTGTATG | CAGGTGTTGT | GGTGACCCCC | GGCCTTGGCG | 780 |
| CGCTTCCCGA | CGTCGTGCGC | TTGTCCGGCC | GGCTTACTGA | GAAGAATTGG | GGCCCTGGCC | 840 |
| CTGAGCGGGC | GGAGCAGCTC | CGCCTTGCTG | TGCG | | | 874 |

( 2 ) INFORMATION FOR SEQ ID NO:13:

( i ) SEQUENCE CHARACTERISTICS:
    ( A ) LENGTH: 449 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: Clone 406.4-2 cDNA ( i x ) FEATURE:
    ( A ) NAME/KEy: CDS
    ( B ) LOCATION: 2..100

( x i ) SEQUENCE DESCRIPTION: SEQ ID NO:13:

```
C GCC AAC CAG CCC GGC CAC TTG GCT CCA CTT GGC GAG ATC AGG CCC      46
  Ala Asn Gln Pro Gly His Leu Ala Pro Leu Gly Glu Ile Arg Pro
  1               5                  10                  15

AGC GCC CCT CCG CTG CCT CCC GTC GCC GAC CTG CCA CAG CCG GGG CTG   94
Ser Ala Pro Pro Leu Pro Pro Val Ala Asp Leu Pro Gln Pro Gly Leu
              20                  25                  30

CGG CGC TGACGGCTGT GGCGCCTGCC CATGACACCT CACCCGTCCC GGACGTTGAT    150
Arg Arg
```

| TCTCGCGGTG | CAATTCTACG | CCGCCAGTAT | AATTTGTCTA | CTTCACCCCT | GACATCCTCT | 210 |
|---|---|---|---|---|---|---|
| GTGGCCTCTG | GCACTAATTT | AGTCCTGTAT | GCAGCCCCCC | TTAATCCGCC | TCTGCCGCTG | 270 |

```
CAGGACGGTA CTAATACTCA CATTATGGCC ACAGAGGCCT CCAATTATGC ACAGTACCGG    330

GTTGCCCGCG CTACTATCCG TTACCGGCCC CTAGTGCCTA ATGCAGTTGG AGGCTATGCT    390

ATATCCATTT CTTTCTGGCC TCAAACAACC ACAACCCCTA CATCTGTTGA CATGAATTC     449
```

( 2 ) INFORMATION FOR SEQ ID NO:14:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

```
Ala  Asn  Gln  Pro  Gly  His  Leu  Ala  Pro  Leu  Gly  Glu  Ile  Arg  Pro  Ser
 1                   5                        10                       15

Ala  Pro  Pro  Leu  Pro  Pro  Val  Ala  Asp  Leu  Pro  Gln  Pro  Gly  Leu  Arg
               20                       25                       30

Arg
```

( 2 ) INFORMATION FOR SEQ ID NO:15:

( i ) SEQUENCE CHARACTERISTICS:
    ( A ) LENGTH: 130 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: Clone 406.3-2

( i x ) FEATURE:
    ( A ) NAME/KEy: CDS
    ( B ) LOCATION: 5..130

( x i ) SEQUENCE DESCRIPTION: SEQ ID NO:15:

```
GGAT ACT TTT GAT TAT CCG GGG CGG GCG CAC ACA TTT GAT GAC TTC TGC         4
     Thr Phe Asp Tyr Pro Gly Arg Ala His Thr Phe Asp Asp Phe Cys
      1           5                   10                      15

CCT GAA TGC CGC GCT TTA GGC CTC CAG GGT TGT GCT TTC CAG TCA ACT          9
Pro Glu Cys Arg Ala Leu Gly Leu Gln Gly Cys Ala Phe Gln Ser Thr
              20                  25                  30

GTC GCT GAG CTC CAG CGC CTT AAA GTT AAG GTT                             13
Val Ala Glu Leu Gln Arg Leu Lys Val Lys Val
            35                  40
```

( 2 ) INFORMATION FOR SEQ ID NO:16:

( i ) SEQUENCE CHARACTERISTICS:
    ( A ) LENGTH: 42 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

```
Thr  Phe  Asp  Tyr  Pro  Gly  Arg  Ala  His  Thr  Phe  Asp  Asp  Phe  Cys  Pro
 1                   5                        10                       15

Glu  Cys  Arg  Ala  Leu  Gly  Leu  Gln  Gly  Cys  Ala  Phe  Gln  Ser  Thr  Val
               20                       25                       30
```

```
Ala Glu Leu Gln Arg Leu Lys Val Lys Val
             35                  40
```

( 2 ) INFORMATION FOR SEQ ID NO:17:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: 406.4-2 epitope - Mexican strain ( x i ) SEQUENCE DESCRIPTION: SEQ ID NO:17:

```
Ala Asn Gln Pro Gly His Leu Ala Pro Leu Gly Glu Ile Arg Pro Ser
1               5                   10                  15
Ala Pro Pro Leu Pro Pro Val Ala Asp Leu Pro Gln Pro Gly Leu Arg
                20                  25                  30
Arg
```

( 2 ) INFORMATION FOR SEQ ID NO:18:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: 406.4-2 epitope - Burma strain ( x i ) SEQUENCE DESCRIPTION: SEQ ID NO:18:

```
Ala Asn Pro Pro Asp His Ser Ala Pro Leu Gly Val Thr Arg Pro Ser
1               5                   10                  15
Ala Pro Pro Leu Pro His Val Val Asp Leu Pro Gln Leu Gly Pro Arg
                20                  25                  30
Arg
```

( 2 ) INFORMATION FOR SEQ ID NO:19:

( i ) SEQUENCE CHARACTERISTICS:
        ( A ) LENGTH: 42 amino acids
        ( 8 ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: 406.3-2 epitope - Mexican strain ( x i ) SEQUENCE DESCRIPTION: SEQ ID NO:19:

```
Thr  Phe  Asp  Tyr  Pro  Gly  Arg  Ala  His  Thr  Phe  Asp  Asp  Phe  Cys  Pro
1              5                        10                      15

Glu  Cys  Arg  Ala  Leu  Gly  Leu  Gln  Gly  Cys  Ala  Phe  Gln  Ser  Thr  Val
               20                       25                      30

Ala  Glu  Leu  Gln  Arg  Leu  Lys  Val  Lys  Val
          35                       40
```

( 2 ) INFORMATION FOR SEQ ID NO:20:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: 406.3-2 epitope - Burma strain ( x i ) SEQUENCE DESCRIPTION: SEQ ID NO:20:

```
Thr  Leu  Asp  Tyr  Pro  Ala  Arg  Ala  His  Thr  Phe  Asp  Asp  Phe  Cys  Pro
1              5                        10                      15

Glu  Cys  Arg  Pro  Leu  Gly  Leu  Gln  Gly  Cys  Ala  Phe  Gln  Ser  Thr  Val
               20                       25                      30

Ala  Glu  Leu  Gln  Arg  Leu  Lys  Met  Lys  Val
          35                       40
```